(12) United States Patent
Lapotko et al.

(10) Patent No.: US 10,471,159 B1
(45) Date of Patent: Nov. 12, 2019

(54) DIAGNOSIS, REMOVAL, OR MECHANICAL DAMAGING OF TUMOR USING PLASMONIC NANOBUBBLES

(71) Applicant: Masimo Corporation, Irvine, CA (US)

(72) Inventors: Dmitri O. Lapotko, Dana Point, CA (US); Katsiaryna Hleb, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 369 days.

(21) Appl. No.: 15/430,321

(22) Filed: Feb. 10, 2017

Related U.S. Application Data

(60) Provisional application No. 62/294,833, filed on Feb. 12, 2016, provisional application No. 62/294,831, filed on Feb. 12, 2016, provisional application No. 62/294,824, filed on Feb. 12, 2016.

(51) Int. Cl.
*A61K 49/22* (2006.01)
*A61B 5/00* (2006.01)

(52) U.S. Cl.
CPC .......... *A61K 49/223* (2013.01); *A61B 5/0095* (2013.01); *A61K 49/221* (2013.01)

(58) Field of Classification Search
CPC ... A61K 49/221; A61K 49/223; A61B 5/0095
See application file for complete search history.

(56) References Cited

U.S. PATENT DOCUMENTS 7,230,708 B2 6/2007 Lapotko et al.
7,999,161 B2 8/2011 Oraevsky et al.
2014/0120167 A1* 5/2014 Lapotko ............. A61K 41/0038
424/490

OTHER PUBLICATIONS

Anderson et al., "Optically Guided Controlled Release from Liposomes with Tubable Plasmonic Nanobubbles," Journal of Controlled Release, vol. 144, Issue 2, Jun. 1, 2010, in 22 pages.
Brusnichkin et al., "Determination of Various Hemoglobin Species with Thermal-Lens Spectrometry," Moscow University Chemistry Bulletin, vol. 64, Issue 1, Feb. 2009, pp. 45-54.
Conjusteau et al., "Metallic Nanoparticles as Optoacoustic Contrast Agents for Medical Imaging," SPIE Proceedings, vol. 6086, Photons Plus Ultrasound: Imaging and Sensing 2006: The Seventh Conference on Biomedical Thermoacoustics, Optoacoustics, and Acousto-optics, Mar. 6, 2006, in 9 pages.

(Continued)

*Primary Examiner* — Michael T Rozanski
(74) *Attorney, Agent, or Firm* — Knobbe, Martens, Olson & Bear, LLP

(57) ABSTRACT

Processes of intraoperative diagnosis and elimination of tumors or micro-tumors or cancer cells or tumor microenvironment (TME) with plasmonic nanobubbles (PNBs) are disclosed. The diagnosis and surgical processes disclosed can improve standard onco-surgery through one or more of the following: real-time intraoperative local detection of MRD in vivo with high cancer sensitivity and specificity; real-time guidance of surgery to precisely eliminate resectable MRD with minimal morbidity by resecting only PNB-positive volume instead of a larger volume; intraoperative selective elimination of unresectable MRD through the mechanical impact of lethal cancer cell-specific PNBs without damaging adjacent normal cells and tissues; and prediction of the surgical outcome through the metrics of PNB signals.

19 Claims, 23 Drawing Sheets

(56) References Cited

OTHER PUBLICATIONS

Danysh et al., "The MUCI Ectodomain: A Novel and Efficient Target for Gold Nanoparticle Clustering and Vapor Nanobubble Generation," Theranostics, 2, No. 8, Ivyspring International Publisher, 2012, pp. 777-787.

Lapotko et al., "Clusterization of Nanoparticles During their Interaction with Living Cells," Nanomedicine, vol. 2, No. 2, Apr. 2007, pp. 241-253.

Lapotko et al., "Elimination of Leukemic Cells from Human Transplants by Laser Nano-Thermolysis," SPIE Proceedings, vol. 6086, Photons Plus Ultrasound: Imaging and Sensing 2006: The Seventh Conference on Biomedical Thermoacoustics, Optoacoustics, and Acousto-optics, Mar. 6, 2006, in 8 pages.

Lapotko et al., "Lantcet: Novel Laser Nanotechnology for Graft Purging," Biology of Blood and Marrow Transplantation, Feb. 2006, in 2 pages.

Lapotko et al., "Laser Activated Nanothermolysis of Leukemia Cells Monitored by Photothermal Microscopy," SPIE Proceedings, vol. 5697, Photons Plus Ultrasound: Imaging and Sensing 2006: The Seventh Conference on Biomedical Thermoacoustics, Optoacoustics, and Acousto-optics, May 5, 2005, pp. 82-89.

Lapotko et al., "Laser Heating Diagnoses and Treats Cancerous Cells," SPIE Newsroom, The International Society for Optical Engineering, 2006, in 3 pages.

Lapotko et al., "Method of Laser Activated Nano-Thermolysis for Elimination of Tumor Cells," Cancer Letters, vol. 239, Issue 1, Jul. 28, 2006, pp. 36-45.

Lapotko, "Monitoring of Apoptosis in Intact Single Cells with Photothermal Microscope," Journal of the International Society for Advancement of Cytometry, vol. 58A, Issue 2, Apr. 2004, pp. 111-119.

Lapotko, "Optical Excitation and Detection of Vapor Bubbles Around Plasmonic Nanoparticles," Optics Express, vol. 17, Issue 4, Feb. 16, 2009, pp. 2538-2556.

Lapotko et al., "Photothermal and Photoacoustic Processes in Laser Activated Nano-Thermolysis of Cells," SPIE Proceedings, vol. 6437, Photons Plus Ultrasound: Imaging and Sensing 2007: The Eighth Conference on Biomedical Thermoacoustics, Optoacoustics, and Acousto-optics, Mar. 2007, in 13 pages.

Lapotko et al., "Photothermal Detection of Laser-Induced Damage in Single Intact Cells," Lasers in Surgery and Medicine, vol. 33, Issue 5, Dec. 2003, pp. 320-329.

Lapotko et al., "Photothermal Image Cytometry of Human Neutrophils," Journal of the International Society for Advancement of Cytometry, vol. 24, Issue 3, Jul. 1, 1996, pp. 198-203.

Lapotko et al., "Photothermal Response of Live Cells Depends Upon Cell Metabolic State," SPIE Proceedings, vol. 4618, Biomedical Optoacoustics III, Jun. 10, 2002, in 8 pages.

Lapotko et al., "Photothermal Time-Resolved Imaging of Living Cells," Lasers in Surgery and Medicine, vol. 31, Issue 1, Jul. 2002, pp. 53-63.

Lapotko et al., "Photothermolysis by Laser-Induced Microbubbles Generated Around Gold Nanorod Clusters Selectively Formed in Leukemia Cells," SPIE Proceedings, vol. 6856, Photons Plus Ultrasound: Imaging and Sensing 2008: The Ninth Conference on Biomedical Thermoacoustics, Optoacoustics, and Acousto-optics, Feb. 28, 2008, in 10 pages.

Lapotko, "Plasmonic Nanobubbles as Tunable Cellular Probes for Cancer Theranostics," Cancers, vol. 3, No. 1, 2011 pp. 802-840.

Lapotko, "Plasmonic Nanoparticle-Generated Photothermal Bubbles and their Biomedical Applications," Nanomedicine, vol. 4, No. 7, Oct. 2009, pp. 813-845.

Lapotko, "Nanophotonics and Theranostics: Will Light do the Magic?" Theranostics 2013, vol. 3, Issue 3, pp. 138-140.

Lapotko et al., "Nonstationary Heating and Phase Transitions in a Live Cell in Absorption of Laser Radiation," Heat Transfer Research, vol. 38, Issue 8, Jan. 2007, pp. 695-708.

Lapotko et al., "Selective Laser Nano-Thermolysis of Human Leukemia Cells with Microbubbles Generated Around Clusters of Gold Nanoparticles," Lasers in Surgery and Medicine, vol. 38, Issue 6, Jul. 2006, pp. 631-642.

Lapotko, "Therapy with Gold Nanoparticles and Lasers: What Really Kills the Cells?" Nanomedicine, vol. 4, No. 3, Apr. 2009, pp. 253-256.

Lukianova-Hleb et al., "All-in-one Processing of Heterogeneous Human Cell Grafts for Gene and Cell Therapy," Molecular Therapy— Methods & Clinical Development , vol. 3, Article 16012, 2016, in 8 pages.

Lukianova-Hleb et al., "Cell-Specific Multifunctional Processing of Heterogeneous Cell Systems in a Single Laser Pulse Treatment," ACS Nano, vol. 6, Issue 12, Dec. 21, 2012, pp. 10973-10981.

Lukianova-Hleb et al., "Cell-Specific Transmembrane Injection of Molecular Cargo with Gold Nanoparticle-Generated Transient Plasmonic Nanobubbles," Biomaterials, vol. 33, Issue 21, Jul. 2012, pp. 5441-5450.

Lukianova-Hleb et al., "Generation and Detection of Plasmonic Nanobubbles in Zebrafish," Nanotechnology, vol. 21, No. 22, Jun. 4, 2010, in 22 pages.

Lukianova-Hleb et al., "Hemozoin-Generated Vapor Nanobubbles for Transdermal Reagent and Needle-Free Detection of Malaria," Proceedings of the National Academy of Sciences of the United States of America, vol. 111, No. 3, Jan. 21, 2014, pp. 900-905.

Lukianova-Hleb et al., "Improved Cellular Specificity of Plasmonic Nanobubbles versus Nanoparticles in Heterogeneous Cell Systems," PLoS One, vol. 7, Issue 4, Apr. 2012, in 10 pages.

Lukianova-Hleb et al., "Intraoperative Diagnostics and Elimination of Residual Micro-Tumours with Plasmonic Nanobubbles," Nature Nanotechnology, 2015, in 31 pages.

Lukianova-Hleb et al., "Influence of Transient Environmental Photothermal Effects on Optical Scattering by Gold Nanoparticles," Nano Letters, vol. 9, Issue 5, May 2009, pp. 2160-2166.

Lukianova-Hleb et al., "Laser Pulse Duration is Critical for the Generation of Plasmonic Nanobubbles," Langmuir, vol. 30, Issue 25, 2014, pp. 7425-7434.

Lukianova-Hleb et al., "Malaria Theranostics Using Hemozoin-Generated Vapor Nanobubbles," Theranostics, vol. 4, Issue 7, 2014, pp. 761-769.

Lukianova-Hleb et al., "Multifunctional Cell Processing with Plasmonic Nanobubbles," International Journal of Medical, Health, Biomedical, Bioengineering and Pharmaceutical Engineering, vol. 7, No. 11, 2013, pp. 677-681.

Lukianova-Hleb et al., "Plasmonic Nanobubbles Enhance Efficacy and Selectivity of Chemotherapy Against Drug-Resistant Cancer Cells," Advanced Materials, vol. 24, Issue 28, Jul. 24, 2012, pp. 3831-3837.

Lukianova-Hleb et al., "Plasmonic Nanobubbles for Intracellular Targeting and Gene Therapy," NTSI-Nanotech 2011, vol. 3, pp. 291-294.

Lukianova-Hleb et al., "Plasmonic Nanobubbles as Transient Vapor Nanobubbles Generated Around Plasmonic Nanoparticles," ACS Nano, vol. 4, Issue 4, Apr. 27, 2010, pp. 2109-2123.

Lukianova-Hleb et al., "Plasmonic Nanobubble-Enhanced Endosomal Escape Processes for Selective and Guided Intracellular Delivery of Chemotherapy to Drug-Resistant Cancer Cells," Biomaterials, vol. 33, Issue 6, Feb. 2012, pp. 1821-1826.

Lukianova-Hleb et al., "Plasmonic Nanobubbles Rapidly Detect and Destroy Drug-Resistant Tumors," Theranostics, vol. 2, No. 10, 2012, pp. 976-787.

Lukianova-Hleb et al., "Plasmonic Nanobubbles as Tunable Theranostic Agents," NSTI-Nanotech 2011, vol. 3, pp. 367-370.

Lukianova-Hleb et al., "Plasmonic Nanobubbles: Tunable and Transient Probes for Cancer Diagnosis, Therapy and Theranostics," NSTI-Nanotech 2010, vol. 3, 2010 in 5 pages.

Lukianova-Hleb et al., "Rainbow Plasmonic Nanobubbles: Synergistic Activation of Gold Nanoparticle Clusters," Journal of Nanomedicine & Nanotechnology, vol. 2, Issue 104, Jan. 1, 2011, in 21 pages.

(56) References Cited

OTHER PUBLICATIONS

Lukianova-Hleb et al., "Safety and Efficacy of Quadrapeutics Versus Chemoradiation in Head and Neck Carcinoma Xenograft Model," American Journal of Cancer Research, vol. 5, Issue 12, 2015, pp. 3534-3547.

Lukianova-Hleb et al., "Selective Gene Transfection of Individual Cells In Vitro with Plasmonic Nanobubbles," Journal of Controlled Release, vol. 152, Issue 2, Jun. 10, 2011, pp. 286-293.

Lukianova-Hleb et al., "Selective and Self-Guided Micro-Ablation of Tissue with Plasmonic Nanobubbles," Journal of Surgical Research, vol. 166, Issue 1, Mar. 2011, pp. e3-e13.

Lukianova-Hleb et al., "Short Laser Pulse-Induced Irreversible Photothermal Effects in Red Blood Cells," Lasers in Surgery and Medicine, vol. 43, Issue 3, Mar. 2011, pp. 249-260.

Lukianova-Hleb et al., "Transdermal Diagnosis of Malaria Using Vapor Nanobubbles," Emerging Infectious Diseases, vol. 21, No. 7, Jul. 2015, pp. 1122-1127.

Lukianova-Hleb et al., "Transient Enhancement and Spectral Narrowing of the Photothermal Effect of Plasmonic Nanoparticles Under Pulsed Excitation," Advanced Materials, Voume 25, Issue 5, Feb. 6, 2013, pp. 772-776.

Lukianova-Hleb et al., "Transient Photothermal Spectra of Plasmonic Nanobubbles," Langmuir, vol. 28, Issue 10, Feb. 2012, pp. 4858-4866.

Lukianova-Hleb et al., "Tunable Plasmonic Nanobubbles for Cell Theranostics," Nanotechnology, vol. 21, No. 8, Feb. 26, 2010, in 19 pages.

Lukianova-Hleb et al., "Tunable Plasmonic Nanoprobes for Theranostics of Prostate Cancer," Theranostics, vol. 1, 2011, pp. 3-17.

Potkin et al., "The Influence of Heterocyclic Compound-Pamam Dendrimer Complexes on Evoked Electrical Responses in Slices of Hypoxic Brain Tissue," Cellular & Molecular Biology Letters, vol. 19, 2014, pp. 243-248.

Vasiliev et al., "Bubble Generation in Micro-Volumes of 'nonofluids'," International Journal of Heat and Mass Transfer, vol. 52, Issues 5-6, Feb. 2009, pp. 1534-1539.

\* cited by examiner

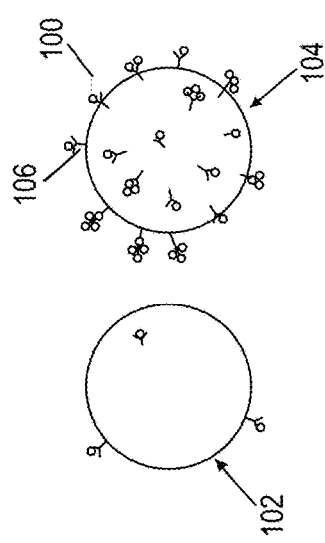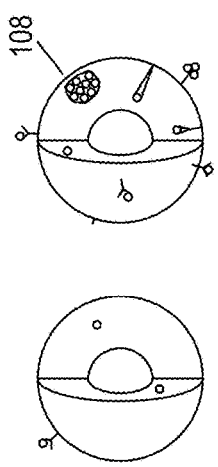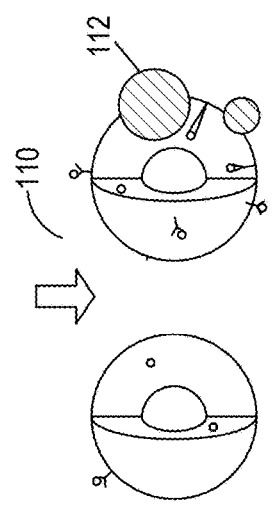

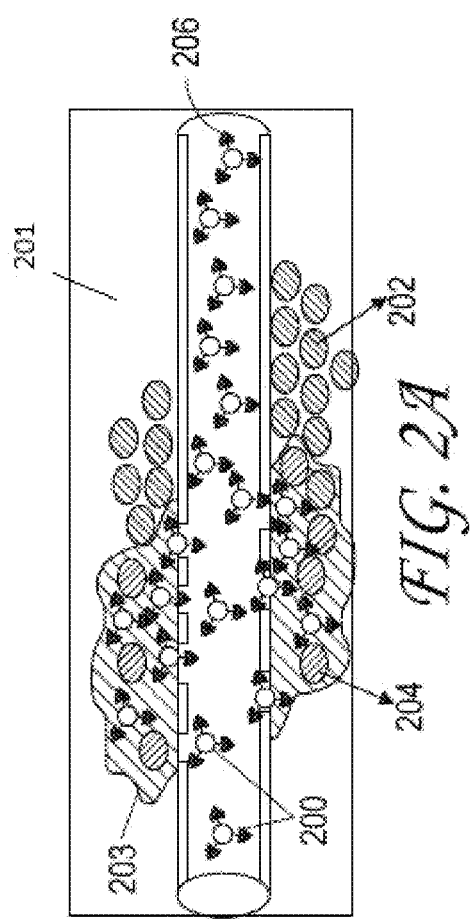

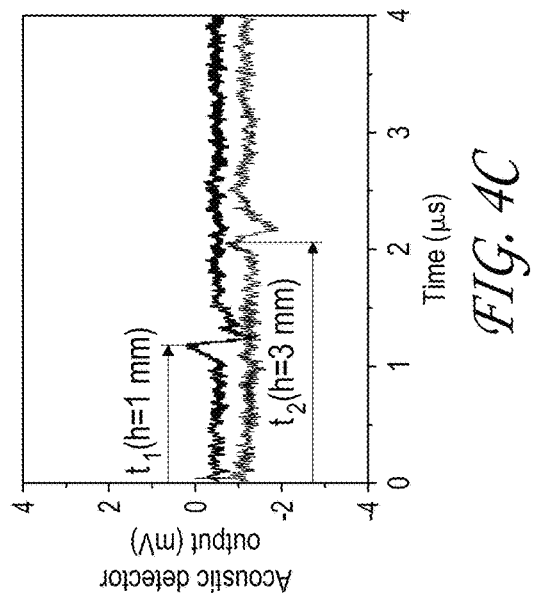
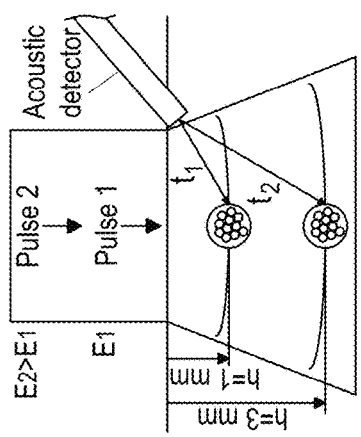
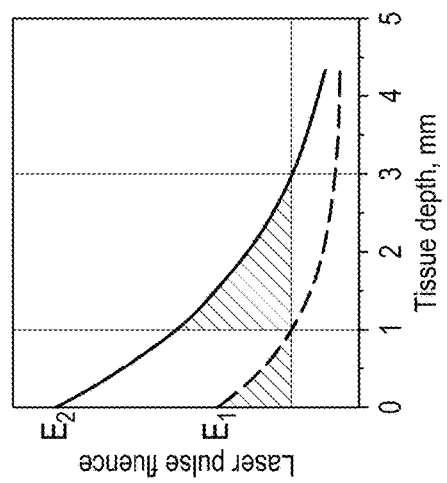
FIG. 4A
FIG. 4B
FIG. 4C

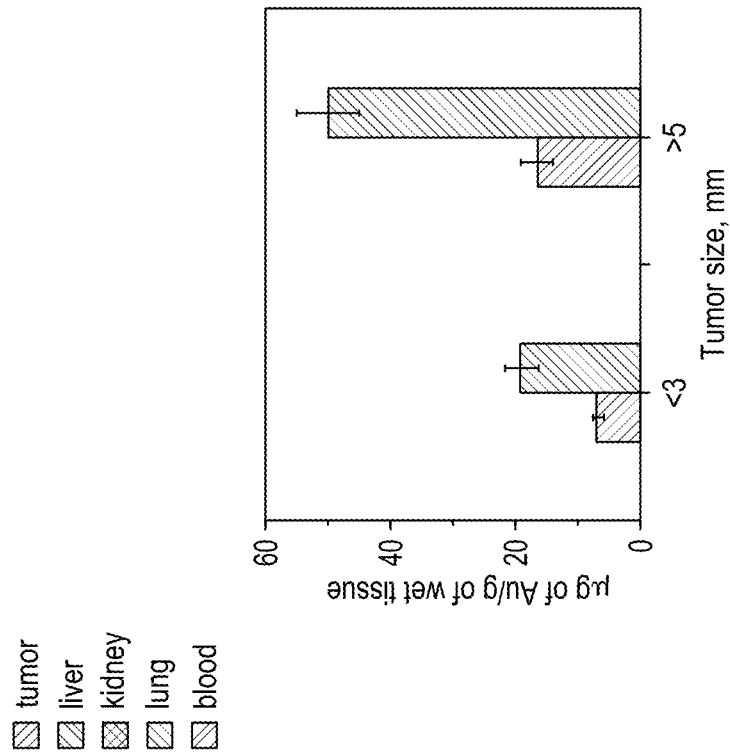
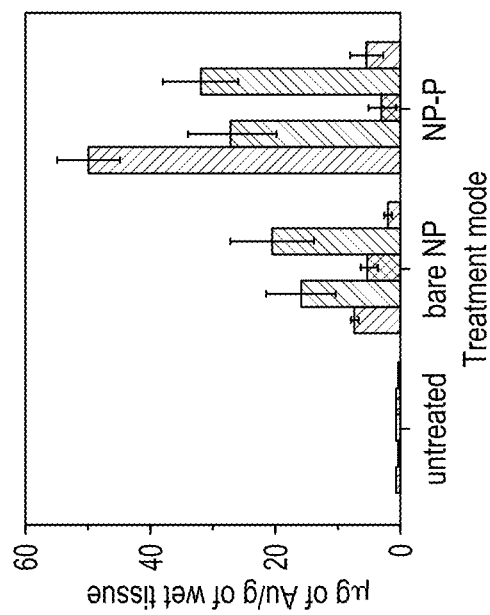
FIG. 10A
FIG. 10B

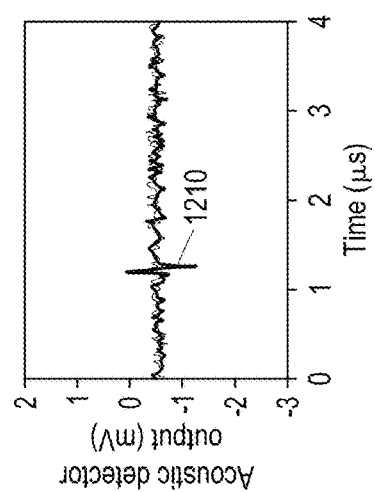
*FIG. 12C*
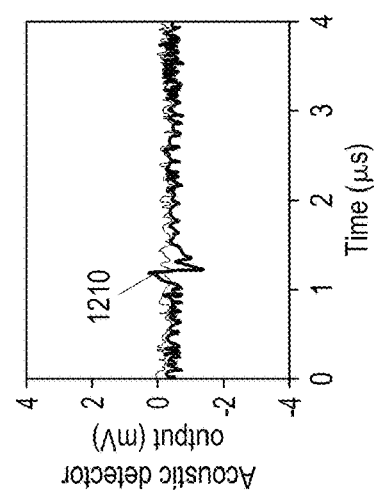
*FIG. 12F*
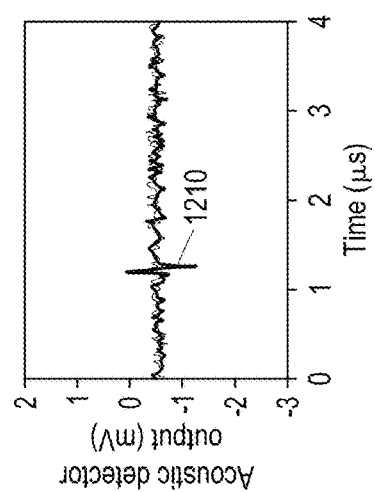
*FIG. 12B*
*FIG. 12E*
*FIG. 12A*
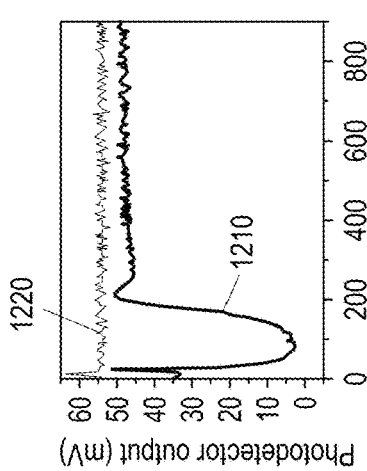
*FIG. 12D*

DIAGNOSIS, REMOVAL, OR MECHANICAL DAMAGING OF TUMOR USING PLASMONIC NANOBUBBLES

INCORPORATION BY REFERENCE TO ANY PRIORITY APPLICATIONS

This application claims the benefit of priority under 35 U.S.C. § 119(e) to U.S. Patent Application No. 62/294,833, entitled "INTRAOPERATIVE DIAGNOSIS OF TUMORS AND RESIDUAL MICRO-TUMORS AND TUMOR MICRO-ENVIRONMENT WITH PLASMONIC NANOBUBBLES," filed Feb. 12, 2016, U.S. Patent Application No. 62/294,831, entitled "INTRAOPERATIVE DIAGNOSIS OF TUMORS AND RESIDUAL MICRO-TUMORS AND TUMOR MICRO-ENVIRONMENT WITH PLASMONIC NANOBUBBLES," filed Feb. 12, 2016, and to U.S. Patent Application No. 62/294,824, entitled "INTRAOPERATIVE DIAGNOSIS OF TUMORS AND RESIDUAL MICRO-TUMORS AND TUMOR MICRO-ENVIRONMENT WITH PLASMONIC NANOBUBBLES," filed Feb. 12, 2016; each of the foregoing applications is hereby incorporated by reference herein in its entirety.

BACKGROUND

The present application relates generally to the fields of cancer cell or residual microtumor detection and elimination. More particularly, the present application relates to intraoperative diagnostic and elimination of cancer cells in vivo.

SUMMARY

Despite continuous improvements in onco-surgery, residual micro-tumors (microscopic residual disease—MRD) remain a significant problem. In many aggressive cancers, including head and neck squamous cell carcinoma (HNSCC), brain, lung and breast cancer, and sarcomas, what appears to be a complete tumor resection may leave MRD behind, often as small as tens of cancer cells, that later causes lethal recurrence. Clinical standards such as palpation and radiographic imaging are not sensitive enough to detect MRD. Pathological analysis of surgical margins, the only currently available MRD diagnostics, is slow, often inaccurate and not always available. As a result, surgeons routinely resect large margins of normal tissue to remove potential MRD. Unfortunately, this approach often fails, causes high morbidity and reduces patients' quality of life and eligibility. Post-operative radiation or chemoradiation therapies further increase the morbidity and treatment cost, and reduce patients' quality of life. Further, MRD often becomes highly resistant to radiation or chemotherapy resulting in poor survival. Similar needs of detecting cancer cells exist in in ex vivo tissue grafts and in veterinary medicine.

Today's diagnostic technologies cannot detect MRD in solid tissue in vivo with single cancer cell sensitivity and in real time. "Real Time" as used herein includes a broad ordinary meaning recognizable to one of ordinary skill in the art which includes the providing of output information responsive to the described processing of input data sufficiently quickly to allow a caregiver to affect the environment in which they are operating, using the output information as feedback. In any event, "Real Time" as used herein includes at least electronic processing delay times. As a result, those diagnostic technologies are limited in any reduction in local recurrence and improvement in overall survival for MRD-complicated surgeries. For example, while optical approaches improved cancer detection in vivo including intraoperative fluorescent and optical scattering diagnostics, they detect only relatively large tumors at the surface while MRD can be located deeper in tissue and can be of a microscopic size. Photoacoustic methods detect tumors in depths up to 10-20 mm although with limited sensitivity in solid tissue (>1000 cells), speed and specificity for intraoperative detection of MRD in a surgical bed. Radio-fluorescent methods can detect deeper tumors but are not sensitive enough for MRD detection. Multi-spectral optoacoustic tomography is used intraoperatively, but is not sensitive or fast enough to detect MRD (which can be represented by tens of cancer cells) in vivo in solid tissue in real time, and did not show a good surgical outcome in MRD applications. Furthermore, standard surgery often cannot remove MRD even when identified by frozen section pathology without causing too high morbidity because MRD infiltrates into critical organs.

In addition, a tumor micro-environment ("TME") could still exist after removal of cancer cells. Examples of TME include non-tumor targets that are biologically associated with a tumor, such as tumor blood vasculature and other components that are understood by one of ordinary skill in the art. Blood flow in the vasculature may cause tumor metastases of cancer cells or recurrence of tumor.

The present disclosure provides the ability to intraoperatively detect and precisely eliminate tumor and MRD in vivo in real time in resectable and in unresectable cases, and to intraoperatively detect and precisely eliminate TME, including tumor blood vasculature, either as a stand-alone or an intraoperative adjuvant treatment of residual tumor, to significantly improve the treatment outcome, treatment eligibility and quality of life for cancer patients and would reduce surgical morbidity. The present disclosure also provides the ability to detect cancer cells in tissue grafts and in veterinary medicine.

An objective of various embodiments of the present disclosure is to provide a plasmonic nanobubbles ("PNB"s)-guided in vivo and ex vivo diagnosis of tumors, microtumors, cancer cells, MRD and TME with high speed and cancer specificity in real time during a surgery. In some embodiments, the diagnosis can be applied to resectable tumors, unresectable tumors, or both or any specific target cells. In some embodiments, the diagnosis can be applied to TME. In some embodiments, the diagnosis can be applied to both tumor cells and TME. In accordance various embodiments disclosed herein, a process for noninvasive PNB-guided intraoperative detection of cancer cells in vivo comprises administering to a patient nanoparticles conjugated with cancer-specific antibodies (or other ligands) at a predetermined time prior to a diagnostic procedure; performing the diagnostic procedure comprising directing a first pulsed source of electromagnetic radiation having a predetermined level of energy against a first location on the patient to generate a first group of PNBs around the nanoparticles clustered in the cancer cells; detecting a first pressure pulse emitted by the first group of PNBs with an acoustic detector; transmitting a signal from the first pressure pulse to a signal processing unit to register a first acoustic time-response; and comparing the first acoustic time-response with a PNB-negative time-response to determine whether the first acoustic time-response meets a PNB-positive threshold. In accordance with various embodiments disclosed herein, the nanoparticles are capable of absorption and plasmonic conversion of electromagnetic radiation with wavelength in the near infrared region into the localized heat in and around plasmonic nanoparticle. In accordance with various embodiments disclosed herein, the electromagnetic radiation comprises a short laser pulse.

In some embodiments of the present disclosure, a system configured to noninvasively determine in real time a presence, a location and a depth of unwanted cells including cancer cells or microtumors or tumor-specific vasculature in tissue using PNBs during an intraoperative diagnostic procedure is provided. The system can include a plurality of bioconjugated nanoparticles configured to be administered to a patient at a predetermined time prior to a diagnostic procedure, a source of electromagnetic radiation configured to provide a plurality of pulses at a plurality of energy levels to tissue at a measurement site, an acoustic detector configured to output signals responsive to a plurality of pressure pulses emitted by PNBs from at least some of the bioconjugated nanoparticles in the cancer cells, and a signal processor configured to receive said signals or one or more pre-processed signals responsive to said signals and configured to process said signals or said one or more pre-processed signals. The bioconjugated nanoparticles can comprise a plurality of nanoparticles and a plurality of cancer-specific or tumor-associated vasculature-specific ligands configured to attach to and cluster in said unwanted cells. The processing can include determining a first acoustic time-response from said signals or said pre-processed signals corresponding to pulse of said source at a first energy level, comparing said first acoustic time-response with a PNB-negative time-response, when said comparison is negative, outputting notification indicia usable by a caregiver to determine the presence of said unwanted cells at a first depth in said tissue at said measurement site, and when said presence of said cancer cells is determined, additionally determining another acoustic time-response from said signals or said pre-processed signals corresponding to pulses of said source at an increased energy level. The increased energy level can be configured to cause said pulses of said source to reach tissue at an increased depth. The processing additionally can include comparing said another acoustic time-response with said PNB-negative time-response, when said comparison is negative, additionally outputting notification indicia usable by said caregiver to determine the presence of said unwanted cells at the increased depth in said tissue at said measurement site, and repeating said additionally determining, comparing and outputting until said additional comparing is positive.

In some embodiments of the present disclosure, a noninvasive real-time process to determine a presence, a location and a depth of cancer in tissue using plasmonic nanobubbles ("PNBs") is disclosed. The process can include administering bioconjugated nanoparticles to a patient, the bioconjugated nanoparticles comprising a plurality of nanoparticles and a plurality of bonded cancer-specific or tumor-associated vasculature-specific ligands; emitting with a laser source a laser pulse at an energy to tissue at a measurement site of said patient to generate a group of PNBs; detecting with a detector one or more pressure pulses from said group of PNBs; transmitting to a signal processor signals responsive to said detected sounds; processing with said signal processor said signal, said processing including determining a time-response; comparing the time-response to a threshold; when said time-response is less than said threshold, outputting indicia to a monitor reviewed by a caregiver, said indicia usable to conclude cancer cells exist in said tissue at a depth; and when said time-response is less than said threshold, increasing said energy of said laser pulse and repeating said detecting, transmitting, and said processing to determine whether said cancer cells exist in said tissue at an increase of said depth.

In some embodiments of the present disclosure, a system usable in the resection of cancer cells or microtumors that improves therapeutic efficacy and reduced morbidity of standard surgery is disclosed. The system can include a source of electromagnetic radiation, a PNB probe configured to irradiate tissue of a patient including bioconjugated nanoparticles to produce PNBs in said tissue, a detector configured to output a signal responsive to pressure pulses of said PNBs, and a signal processor configured to process information responsive to said signals to generate an output usable by a clinician to determine whether to resect portions of said tissue defined by a footprint of said PNB probe. Said source can be configured to, when needed, provide said PNB probe increasing levels of radiation pulses to reach increasing depths of said tissue. The system can further comprise a surgical apparatus configured to position or house said PNB probe. Said surgical apparatus can comprise a robotic surgical arm. Said surgical apparatus can comprise a laparoscopic tool. Said surgical apparatus can comprise an endoscope.

In some embodiments of the present disclosure, a process that guides a surgeon in the resection of cancer cells or microtumors is provided. The process can include irradiating with a PNB probe having a source of electromagnetic radiation tissue of a patient including bioconjugated nanoparticles to produce plasmonic nanobubbles ("PNB") in said tissue, outputting from a detector a signal responsive to pressure pulses of said PNBs, processing with a digital signal processor information responsive to said signals; and generating an output usable by a surgeon to determine whether to resect portions of said tissue defined by a footprint of said PNB probe. Said source can be configured to, when needed, provide said PNB probe increasing levels of radiation pulses to reach increasing depths of said tissue. Said irradiating, outputting, processing, and generating can repeat with each resection of said portion of said tissue to monitor outcome of a previous resection. Said generating an output can comprise generating said output directing said surgeon to relocate said PNB probe to a different portion of said tissue. Said generating an output can comprise generating said output directing said surgeon to resect more of said portion even when said processing does not indicate detection of said PNBs. Said generating an output can comprise generating said output directing said surgeon to probe deeper into said portions of said tissue. Probing deeper can comprise said irradiating, outputting, processing, and generating using an increased energy of said radiation. Said processing using said increased energy can comprise comparing a peak-to-peak amplitude of said signals to a cancer-free signal. Said processing using said increased energy can comprise determining a time delay between an activation of said source and a detection of said pressure pulses and comparing said delay with known delay information. Said irradiating using said increased energy can comprise pulsing said source at a laser pulse fluence of between 10 and 120 $mJ/cm^2$. Said pulsing said source at said laser pulse fluence can comprise pulsing said source at about 60 $mJ/cm^2$. Said irradiating can comprise pulsing said source for a duration not exceeding about 100 ps. Said irradiating can comprise pulsing said source for a duration of about 30 ps. Said energy levels can exceed a PNB generation threshold.

In some embodiments of the present disclosure, a system for eliminating non-operable cancer cells or tumor-specific vasculature to improve the outcome in unresectable cases with a PNB "nano-surgery" mode is disclosed.

In some embodiments of the present disclosure, a system for eliminating non-operable unwanted cells including one or more of cancer cells or tumor-associated vasculature is disclosed. The system can comprise a source of electromagnetic radiation, a PNB probe configured to irradiate tissue of a patient including bioconjugated nanoparticles to produce plasmonic nanobubbles ("PNBs") in said tissue, said source configured to provide said PNB probe increasing levels of radiation pulses including increasing detection-level radiation and increasing destruction-level radiation, a detector configured to output a signal responsive to pressure pulses of said PNBs, and a signal processor configured to process information responsive to said signals and to increase the level of the laser pulse energy or fluence from detection-level radiation to destruction-level radiation to selectively destroy said unwanted cells by a mechanical impact generated from an explosive effect of the PNBs. The signal processor can be further configured to increase the detection-level radiation, when needed, and correspondingly to increase the destruction-level radiation. The signal processor can be further configured to monitor destruction of said cancer cells through a peak-to-peak amplitude of an output of said signal processor. The signal processor can be further configured to cause said increase until said pressure pulses of said PNBs indicate no further cancer cells in said tissue. The detection-level radiation can exceed a PNB generation threshold. The detection-level radiation can be between 10 and 120 mJ/cm$^2$ for an about 25 ps pulse. The detection-level radiation can be 60 mJ/cm$^2$ for an about 25 ps pulse. Said destruction-level radiation is sufficient to generate PNBs with a size exceeding a cancer cell damage threshold. At least some PNBs of the system can be of a size exceeding a cancer cell damage threshold and some PNBs can be of a size below a cancer damage threshold after said destruction-level radiation. The destruction-level radiation can be between 40 and 400 mJ/cm$^2$ for an about 25 ps pulse. The destruction-level radiation can be 120 mJ/cm$^2$ for an about 25 ps pulse. The source can be configured to provide said radiation pulses with a duration not exceeding about 100 ps. The source can be configured to provide said radiation pulses with a duration of about 30 ps. The signal processor can be further configured to generate an output directing a surgeon to relocate said PNB probe to a different portion of said tissue. The signal processor can be further configured to generate an output directing a surgeon to increase the level of the laser pulse energy or fluence from said detection-level radiation to said destruction-level radiation even when said output does not indicate detection of said PNBs. The signal processor can be further configured to generate an output directing a surgeon to probe deeper into said portions of said tissue. Probing deeper can comprise increasing said detection-level radiation. The bioconjugated nanoparticles can be configured to produce PNBs in cancer cells. The bioconjugated nanoparticles can be configured to produce PNBs in tumor-associated vasculature. The bioconjugated nanoparticles can be configured to produce PNBs in one or more of cancer cells or tumor-associated vasculature, wherein a first group of bioconjugated nanoparticles can be configured to attach to and cluster in said cancer cells and a second group of bioconjugated nanoparticles can be configured to attach to and cluster in said tumor-associated vasculature. The first and second groups of bioconjugated nanoparticles can be the same. The first and second groups of bioconjugated nanoparticles can be different.

In some embodiments, a cancer detection system configured to noninvasively determine a presence of unwanted cancerous material in tissue using plasmonic nanobubbles ("PNBs") is disclosed, said cancer detection system returning post-electronic processing results to an operator at least at each measurement site during a cancer detection procedure. Said cancer detection system can comprise a plurality of bioconjugated nanoparticles configured to be administered to a patient at a predetermined time prior to said cancer detection procedure, the bioconjugated nanoparticles comprising a plurality of nanoparticles and a plurality of cancerous material-specific ligands configured to attach to and cluster in said unwanted cancerous material; a source of electromagnetic radiation configured to provide a plurality of radiation pulses at a plurality of energy levels to said tissue at said measurement site; and an acoustic detector configured to output signals responsive to a plurality of pressure pulses emitted by PNBs from at least some of the bioconjugated nanoparticles when said tissue includes said unwanted cancerous material; and one or more signal processors operably communicating with said acoustic detector and configured to receive said output signals or one or more pre-processed signals responsive to said signals, configured to electronically process said signals or said one or more pre-processed signals, and configured to notify said operator with a result of said processing at each measurement site, said processing including determining a first acoustic time-response responsive to said signals or said pre-processed signals corresponding to one or more of said pulses of said source at a first energy level; comparing said first acoustic time-response with a PNB-negative time-response to determine a detection of the PNBs; and when a sufficient amount of said presence is determined, returning a positive result for said presence of said unwanted cancerous material. The system can be configured to noninvasively determine a depth of unwanted cancerous material, wherein said one or more signal processors electronically process said signals or said one or more pre-processed signals. The processing can further include determining another acoustic time-response responsive to said signals or said pre-processed signals corresponding to one or more of said pulses of said source at an increased energy level, the increased energy level configured to cause said pulses of said source to reach tissue at an increased depth; comparing said another acoustic time-response with said PNB-negative time-response; when said comparison is negative, additionally returning a positive result for said presence of said unwanted cancerous material at the increased depth in said tissue at said measurement site; and repeating said determining using said increasing energy levels, comparing and returning until said additional comparing is positive and said one or more processors return a negative result for said unwanted cancerous material at the increased depth. Said cancerous material can include cancer cells, cancerous microtumors, or cancerous tumor associated vasculature. Said source can provide said plurality of said pulses, at least some of said pulses provided at wavelengths between about 600 and about 1,500 nm. Said source can provide said plurality of said pulses, at least some of said pulses provided at a wavelength of about 782 nm. Said source can provide said plurality of said pulses, at least some of said pulses having a duration not exceeding about 100 ps. Said duration can be about 30 ps. The system can further comprise a medical apparatus configured to position or house said source. Said medical apparatus can comprise a robotic arm. Said medical apparatus can comprise a laparoscopic tool. Said medical apparatus can comprise an endoscope. The cancerous material-specific ligands can comprise an antibody. The antibody can comprise different antibodies.

In some embodiments, a noninvasive process to determine cancer in tissue using plasmonic nanobubbles ("PNBs") is disclosed. Said process can comprise administering bioconjugated nanoparticles to a patient, the bioconjugated nanoparticles comprising a plurality of nanoparticles and a plurality of bonded cancer-specific or tumor-associated vasculature-specific ligands; emitting from a laser source a laser pulse at an energy to tissue at a measurement site of said patient; detecting with a detector one or more pressure pulses from a group of PNBs, if any, responsive to said laser pulse; electronically processing with one or more signal processors, one or more signals responsive to said detecting, said processing can include electronically determining a time-response; electronically comparing the time-response to a threshold; and when said time-response is greater than said threshold, outputting indicia to a monitor, said indicia usable to conclude one or more of cancer cells or tumor-specific vasculature exist in said tissue. When said time-response is greater than said threshold, the process can further comprise increasing said energy of said laser pulse and repeating said detecting, transmitting, and said processing to determine whether said cancer cells or tumor-specific vasculature exist in said tissue at an increase of said depth. Said repeating can terminate when said time-response is less than said threshold. When said time-response is greater than said threshold, the process can further comprise generating an output usable by a surgeon to determine whether to resect portions of said tissue defined by a footprint of said PNB probe. Said emitting, outputting, processing, and generating can repeat with each resection of said portion of said tissue.

BRIEF DESCRIPTION OF THE DRAWINGS

The drawings and following associated descriptions are provided to illustrate embodiments of the present disclosure and do not limit the scope of the claims. Corresponding numerals indicate corresponding parts.

FIG. 2A-2D illustrate the delivery and clustering of gold nanoparticles, generation and detection of PNB in cancer cells in vivo.

FIG. 10A illustrates an exemplary influence of tumor-specific antibodies on biodistribution of gold nanoparticles.

FIG. 10B illustrates an exemplary influence of tumor size on accumulation of gold nanoparticles in a tumor.

FIGS. 12A-C illustrate exemplary simultaneously detected optical scattering and acoustic time-responses to a single laser pulse applied to individual gold-pre-treated and intact HNSCC cancer cells in transparent media.

FIGS. 12D-F illustrate exemplary detected acoustic time-responses to a single laser pulse applied to individual HNSCC cancer cells in a piece of chicken breast after injecting gold pre-treated cancer cells one by one.

DETAILED DESCRIPTION

Figure 2:
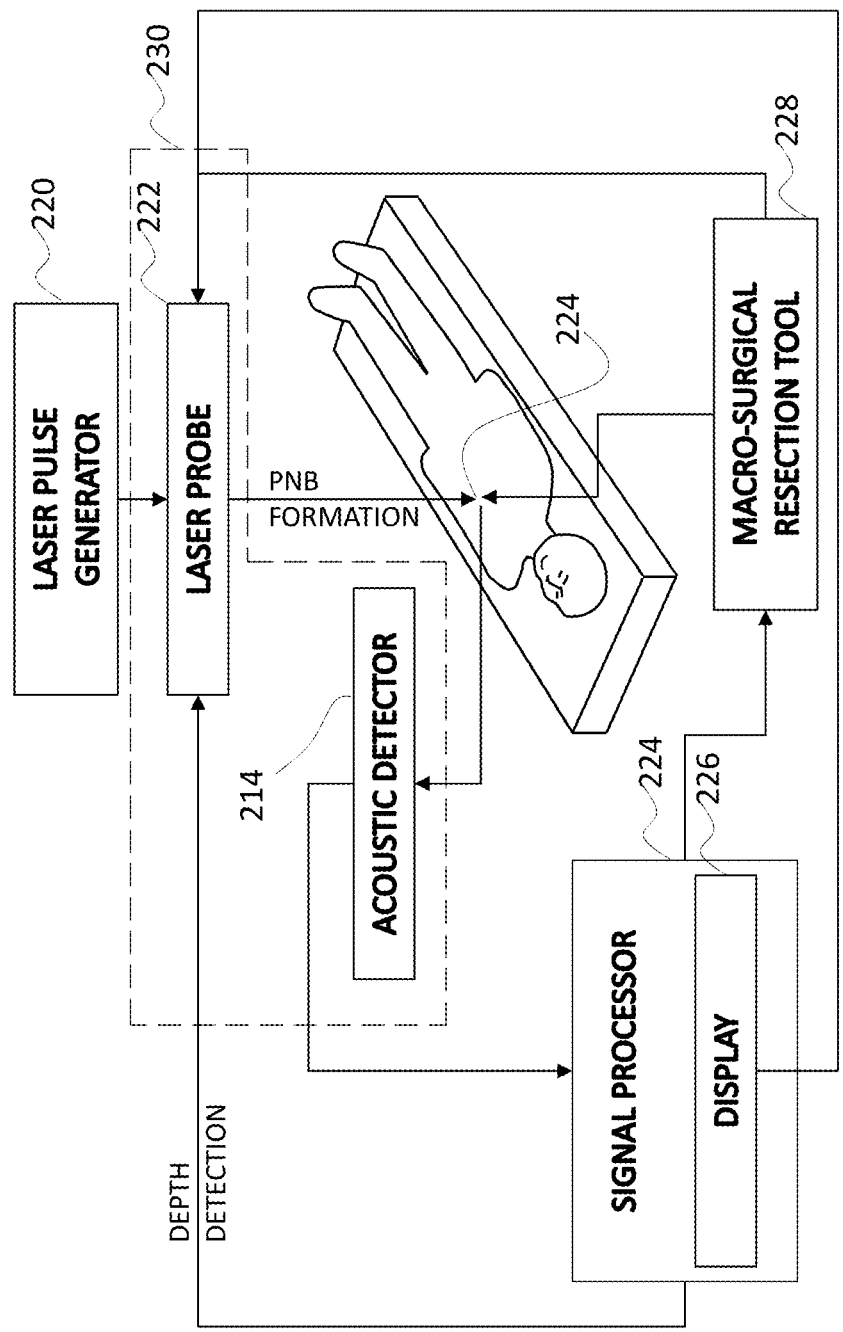
FIG. 2 illustrates a block drawing of a cancer cells detection and elimination system in accordance with an embodiment of the disclosure.

Aspects of the disclosure are provided with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit scope of the disclosure herein, which is instead defined by the claims following this description.

The term "energy" in this disclosure includes its broad ordinary meaning understood by an artisan, and also is shorthand for "fluence," which has its broad ordinary meaning understood by an artisan to include energy per area squared.

Combining the intraoperative detection of single cancer cells in a surgical bed, real-time elimination of MRD and prediction of the surgical outcome is the ultimate desire for surgical oncologists. Embodiments of this disclosure can achieve this and other multi-functionality through a PNB technology with high cancer cell sensitivity, specificity, speed and translational potential.

The application of plasmonic nanobubbles (PNBs) technology to target cancer cells ex vivo has been described, for example, in U.S. Pat. No. 7,999,161 to Oraevsky et al., the contents of which are incorporated herein by reference in their entirety. FIGS. 1A-1C illustrate known principles of interactions of bioconjugated nanoparticles 100 with an isolated normal cell 102 and an isolated tumor cell 104. Nanoparticles 100 which are capable of absorption and plasmonic conversion of energy from a source of electromagnetic radiation are covalently conjugated with cancer-specific monoclonal antibodies in order to target receptors 106 found on a surface of the tumor cell, for example, an epidermal growth factor receptor, but not found on a surface of the normal cell. As a result, when introducing the bioconjugated nanoparticles 100 to the tumor cell 104, the nanoparticles 100 are adsorbed onto on the surface of the tumor cell via the receptors and eventually form nanoparticle clusters 108 inside the tumor cell. In contrast, the nanoparticles 100 are seldom taken up by the normal cell 102 due to lack to cancer-specific receptors on its surface, and no cluster is formed in the cytoplasm of the normal cell. Applying a pulsed source of electromagnetic radiation, such as a laser pulse 110, to the cancer cell 104 containing the nanoparticle clusters 108 can cause a nanobubble 112 to be formed from the rapid evaporation of liquid around the overheated cluster 108 due to the absorption and plasmonic conversion of the laser pulse energy, whereas the same laser pulse energy is not sufficient to excite the few isolated nanoparticles 100 that are occasionally taken up by the normal cell 102. The rapid expansion and collapse of the vapor nanobubble 112 can identify the existence of tumor cell 104, can guide resection thereof, and can cause mechanical impact on and can destroy the tumor cell 104.

Cancer Cell Detection and Elimination

FIG. 2 illustrates a schematic drawing of a cancer cells detection and elimination system in accordance with an embodiment of the disclosure. The system will be described below in detail in connection with the descriptions of FIGS. 2A-2D and FIGS. 3-6.

Figure 8B:
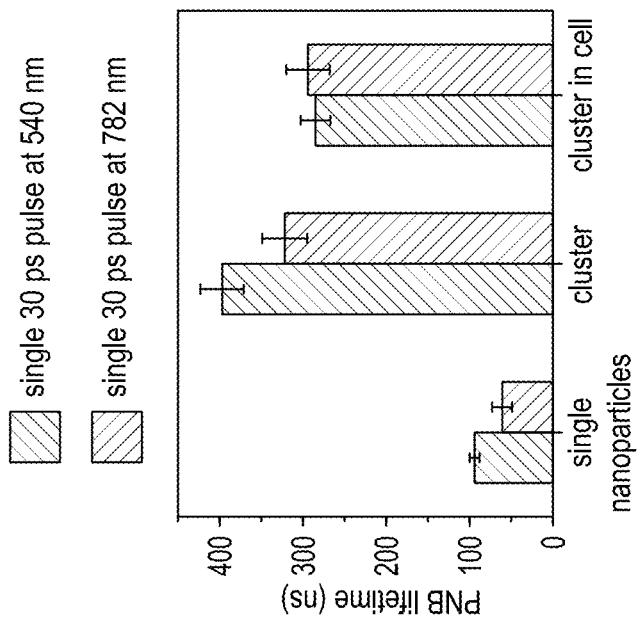
FIG. 8B illustrates an exemplary comparison of PNB lifetime of the gold nanoparticles in FIG. 8A under non-stationary optical excitation.
Figure 8A:
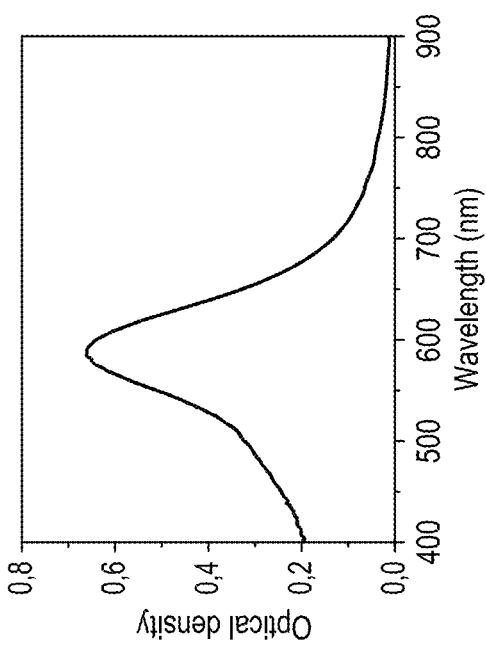
FIG. 8A illustrates an exemplary stationary optical excitation spectrum showing photothermal efficacy of gold spherical nanoparticles conjugated to Panitumumab.

FIGS. 2A-2D illustrate detection of cancer cells in vivo. FIG. 2A illustrates administration of nanoparticle conjugates 200 into the patient's body including normal tissue 201 having normal cells 202, and tumor tissue 203 having cancer cells 204. As electromagnetic radiation in the visible region can have difficulty penetrating solid tissue, nanoparticles that demonstrate high optical absorbance in the near-infrared (NIR) range, such as a laser pulse 210, can be used. Nanoparticles that have low toxicity to patients as well as the ability to be excited by an NIR pulse are suitable candidates for nanobubble generation. At least partially metallic nanoparticles, such as gold nanoparticles, can have desirable biosafety (see Example 3 below), but have a peak of optical absorbance in the visible light range if under a stationary source of electromagnetic radiation (FIG. 8A). Nevertheless, as shown in FIG. 8B and explained in greater detail below in Example 2, off-resonant excitation of such nanoparticles can be achieved by using non-stationary pulsed laser energy with duration in the range of picoseconds. The duration of the pulse can be between about 1 ps to 1000 ps. For example, it would be advantageous to keep the duration of the pulse below 100 ps, although an artisan will recognize from the disclosure herein other durations. Using gold as an example (FIGS. 2A-2D), gold nanoparticles used for making gold colloid conjugates 200 can be between 10 to 300 nm in the largest dimension and can be of any shape. In some embodiments, the gold nanoparticles can be 60 nm spheres. To form clusters 208 in vivo, gold nanoparticles 200 conjugated with any cancer-specific antibodies 206 or other ligands to recognize cancer cells, such as Panitumumab, can be systemically administered. In some embodiments, the gold conjugate can be administered intravenously at a dose that results in negligible short-term and long-term toxicity. The gold conjugate can be administered in the amount of between about 0.1 mg/kg to about 20 mg/kg body weight, or between about 1 mg/kg to about 40 mg/kg body weight. In some embodiments, the gold conjugate can be administered in the amount of about 4 mg/kg body weight. The gold conjugate can be administered at between about 1 hour to about 36 hours prior to a diagnostic procedure or an onco-surgery. In some embodiments, the gold conjugates can be administered at least about 24 hours prior to a diagnostic procedure or an onco-surgery. Alternatively, the bioconjugated nanoparticles can be locally injected prior to apply a laser pulse. Example 2 below provides in greater detail several mechanisms for forming in vivo intracellular clusters of gold colloids as PNB sources. As described above and shown in FIGS. 2B and 2C, the gold conjugates 200 are attached onto a surface of the cancer cells, but are seldom attached onto a surface of a normal cell.

Figure 2B:
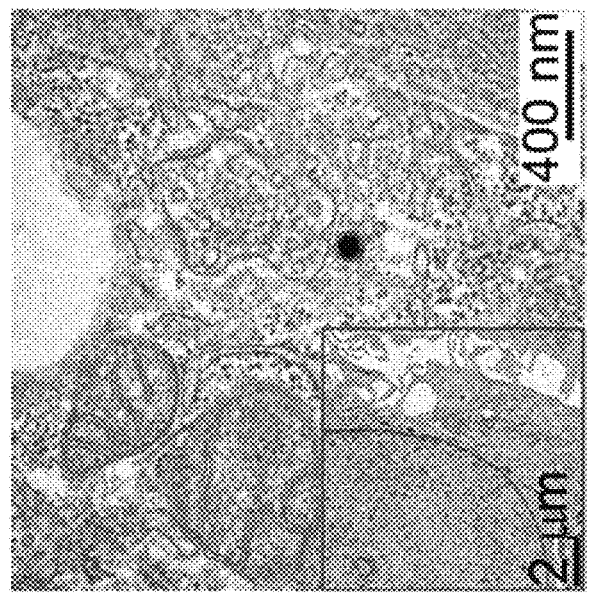
Figure 2B:
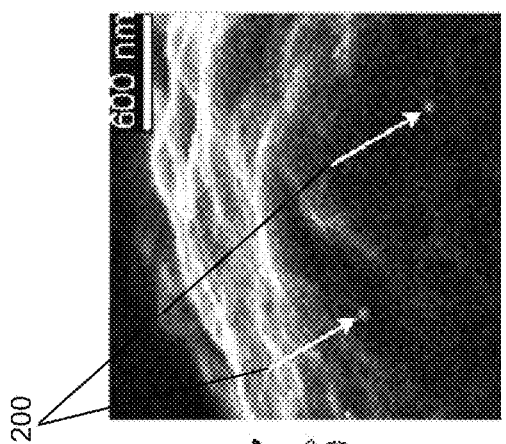
Figure 2B:
Figure 2B:
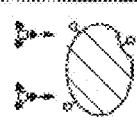
Figure 2C:
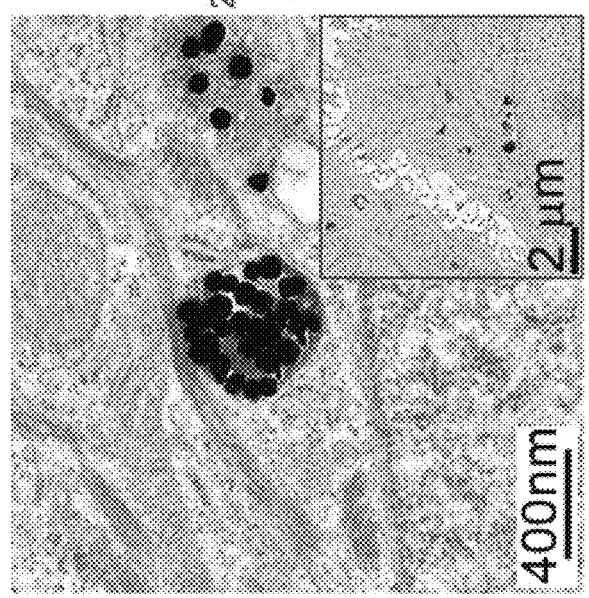
Figure 2C:
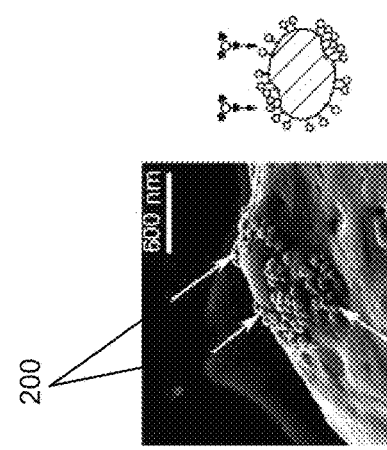
Figure 2C:
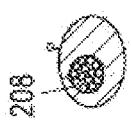
Figure 2C:
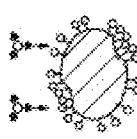
Figure 2D:
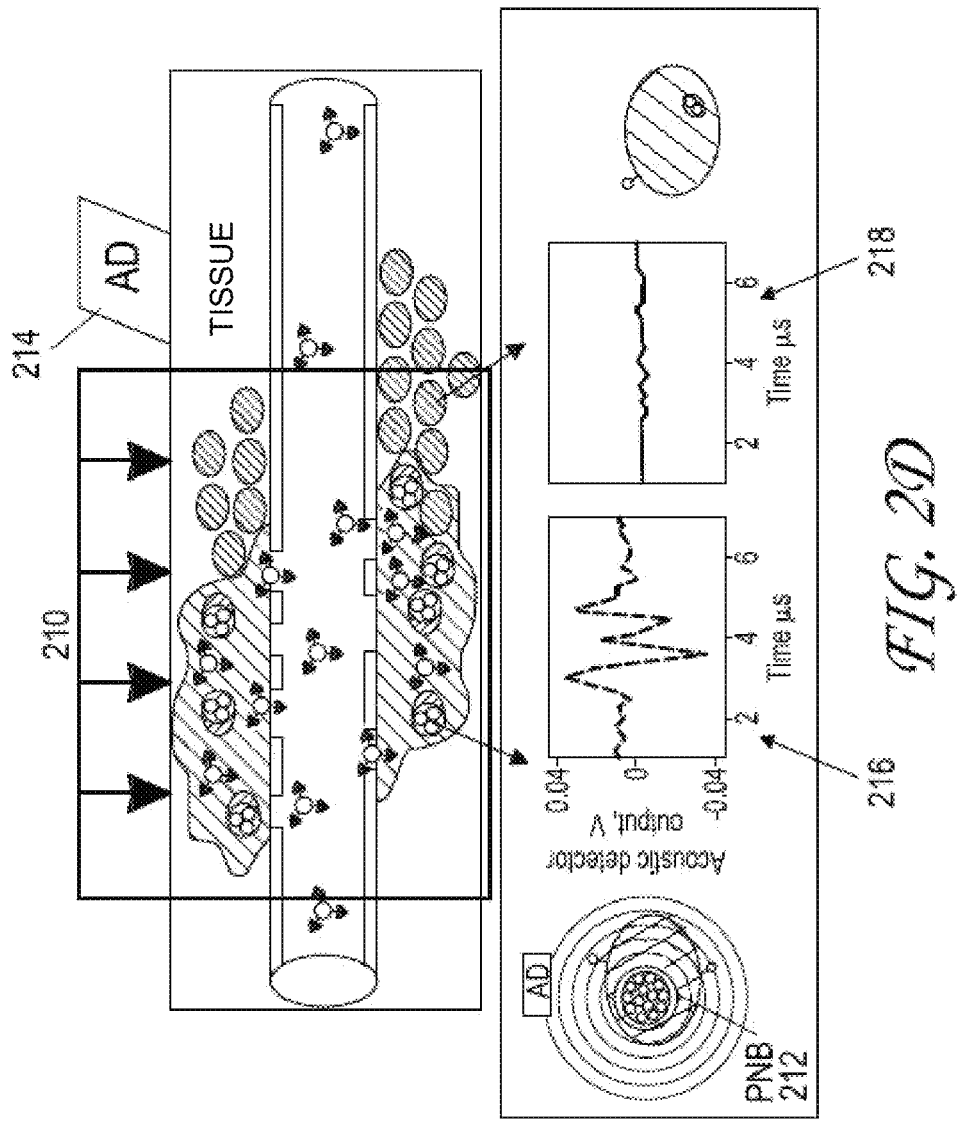

Turning to FIG. 2D, to generate PNBs, a pulsed source of electromagnetic radiation, such as a laser probe 222 can emit a single laser pulse 210 generated by a laser pulse generator 220 with wavelength between 600 nm and 1,500 nm and fluence below the PNB generation threshold for single nanoparticles but above the PNB generation threshold for their large clusters. The laser pulse can be directed against a location 224 on a patient (FIG. 2) having both normal tissue 201 and a tumor 203. In some embodiments, PNB generation threshold can be 10-15 mJ/cm$^2$ for gold-pretreated HNSCC cells and single near-infrared laser (NIR) pulses (782 nm, 30 ps) can be used for PNB generation. An expanding and collapsing PNB 212 (FIG. 2D) can report a cancer cell by emitting a pressure pulse, which can be detected acoustically with a wide variety of detectors, such as an acoustic detector 214. The acoustic detector 214 can be any detector capable of converting a pressure pulse into optical or electrical signal, including but not limited to piezo-, fiber optical-, waveguide-based sensors of various shape and dimension, which can be applied locally to detect said pressure pulse emitted by PNB. In some embodiments, the acoustic detector 214 can include a broadband ultrasound sensor of a needle type integrated with a pre-amplifier and can be further connected to an external power supply with a second pre-amplifier. In one embodiment of the present invention, the laser probe 222 and the acoustic detector 214 can optionally be incorporated into a single probe device 230, as illustrated in FIG. 2.

With continued reference to FIG. 2D, The output of the detector or of the second pre-amplifier can be connected to a signal processing unit 224, such as a digital oscilloscope, analog-to-digital converter, other electronic devices or other types of processors, to register an acoustic time-response 216 to a single laser pulse. The acoustic time-response 216 can be displayed on a display screen 226 of the signal processor (FIG. 2). This time-response 216 from the location 224 where cancer cells might be present (the test) can be compared with a time-response previously obtained from a cancer-free location (the reference 218). As shown in the graphs in FIG. 2D, the test time-response 216 shows spikes, indicating the presence of cancer cells 204 at that location, whereas the reference time-response 218 appears relatively flat, indicating a cancer-free location. In some embodiments, the test time-response 216 and the reference time-response 218 can be placed side by side. In some embodiments, the test time-response 216 and the reference time-response 218 can be superposed on each other. An artisan will recognize from the disclosure herein other forms of the display of test time-response 216 and the reference time-response 218. The exemplary diagnostic process shown in FIGS. 2A-2D can be used at a diagnostic stage or during an onco-surgery, which will be discussed in greater detail below. The exemplary diagnostic process described herein can have the advantage of providing a surgeon during an onco-surgery with real time in vivo diagnosis. The laser pulse generator 220 can be switched on within milliseconds during a surgery. In addition, no time-consuming signal reconstruction is required (unlike photoacoustic processes) because the PNB signal amplitude is directly read from the pressure pulse signal. Single cancer cell sensitivity of the PNBs in the present disclosure (compared to that of photoacoustic, multi-spectral optoacoustic tomography and optical diagnosis processes) can result from one or more of the following: (1) the high efficacy of PNB generation by nanoparticle clusters, 10-100 fold higher than single nanoparticles, (2) much higher pressure produced by the rapid expansion and collapse of a vapor nanobubble than the thermo-elastic effect in nanoparticles employed by photoacoustic diagnosis processes, and (3) using the non-stationary PNB mechanism with a short laser pulse which provides efficient excitation of clinically safe colloidal nanoparticles with deep tissue-penetrating near-infrared laser pulse, a combination not possible in photoacoustic diagnosis processes or under stationary optical excitation. Although the diagnostic sensitivity may decrease with the tissue depth, diagnosis processes in accordance with an embodiment of this disclosure can still be capable of detecting even just about 30 residual cancer cells or less at about 4 mm or deeper, which can be equivalent to tumors below 50 um size. The high cancer cell specificity of the PNBs is based not only on the antibody-directed targeting of nanoparticles as in other diagnosis processes, but also on the cluster-threshold mechanism of PNB generation. This, in turn, can also significantly reduce the nanoparticle dose to about 1-10% of the doses employed by photoacoustic, photothermal or computer tomography diagnosis processes. Such a low nanoparticle dose can be safely delivered to the tumor. The clustering of nanoparticle conjugates with antibodies in cancer cells can generate PNBs substantially only in cancer cells with near-infrared laser pulses of low energy.

Figure 3A:
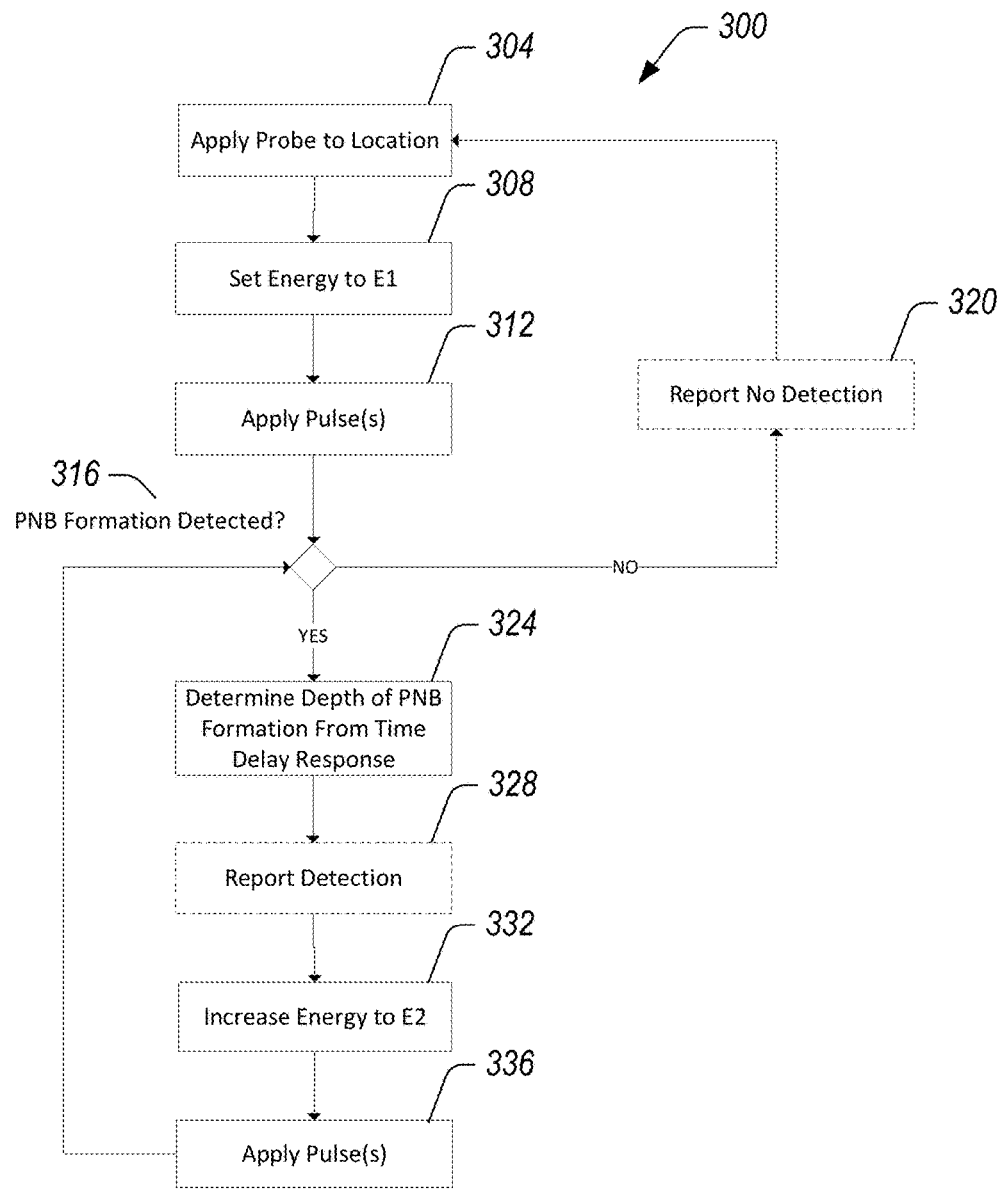
FIG. 3A illustrates an embodiment of an exemplary diagnosis process that includes a determination of a depth of cancer cells in tissue.

FIG. 3A illustrates an embodiment of an exemplary diagnosis process 300 that includes a determination of a depth of cancer cells in tissue. The process of PNB generation and detection using single pulses at a single level of laser fluence can be sufficient for diagnosis of superficial tumor or MRD in surgical margins within about 1-2 mm depth (which is better than optical processes whose sensitivity is limited by tens of micrometers of solid tissue depth for microscopic tumors or single cancer cells). To allow laser pulses to penetrate to deeper tissues, after a first laser pulse is applied to a location and a signal is read, subsequent laser pulses of increasing energy can be applied to the same location to read signals at increasing tissue depths.

For example, a plurality of laser pulses can be applied in succession at the same location on a patient, each pulse having a higher level of energy than a previous pulse to reach deeper in the tissue. As shown in FIG. 3A, a laser probe can be applied to a location on a patient at step 304. The location can be a location the probe was previously applied to, or a new location. At step 308, the laser energy can be set at E1, which can be a detection-level energy. One or more pulses of energy E1 can be applied at step 312. Applying a plurality of pulses of the same energy can ensure more thorough detection of tumor cells at substantially the same depth than a single pulse at that energy level. For example, E1 can be about 10-15 mJ/cm$^2$ in the case of gold pretreated HNSCC cells. At decision step 316, a hardware processor can determine if PNB formation has been detected in manners described herein. For example, the hardware processor can receive output of an acoustic sensor and analyze a time-delay response as described above. If PNB formation was not detected, the processor can optionally generate a report that no PNB formation or tumor cells were detected at step 320. If a positive time-delay response has been detected, the processor can determine a depth of the PNB formation, which can indicate a depth of the tumor cells or tumor-associated vasculature, from the time-delay response at step 324. The processor can optionally generate a report of detection at step 328. In some embodiments, the report of detection can include PNB formation, existence of tumor cells, or existence of tumor-associated vasculature. In some embodiments, the report of detection can include depth of PNB formation, tumor cells, or tumor-associated vasculature. At step 332, the laser energy can be set to E2, which is higher than E1. The laser energy level can be set by the processor or manually be a caregiver. Laser pulse(s) of energy E2 can be applied to the same location at step 336 in an attempt to reach tissue at a greater depth than a laser pulse of energy E1. The laser pulse(s) can be applied by the processor or manually by a caregiver.

The process as illustrated in FIG. 3A can be reliably applied since the PNB generation threshold remains substantially the same at any depth. This is because the threshold at a specific laser wavelength is determined only by the size of the nanoparticle cluster. Furthermore, cancer cells at a more superficial level of the tissue would have already responded with PNBs to previous laser pulses and the nanoparticle clusters would have been mechanically scattered by those previously-formed PNBs. In addition, single scattered nanoparticles cannot generate PNBs under the same fluence or energy level as efficiently as nanoparticle clusters. As a result, each laser pulse of higher energy can generate PNBs deeper in the tissue and for each time-response that is PNB-positive, a time delay of the laser pulse can be recorded. If a certain location in the patient's body is known or suspected to have cancer cells, multiple successive pulses, each with an increasing energy than the preceding pulse, can be applied at the same location on a patient, according to the process illustrated in FIG. 3A, until an acoustic time-response below the PNB-positive threshold is detected, indicating a cancer-free zone has been reached. The laser probe can then be directed to a new location on a patient. One of ordinary skill in the art will recognize from disclosure herein important diagnostic information relating to a size and/or a depth of the tumor from any one of, combination of any two of, or all three parameters, which can include a peak-to-peak amplitude of the PNB signal, the time delay relative to the time point of the laser pulse, and the laser pulse fluence (energy per square cm).

This multi-pulse diagnosis process can be used at a diagnostic stage or intraoperatively during an onco-surgery. At the diagnostic stage, the multi-pulse diagnosis process can inform a clinician if the tumor is superficial or subcutaneous, potentially influencing the adoption of treatment modes. In a surgery, PNBs can not only detect deeper tumors, but also indicate the depth of the tumor, thus helping a surgeon to plan the follow-up resection. Furthermore, the PNB generation depth via the time-delay from the laser pulse can be independently monitored in addition to the peak-to-peak amplitude of the PNB spike in the time-response (obtained under specific level of the laser fluence). This diagnosis process also does not require time-consuming signal reconstruction (unlike photoacoustic or tomographic diagnostic processes) because both the PNB signal amplitude and time-delay can be directly read from the primary signal (time-response). FIGS. 4A-4C illustrate an exemplary embodiment of the diagnosis process shown in FIG. 3A. As shown in FIG. 4A, two successive laser pulses, Pulses 1 and 2 can be directed at the same location. Pulse 1 can have an energy E1 and be configured to reach gold clusters, and therefore cancer cells at a depth of 1 mm. The response to the cancer cell at the depth of 1 mm can have a time delay $t_1$. Pulse 2 can have an energy E2, where E2 is greater than E1, and be configured to reach cancer cells at a depth of 3 mm. The response to the cancer cell at the depth of 3 mm can have a time delay $t_2$.

In some embodiments, the laser pulse can have a constant fluence or energy level during a diagnosis or PNB detection procedure. One or more of the following can be varied for probing cancer cells at different depths when the laser pulse is kept at the same fluence or energy level: cluster size of the nanoparticles, type of cancer-specific ligands, or a combination thereof. Cluster size of the nanoparticles formed inside the cancer cells can be controlled by varying one or more of nanoparticle composition (solid or hollow), shape, size, or a combination thereof. In this application, the size of nanoparticle may vary from about 10 nm to about 400 nm. The nanoparticles may have various shapes, including but not limited to a solid sphere, a hollow sphere, solid or hollow structures of different shape such as cube, pyramid, or irregular shape. The nanoparticles can be gold nanoparticles, or of other suitable materials, which may be chosen by a skilled artisan in view of the disclosure herein. The cancer-specific ligands in this disclosure can include but are not limited to antibody, peptide(s), aptamer(s), or any molecular ligand.

In some embodiments, a plurality of acoustic detectors can be placed at various locations around the tissue. If cancer cells are present, time-responses from the plurality of acoustic detectors can be used to provide estimated location of the cancer cells in a two-dimensional or three-dimensional manner. For example, a depth and lateral positions of the cancer cells can be estimated.

The threshold fluence for detecting the PNB can depend on the tumor and nanoparticle properties. The value of the detection threshold fluence may also be affected by levels of aggressiveness of the cancer cells. For example, a low laser pulse threshold fluence of PNB generation and detection can indicate highly aggressive cancer cells, whereas an increased threshold fluence can indicate less aggressive cells, including indolent cancer cells. This is because highly aggressive cancer cells can have a greater amount of energy available for internalizing the bioconjugated nanoparticles and therefore can form large clusters of nanoparticles inside the highly aggressive cancer cells. In contrast, less aggressive or indolent cancer cells may form medium-sized nanoparticle clusters inside these cells, and normal or non-cancer cells may only non-specifically internalize single nanoparticles. As described above, the PNB size, measured by its lifetime, can be determined by the nanoparticle cluster size. Therefore, a lower laser pulse fluence can generate a detectable PNB in the highly aggressive cancer cells. A higher laser pulse fluence can generate a detectable PNB in the less aggressive cancer cells. And a still higher laser pulse fluence can generate a detectable PNB in the normal cells. Additional details of the relationship of PNB generation threshold fluence and the aggressiveness of the cancer cells are described in Lukianova-Hleb, Ekaterina Y., et al., "On-demand intracellular amplification of chemoradiation with cancer-specific plasmonic nanobubbles," Nature medicine 20.7 (2014): 778-784, the entirety of which is incorporated herein by reference.

The lower PNB generation threshold fluence of highly aggressive cancer cells than less aggressive cancer cells can provide an advantage of using PNBs for cancer detection and removal. Specifically, in traditional forms of cancer treatment, such as chemotherapy, the highly aggressive cancer cells can be more resistant to the treatment than the less aggressive cancer cells. In the embodiments of the disclosure herein, the highly aggressive cancer cells are more susceptible to detection and destruction (see below) because a lower laser pulse fluence is required to generate PNBs in the highly aggressive cancer cells.

Figure 3B:
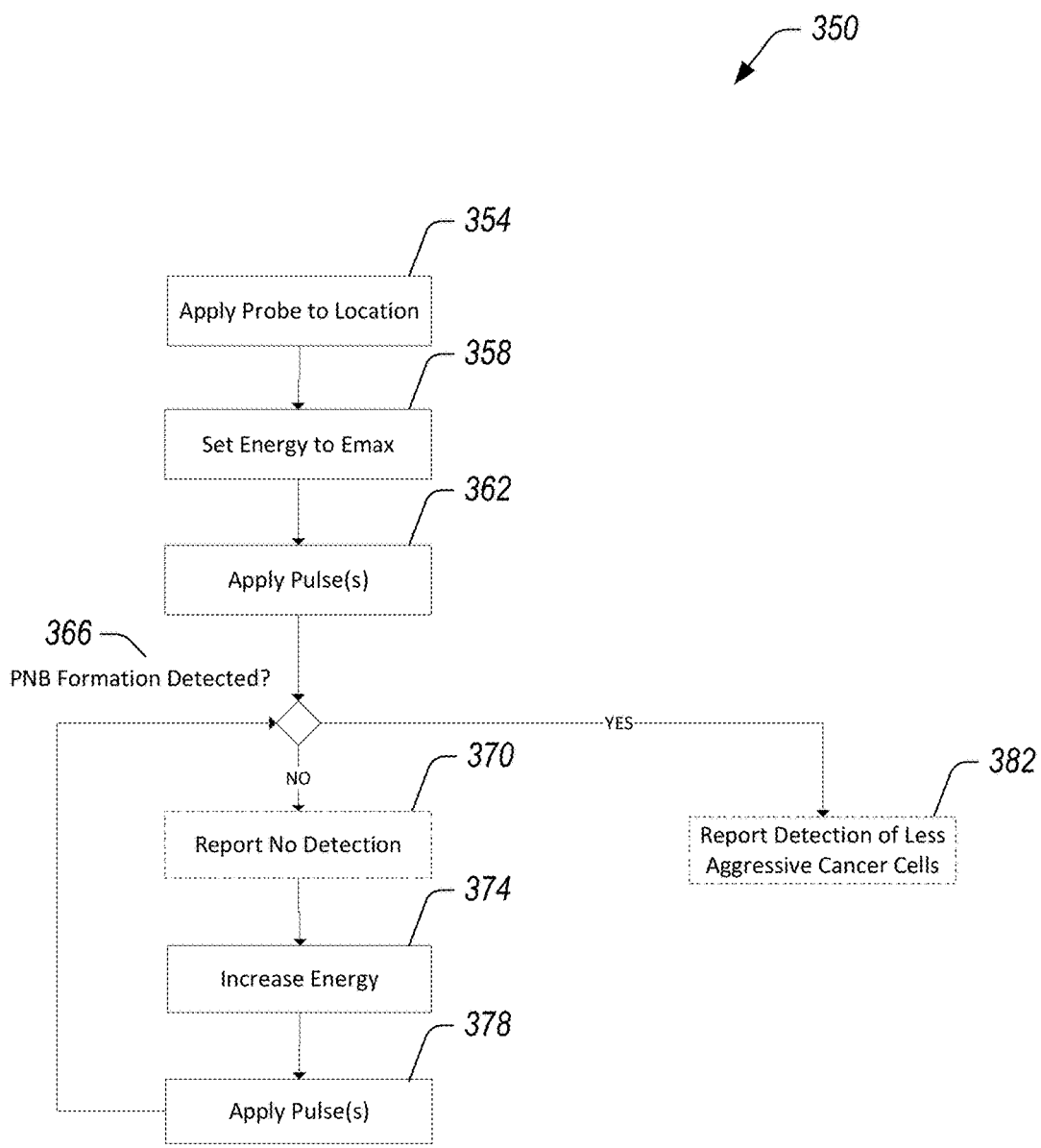
FIG. 3B illustrates an embodiment of an exemplary diagnosis process that includes a determination of aggressiveness of cancer cells in tissue.

Turning to FIG. 3B, a process 350 for determining aggressiveness of cancer cells in tissue is illustrated. Steps 354, 358, 362, and 366 can be performed in the same or similar manner as the steps 304, 308, 312, and 316 of FIG. 3A respectively. In an embodiment, in Step 358, the system can set the laser energy is $E_{max}$, which is the energy sufficient for penetrating a desired depth of the tissue at the location. When no PNB formation is detected at the decision step 366, the system can optionally report no detection at step 370. In addition, the system can increase the laser pulse energy to higher than $E_{max}$ at step 374. In an embodiment, the amount of increment can be determined based on type of suspected tumor, nanoparticle characteristics, or a combination thereof. The pulse(s) of increased energy can be applied to the same location on the patient at step 378. By increasing the energy at the same location, the system advantageously may derive information related to a measure of aggressiveness of the cancer cells. For example, in an attempt to detect presence of less aggressive cancer cells, which has a higher detection threshold fluence than the highly aggressive cancels, and detectable PNBs may not be generated at $E_{max}$ in these less aggressive cells. When PNB formation is detected with the increased energy, the system can optionally report that less aggressive cancer cells are present in step 382. If PNB formation is still not detected, the system can repeat the steps 370 (optional), 374, 378 until a predetermined endpoint energy has been applied. The endpoint energy can be determined based on type of suspected tumor, nanoparticle characteristics, or a combination thereof, and is less than the PNB generation threshold fluence of a single nanoparticle.

In some embodiments, laser pulses of a plurality of wavelengths can be applied to a location on a patient in the presence of bioconjugated nanoparticles. As described above, laser pulse wavelength for generating PNBs can depend on the type of tumor and nanoparticles. For example, PNBs of a first size can be generated in a first group of cancer cells having clusters of a first type of nanoparticles by exposure laser pulse(s) of a first wavelength, and PNBs of a second size can be generated in a second group of cancer cells having clusters of a second type of nanoparticles by exposure to laser pulse(s) of a second wavelength. In some embodiments, the first and second groups of cancer cells differ in level of aggressiveness. In some embodiments, the first and second types of cancer cells differ in types. In some embodiments, the first and second groups of cancer cells differ in both aggressiveness and types. In some embodiments, laser pulse(s) of the first and second wavelengths can be applied simultaneous to cells pre-treated with the first and second types of nanoparticles. If both the first and second groups of cancer cells are present, a synergistic PNB that is greater in size than a summation of the first and second sizes can be detected. If only one of the first and second groups of cancer cells are present, only the PNB of the first or second size can be detected. In some embodiments, laser pulses of more than two different wavelengths can be applied simultaneously to cells pretreated with more than two types of nanoparticles. This mechanism, also called a "rainbow" mechanism, can be configured to detect cancer cells of various types, levels of aggressiveness, or both. Additional details of the rainbow mechanism are described in Lukianova-Hleb, Ekaterina Y., et al., "Tunable plasmonic nanoprobes for theranostics of prostate cancer," Theranostics 1 (2011): 3-17, the entirety of which is incorporated herein by reference.

An artisan will recognize from the disclosure herein that by manipulating some or all of the energy levels of one or more the laser sources, the wavelengths of one or more radiation pulses, the size, type, shape, composition, construction or the like of the nanoparticles, the method of delivery of the same to the patient, or the specific methodology of applying the laser pulses, the system may electronically determine and report a wide variety of useful information to a caregiver, including existence, location, or depth of unwanted tissue, type of unwanted tissue, or characteristics of the unwanted tissue including a measure of aggressiveness, and the like.

Figure 5:
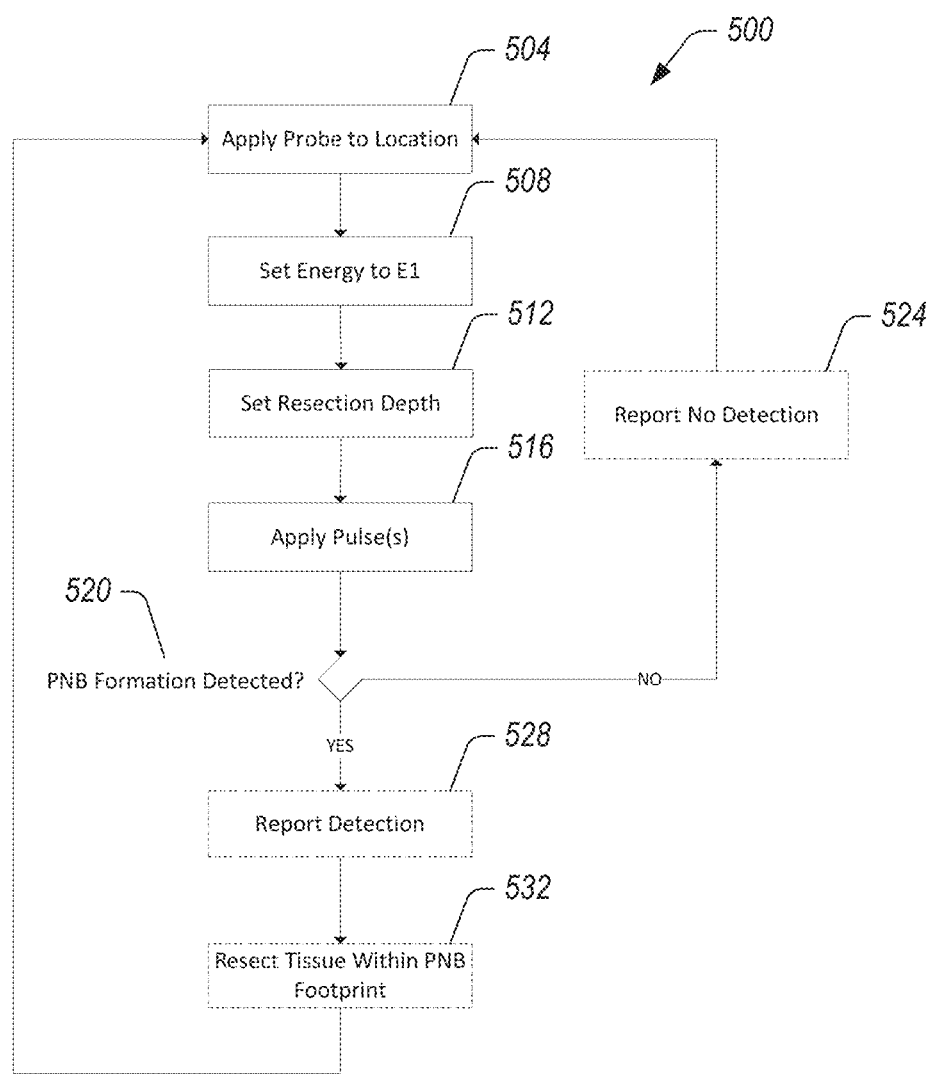
FIG. 5 illustrates an exemplary surgical process for managing a resectable MRD.
Figure 6:
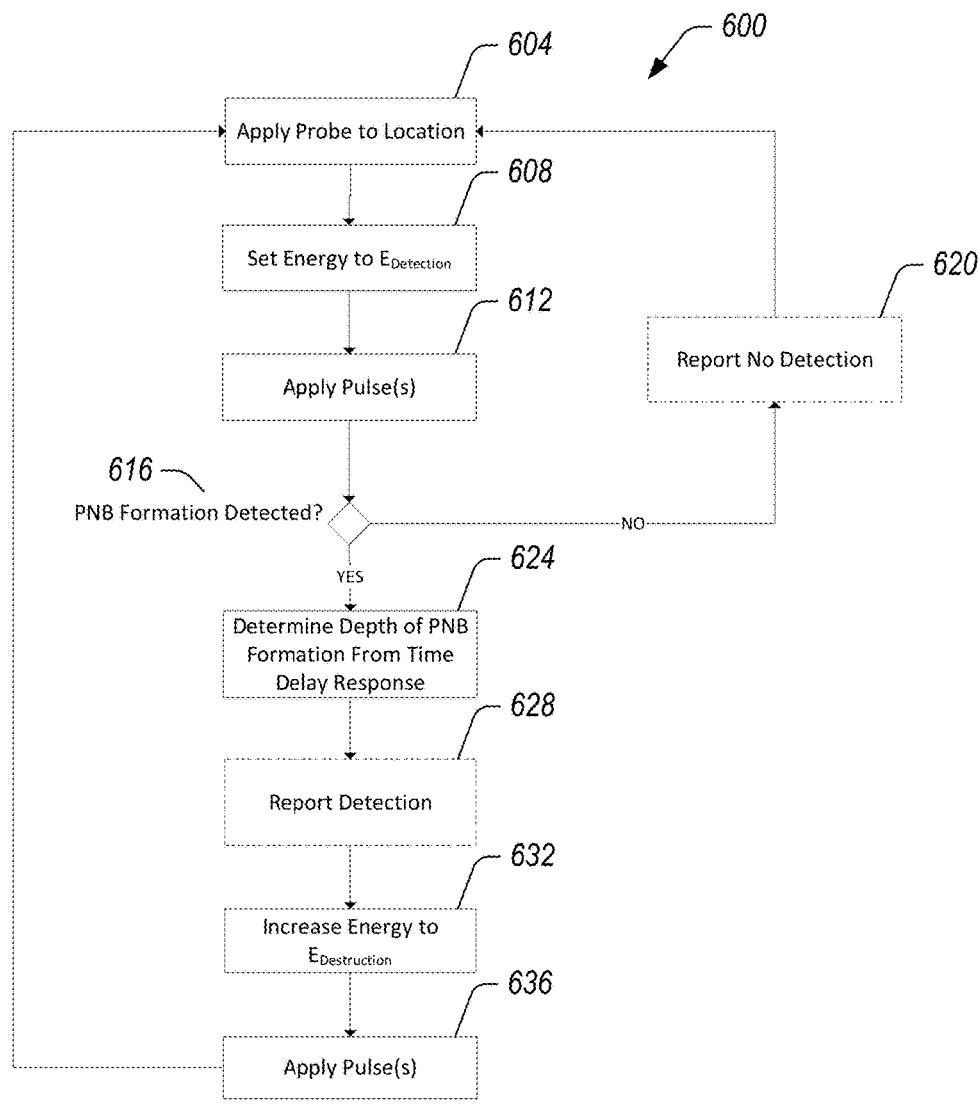
FIG. 6 illustrates an exemplary surgical process for managing an unresectable MRD.

FIGS. 5 and 6 illustrate an exemplary surgical process for resectable and unresectable MRD. In managing either resectable tumor or unresectable tumor, the surgeon may perform a primary resection of the tumor before applying a diagnosis process described above and shown in FIGS. 2 and 2A-4C.

With either the single-pulse or the multi-pulse diagnosis process, a PNB-positive time-response can be interpreted as MRD in a surgical bed within a PNB-positive zone as defined by a footprint of a PNB probe. Tissue within the PNB-positive zone can then be eliminated by a macro-surgical local resection tool 228 (FIG. 2) if the tumor is resectable, or through PNB nano-surgery if the tumor or MRD cannot be resected.

More specifically, FIG. 5 illustrates an exemplary surgical process 500 for resectable MRD. After the primary resection in a specific location, a PNB probe, that is a probe emitting laser pulses with wavelength and duration in the ranges described above, can be applied to the same location at step 504. In some embodiments, the laser probe can be applied to a new location. At step 508, the laser energy can be set at E1, which can be a detection-level energy. At step 512, a resection depth can be set. In some embodiments, the resection depth can calculated as a function of a maximum depth that a laser pulse of energy E1 can penetrate. In some embodiments, the resection depth can be manually set, for example, at 1 mm. One or more pulses of energy E1 can be applied at step 516 to determine if there are residual tumor cells after the resection. Applying a plurality of pulses of the same energy can ensure more thorough detection of tumor cells at substantially the same depth than a single pulse at that energy level. At decision step 520, a hardware processor can determine if PNB formation has been detected in manners described herein. For example, the hardware processor can receive output of an acoustic sensor and analyze a time-delay response as described above. If PNB formation was not detected, the processor can optionally generate a report that no PNB formation or tumor cells were detected at step 524. If a positive time-delay response has been detected, the processor can optionally generate a report of detection at step 528. In some embodiments, the report of detection can include PNB formation, existence of tumor cells, or existence of tumor-associated vasculature. In some embodiments, the report of detection can include depth of PNB formation, tumor cells, or tumor-associated vasculature. At step 532, tissues within a PNB footprint can be resected.

The procedure at the step 536 can be a standard "macro" surgery using the macro-surgical resection tool 228 (FIG. 2), which can be operated by either a surgeon or a robotic arm, to resect each PNB-positive zone (the probe footprint). A PNB-positive zone may have a depth of about 0-30 mm, or about 0.5-5.0 mm, a length of about 1-20 mm or about 1-10 mm, and a width of about 1-20 mm, or about 1-10 mm. For example, a PNB-positive zone can be 1 mm in depth×3 mm in length×3 mm in width. One of ordinary skill in the art would recognize from the disclosure herein other dimensions suitable for the PNB-positive zone. Follow-up control of the MRD can include applying the PNB probe again to the same location and collecting another time-response. In some embodiment, the PNB probe can emit a laser pulse of the same energy as the preceding pulse before resecting the PNB-positive zone. In the case of a PNB-positive signal, the procedure can be repeated and a PNB-positive zone can be resected each time in a loop of "detect PNB-resect-detect PNB" until the time-response reports no PNBs. In an embodiment of the present invention, options are available in the case of a PNB-negative signal from the first single laser pulse. One option is to move the PNB probe to a new location. Another option is to incise tissue in the footprint of the PNB probe to ensure removal of residual cancer cells at a margin of the primary section and to the depth corresponding to the depth of the PNB generation and detection. Yet another option is to apply additional pulses of increasing energy levels to reach deeper into the tissue. A person of ordinary skill in the art will recognize from the disclosure herein still other options. In one embodiment, a caregiver chooses from the three options. In another embodiment, a computer program chooses from the options by comparing the time-response with a threshold or a look-up table. The PNB-guided "macro" surgical process is in line with an objective of minimizing the volume of resected margins when eliminating MRD. Compared to standard surgery without the aid of the PNB technology, this PNB-guided surgical process can reduce the resected volume from a relatively large (for example, 10 mm deep×10×10 mm) to a small one (for example, 2 mm deep×3×3 mm). In some embodiments, the reduction in the resected volume can be about 50-fold. Thus, the PNB-guided surgical process can spare adjacent important structures and make surgery less morbid. For example, in head and neck surgery, in order to avoid MRD in the tongue, a surgeon removes most of the tongue first, and then does reconstructive surgery to restore the tongue with donor tissues. With PNB-guided "macro" surgical process, this morbid step can be optimized without compromising the outcome, thus improving both the patients' eligibility for surgery and their quality of life. The diagnostic process of this surgical process described herein can take only microseconds for each measurement and does not limit the surgical procedure. In clinic, PNB-guided macro-surgery can be integrated into manual, endoscopic or robotic surgery by using a standalone PNB probe or integrating it with surgical endoscope or robotic arm to provide detection and elimination of MRD in solid tissue in surgical bed in seconds.

FIG. 6 illustrates an exemplary surgical process called a PNB nano-surgery 600 for unresectable MRD. When a tumor or MRD grows along an important nerve or an artery, even PNB-guided macro-surgery as shown in FIG. 5 can be too risky. Upon detecting a PNB-positive time-response using the diagnosis process described herein at a location that is deemed unresectable by the surgeon, the cancer cell-specific mechanical impact of the PNB can be used to eliminate the cancer cells. Specifically, after the primary resection in a specific location, a PNB probe can be applied to the specific location on a patient at step 604. In some embodiments, the location can be a new location. At step 608, the laser energy can be set at a detection-level threshold fluence $E_{Detection}$. One or more pulses of $E_{Detection}$ can be applied at step 612. Applying a plurality of pulses of the same energy can ensure more thorough detection of tumor cells at substantially the same depth than a single pulse at that energy level. For example, $E_{Detection}$ can be about 10-15 mJ/cm² in the case of gold pretreated HNSCC cells. At decision step 616, a hardware processor can determine if PNB formation has been detected in manners described herein. For example, the hardware processor can receive output of an acoustic sensor and analyze a time-delay response as described above. If PNB formation was not detected, the processor can optionally generate a report that no PNB formation or tumor cells were detected at step 620. If a positive time-delay response has been detected, the processor can determine a depth of the PNB formation, which can indicate a depth of the tumor cells, from the time-delay response at step 624. The processor can optionally generate a report of detection at step 628. The processor can also optionally generate a report of the depth of PNB formation at step 632. In some embodiments, the report of detection can include PNB formation, existence of tumor cells, or existence of tumor-associated vasculature. In some embodiments, the report of detection can include depth of PNB formation, tumor cells, or tumor-associated vasculature. The laser energy can then be then be set to a cell destruction threshold fluence $E_{Destruction}$, which is higher than $E_{Detection}$, at step 632. The laser energy or fluence level can be set by the processor or manually be a caregiver. Laser pulse(s) of $E_{Destruction}$ can be applied to the same location at step 636 in an attempt to collapse or explode the PNBs, which can destroy the unresectable or residual tumor cells in which the PNBs reside. The laser pulse(s) can be applied by the processor or manually by a caregiver.

In the case of a PNB-positive time-response, the same location where the PNB-positive time-response was detected can be exposed to additional laser pulses of $E_{Destruction}$, for example, at about 40 to 400 mJ/cm², to cause destruction of the detected cancer cells by explosive effect of the PNBs. In some embodiments, laser pulses at maximal safe energy can be applied to cause maximal destruction of detected residual cancer cells by PNBs without affecting neighboring healthy tissues. The PNB nano-surgery can also be monitored in real time via the PNB signals using the diagnosis process described above and the "detect PNB-nanosurgery-detect PNB" loop can be repeated until the time-response reports no PNBs (indicating all cancer cells have been destroyed).

In an embodiment of the present invention, options can be available in the case of a PNB-negative signal from the first single laser pulse. One option is to move the PNB probe to a new location. Another option is to apply cell destruction-level laser pulse fluence to ensure removal of residual cancer cells at a margin of the primary section. Yet another option is to apply additional pulses of increasing energy levels to reach deeper into the tissue. A person of ordinary skill in the art will recognize from the disclosure herein still other options. In one embodiment, a caregiver chooses from the three options. In another embodiment, a computer program chooses from the options by comparing the time-response with a threshold or a look-up table. For unresectable therapy-resistant tumors or MRD, the PNB-induced selective mechanical destruction of residual cancer cells not only improves the surgical outcome, but can also replace toxic chemo- and radiation therapies, thus improving the quality of patients' life and making surgical treatment possible for currently ineligible patients.

Tumor Micro Environment (TME) Detection & Elimination

Figure 17A:
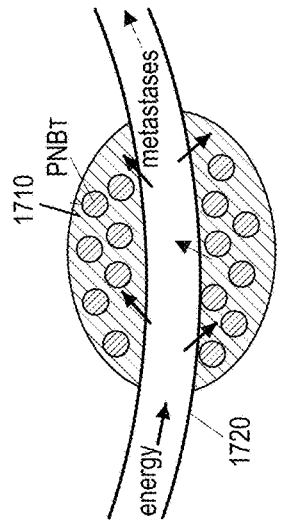
FIGS. 17A-D illustrate exemplary cancer cells and/or TME detection and elimination system in accordance with an embodiment of the disclosure.

Cancer cells can sometimes survive even after the macro- and nano-surgery described herein. The tumor micro-environment ("TME") can also survive with these cancer cells. The TME can include non-tumor targets that are biologically associated with a tumor, such as tumor-specific blood vasculature and other components that are understood by one of ordinary skill in the art. As shown in FIG. 17A, the tumor-specific vasculature 1720 can supply and support the growth of any tumor cells 1710 that survived a macro- or nano-surgery, causing local recurrence of tumor. In addition, blood flow in the tumor-specific vasculature 1720 can also bring tumor cells to other locations in the patient's body, resulting in metastases.

Figure 17B:
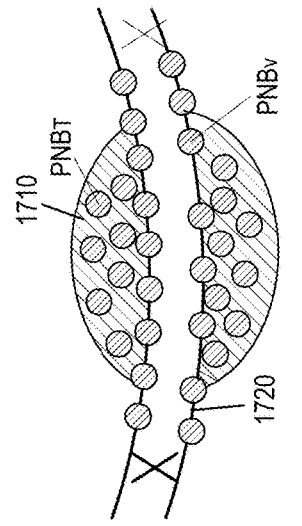
Figure 17C:
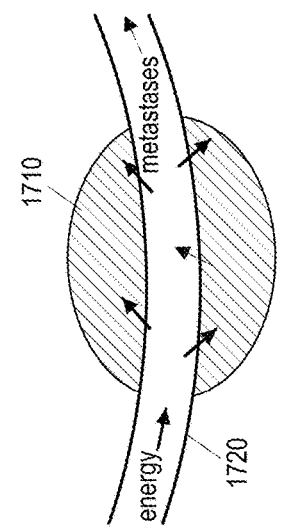

Embodiments of TME detection and elimination using the PNB technology will now be described using tumor-specific vasculature as an example, although a skilled artisan will understand from the description herein that the embodiments of TME detection and elimination disclosed herein can be applied to any type of TME. Tumor-specific vasculature can differ from normal blood vessels, such as by expressing on the wall of the vessel tumor-specific receptors. Examples of tumor-specific receptors on the vessel wall can include VEGF-A, VCAM-1, avb3 integrins, and the like. By administrating nanoparticles conjugated to the vascular-specific ligand that target these receptors, the PNB technology described above for detecting and eliminating cancer cells can be used to detect and eliminate the tumor-specific vasculature. More specifically, as shown in FIG. 17B, gold conjugates can be systemically administered and $PNB_T$ can form in the tumor 1710. As shown in FIG. 17C, $PNB_V$ can form on the epithelial wall of the tumor-specific vessel 1720. In some embodiments, the same gold conjugate with the same ligands configured for formation of $PNB_T$ can be configured for forming $PNB_V$. In other embodiment, vasculature-specific gold conjugates and ligands can be used for generating $PNB_V$. In some embodiment, gold spheres of 240 nm can be used for the generation of PNBs on the epithelial wall of the tumor-specific vasculature under excitation with a 1064 nm laser pulse. In some embodiment, gold spheres of 60 nm can be used for the generation of PNBs on the epithelial wall of the tumor-specific vasculature under excitation with a 782 nm laser pulse.

The process as illustrated in FIG. 6 and described above can be applied for detection and destruction of the tumor-specific vasculature. After application of laser pulse(s) for $PNB_V$ generation or tumor-specific vasculature detection, laser pulse(s) of a higher energy sufficient for destruction of the vasculature by the explosive impact of the $PNB_V$ can be applied. The PNB-induced destruction of the tumor-specific vasculature and disruption of the blood supply and flow may additionally destroy residual cancer cells that survived a macro- or nano-surgery by mechanical impact due to explosive effect of the PNBs. As described above, the destruction of the tumor-specific vasculature can further improve cancer treatment by reducing the possibility of the local recurrence by cutting off the energy or nutrient supply to residual local cancer cells. The destruction of the tumor-specific vasculature can also reduce the possibility of remote metastases from the target tumor by removing the channel for the residual cancer cells to travel to other parts of the patient's body.

Combination of Cancer Cell and TME Detection and Elimination

Figure 17D:
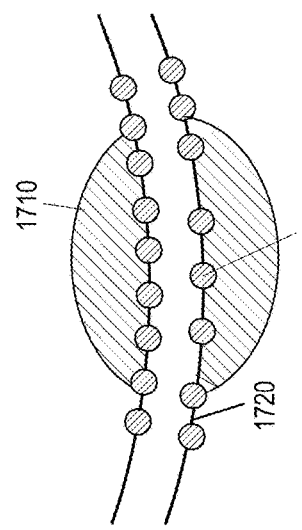

In some embodiments, in addition to using the PNB-induced destruction of the TME as a stand-alone treatment, the PNB-induced destruction of the tumor-specific vasculature and disruption of the blood supply and flow can be an intra-operative adjuvant treatment to the direct treatment of unresectable/residual tumors. As shown in FIG. 17D, $PNB_T$ can form in the tumor 1710 and $PNB_V$ can also form on the epithelial wall of the tumor-specific vessel 1720 at the same time or in one treatment with laser pulses. That is, gold conjugates can be administered to both the cancer cells and the tumor-specific vasculature to generate both $PNB_T$ and $PNB_V$. In some embodiments, the same gold conjugate with the same ligands configured for formation of $PNB_T$ can be configured for forming $PNB_V$. In other embodiment, vasculature-specific gold conjugates and ligands can be used for generating $PNB_V$. In some embodiments, the same gold conjugate with the same ligands can be used to form the $PNB_T$ and $PNB_V$. In other embodiment, tumor-specific gold conjugates or ligands can be used for generating $PNB_T$ and vasculature-specific gold conjugates or ligands can be used for generating $PNB_V$. Although the combination of cancer cell and TME detection and elimination are described using tumor-specific vasculature as an example, a skilled artisan will understand from the description herein that these embodiments can be applied to any type of TME.

The process as illustrated in FIG. 6 and described above can be applied for detection and destruction of the cancer cells, and the tumor-specific vasculature (if present). In some embodiments, the same detection-level energy laser pulse(s) can be applied to form both the $PNB_T$ and $PNB_V$ in the cancer cells and the tumor-specific vasculature respectively. In other embodiments, laser pulse(s) of different detection-levels energy can be used to form the $PNB_T$ and $PNB_V$. After application of laser pulse(s) for generating the $PNB_T$ and $PNB_V$, if tumor, or tumor-specific vasculature, or both are present, laser pulse(s) of a higher energy sufficient for destruction of the tumor cells and the tumor-associated vasculature by the explosive impact of the $PNB_T$ and $PNB_V$ can be applied. In some embodiments, the same higher energy laser pulse(s) can be applied to collapse both the $PNB_T$ and $PNB_V$, leading to destruction of both the cancer cells and the tumor-specific vasculature substantially simultaneously. In other embodiments, laser pulse(s) of different levels of higher energy can be used to collapse or explode both the $PNB_T$ and $PNB_V$. The PNB-induced destruction of the tumor-specific vasculature and disruption of the blood supply and flow may destroy additional cancer cells by mechanical impact due to explosive effect of the $PNB_V$. Targeting and destroying both the tumor and the tumor-specific vasculature can further improve the surgical outcome. For example, the combination of PNB-assisted removal of tumor and TMD can achieve about 5-10 fold improvement in overall survival compared to standards of care.

EXAMPLES

Examples of aspects of the embodiments of the present disclosure will now be described. More details of aspects of the embodiments of the present disclosure are provided in Appendices A and B.

Example 1: Cancer Models and Characterization

HNSCC is a very aggressive and lethal cancer whose surgery is challenged by resectable and unresectable MRD which later often cause lethal local recurrence. This cancer was modelled with aggressive and resistant HN31 cells obtained from J. Myers' laboratory, UT MD Anderson Cancer Center (Houston, Tex.) and tested for mycoplasma contamination before their use. HNSCC overexpress Epidermal Growth Factor Receptor, against which there is a clinically-approved antibody, Panitumumab. Four cancer models of increasing complexity were used. To verify acoustic detection of PNBs, intact or gold conjugate-pretreated HNSCC cells in transparent media (model 1) were used. To study acoustic detection of cancer cells in solid tissue (model 2), a precise amount of gold conjugate-pretreated cancer cells was injected into a specific depth of a chicken breast with a nano-syringe. In the 3rd, in vivo model (model 3), pretreated and intact cancer cells were similarly injected into the surgical bed of anesthetized mice (athymic nude, strain CRL-490, 6 weeks age). To study the intraoperative detection and elimination of MRD (model 4), a deeply-seeded xenograft HNSCC tumor was established in the mouse. The tumor was grown to 5-6 mm size to ensure its infiltration into the normal tissue underneath and to achieve a mature vascularization (important for the systemic delivery of gold conjugates). To establish MRD intraoperatively, the tumor was grossly resected using aseptic surgery. The nest of the resected primary tumor was considered to have MRD as had been verified previously by observing almost 100% local recurrence after resecting the primary tumor. The area of the surgical bed outside a >3 mm margin around the tumor nest was considered as MRD-negative location. Presence of MRD after resection of the primary tumor was confirmed with standard pathology, such as H&E staining in FIG. 7 and later by observing local recurrence. After the PNB and surgical procedures in MRD-positive and -negative locations were completed, the wound was closed and the animal was monitored for local tumor recurrence and overall survival. The cancer metrics that were used include: (1) the number of injected cells in the 2nd and 3rd models, while in the 4th model, (2) the volume of the recurrent tumor was used, and (3) the animal overall survival time after surgery. Six animals were used for groups 1 and 2 and five animals for group 3. Animals were euthanized when the size of the recurrent tumor reached 10 mm, which was set as the moribund threshold. Animal group sizes were set to support statistically valid data and to minimize animal use. Animals were randomly assigned to groups for the experiments. These studies were not blinded since the same investigators performed the grouping, dosing and analyses, rendering it unfeasible. Animals were used according to Animal Care Use Guidelines under the protocols approved by the Institutional Animal Care and Use Committees of Rice University and Houston Methodist Research Institute.

Example 2: Gold Targeting and Clustering

To form in vivo intracellular clusters of gold colloids as PNB sources, several universal and previously verified mechanisms were used: leaky tumor micro-vasculature and the small size of the gold colloid conjugates (60 nm spheres) enable them to reach the tumor with the help of an effect called "enhanced permeability and retention" as shown in FIG. 2A, which prompts the receptor-antibody based accumulation of gold conjugates at the surface of cancer cells as shown in FIG. 2B, and finally the receptor-mediated endocytosis of gold conjugates as shown in FIG. 2C. This is endocytosis, the universal cell defense mechanism, which internalizes gold nanoparticles and concentrates them into clusters in endo-lysosomal compartments as shown in FIG. 2C, as was found earlier in vitro and in vivo. This mechanism, which efficiently differentiates cancer and normal cells by forming the largest gold clusters only in cancer cells (FIG. 2C), was also verified in vivo for HNSCC: while tumor-average cluster size was around 300 nm (equivalent of tens of aggregated 60 nm nanoparticles) the adjacent normal tissue yielded only 64 nm (equivalent of single nanoparticles). The increase in size of the gold cluster provides the selective generation of PNBs in HNSCC cells because the PNB generation threshold fluence rapidly decreases with the cluster size (see the PNB sections below for details). The clustering mechanism is sensitive to the nanoparticle diameter: larger particles (>100 nm) cannot be easily internalized by cancer cells and therefore cannot create intracellular clusters. Smaller particles (<10 nm) are rapidly cleared by the organism and therefore cannot efficiently accumulate in the tumor.

The low doses of gold colloids employed are associated with negligible systemic toxicity. 60 nm spheres (NanoComposix, Inc, San Diego, Calif.) were used to covalently conjugate (VanPelt Biosciences LLC (Ijamsville, Md.)) to the clinically-approved anti-Epidermal Growth Factor Receptor antibody, Panitumumab (Vectibix, Amgen Inc., Thousand Oaks, Calif.). This antibody is used in clinic against HNSCC. To form gold clusters in vitro, gold conjugates were incubated with cells for 24 h under physiological conditions at the concentration of gold conjugate suspension corresponding to the optical density of 0.08 (measured at the maximum of the optical spectrum as shown in FIG. 8A). This corresponds to a dose of approximately 0.7 μg/ml. To form gold clusters in vivo, gold conjugates were systemically administered intravenously at the low dose of 4 mg/kg body weight 24 hours prior to the optical excitation, in order to allow their efficient clustering in the tumor. This dose is only 1-10% of those reported for the diagnostic and therapeutic doses of gold nanoparticles in vivo. These doses, timing and administration protocol were achieved as a result of several optimization experiments focused on the efficient clustering of gold nanoparticles in tumors:

A. The gold clustering efficacy was quantified through four independent metrics and methods: (1) by measuring the level of gold in tumors and other organs (which were harvested at a specific time, 6-72 h, after the systemic administration of gold conjugates) with inductive-coupled plasma mass-spectroscopy (ICP-MS); (2) by directly measuring the size of gold clusters in harvested tissues with transmission electron microscopy; (3) by measuring PNB lifetime (the metric of the maximal diameter of PNB which correlates with the cluster size) in slices of the harvested tissue, and (4) by measuring the acoustic amplitude of PNB time-responses in vivo. It was found that the systemic administration of gold nanoparticle conjugates is preferable to their local injection and results in tumor-specific clustering in vivo. In addition, it was found that 60 nm gold spheres provide the best generation of PNBs in HNSCCC in vivo compared to smaller nanoparticles. It is difficult for cells to internalize nanoparticles >100 nm. With the above methods, it was determined that efficient clustering in vivo requires at least 24 hours of lead time after the systemic injection of gold conjugates.

Figure 9A:
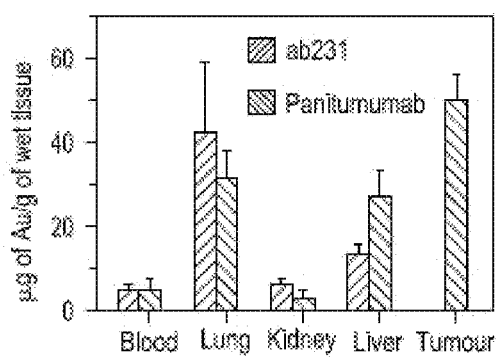
FIG. 9A illustrates exemplary biodistributions of gold conjugates with human antibodies in nude mice and gold conjugates with mouse antibodies in normal mice.

B. To optimize systemic targeting, the previous measurements were amended with the ICP-MS (Perkin Elmer Nexion 300 ICP-MS, Perkin Elmer, Inc., Waltham, Mass.) evaluation of the gold accumulation in tumors and other organs as a function of:

The organ: tumor, lung, liver, kidney and blood (FIG. 9A);

The targeting antibody (FIG. 10A): active targeting, compared to passive targeting (gold without antibody) is important for efficient systemic targeting.

The size of the primary tumor (FIG. 10B): the tumor stage determines the level of tumor vasculature in a xenograft model, and it is the vasculature which delivers gold to a tumor. In the case of MRD detection, tumors are usually mature enough, and this ensures the efficient systemic delivery and accumulation of gold under active targeting with an HNSCC-specific antibody.

The interaction of the targeting antibody with the immune system. To ensure the clinical translation of gold conjugates, the anti-Epidermal Growth Factor Receptor antibody "liver sink" effect (which is associated with clinical challenges in using such antibodies) and the safety of gold in vivo were additionally studied. A normal mouse with an active immune system was identically treated with gold conjugated to anti-mouse EGFR antibody. The gold biodistribution (FIG. 9A) was similar to that obtained in the xenograft model and human antibody (Panitumumab). Thus, gold conjugates (unlike the antibody alone) did not reveal a significant liver sink effect and therefore can be administered in clinic at a relatively low dose.

As a result of this optimization, the following optimal combination was determined: primary tumors should be above 5 mm, and Panitumumab antibody should be used to target gold, 24 hours are required to achieve clustering, and 60 nm gold spheres at a dose of 4 mg/kg.

Example 3: Safety of Gold Nanoparticles In Vivo

Figure 9H:
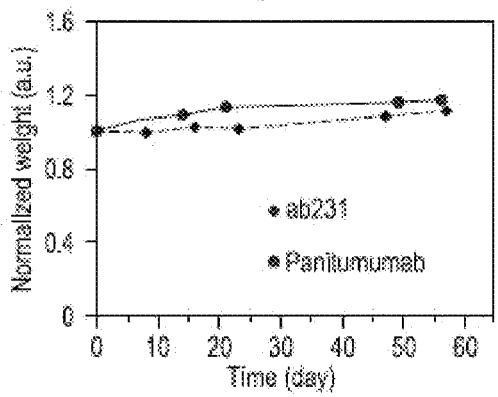
FIG. 9H illustrates an exemplary body weight as a function of time for mice with no injection of gold conjugates and mice after systemic injection of gold conjugates.
Figure 9D:
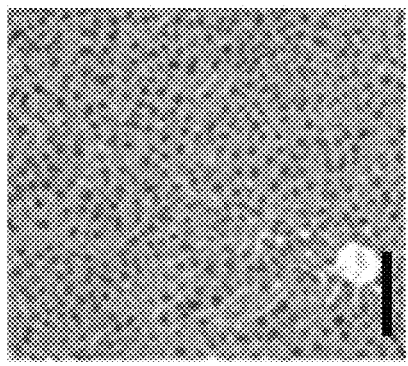
FIG. 9D is an exemplary histological analysis of a kidney obtained from an animal that was not administered gold conjugates.
Figure 9G:
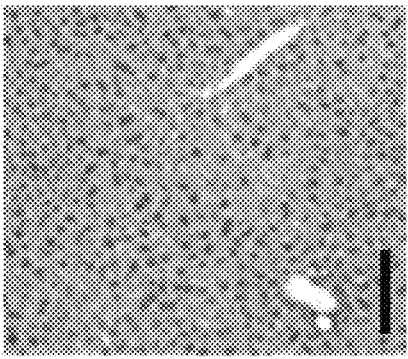
FIG. 9G is an exemplary histological analysis of a kidney obtained from an animal 72 h after administration of gold conjugates.
Figure 9C:
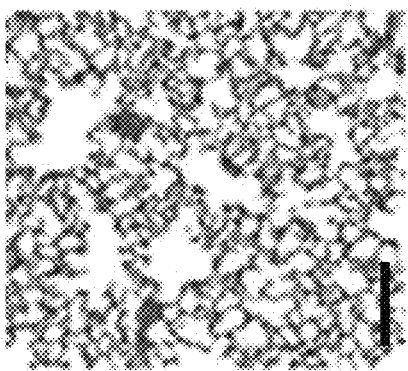
FIG. 9C is an exemplary histological analysis of a lung obtained from an animal that was not administered gold conjugates.
Figure 9F:
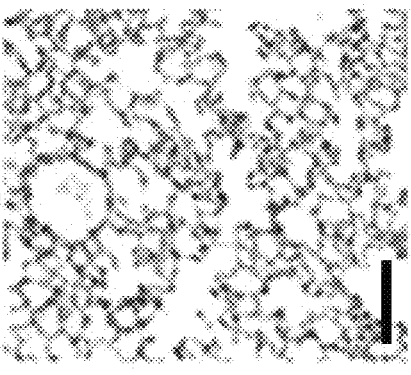
FIG. 9F is an exemplary histological analysis of a lung obtained from an animal 72 h after administration of gold conjugates.
Figure 9B:
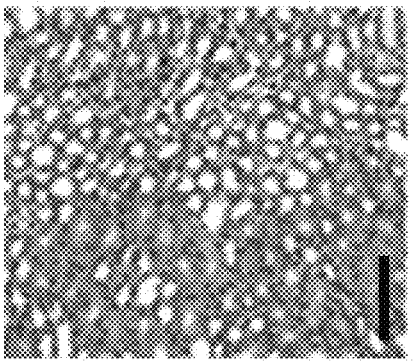
FIG. 9B is an exemplary histological analysis of a liver obtained from an animal that was not administered gold conjugates.
Figure 9E:
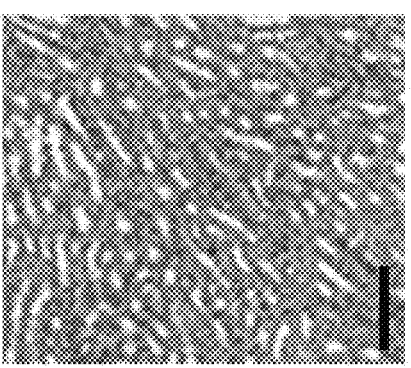
FIG. 9E is an exemplary histological analysis of a liver obtained from an animal 72 h after administration of gold conjugates.

The toxicity of gold conjugates in vivo has been measured short term (24 and 72 h after administration) and long term (over 1 month). Three animals were studied for each timepoint. To determine short-term toxicity, the harvested liver, kidney, spleen and lung were analyzed for necrosis, apoptosis and other standard signs of toxicity via standard pathology. The harvested organs (kidney, lung, liver, heart) were placed in 10% neutral buffered formalin and fixed for up to 48 hours. Organs were then processed routinely and coil sections were stained with hematoxylin and eosin (H&E). Sections were examined by a board certified veterinary pathologist. Regions of normal tumor/organ and necrotic tumor/organ were delineated. The metric of tissue damage was the % of necrosis, defined as the ratio of the area of grossly necrotic tissue to the total area of tissue in a given section. Long-term toxicity was monitored by measuring animal weight and behavior. More sophisticated methods were not applied because the gold nanoparticles and their low doses used were safe: no signs of toxicity were observed for the period >2 months. The short- and long-term toxicity in vivo was verified. The histological evaluation of organs harvested at 24 h and 72 h from intact and gold-treated mice (FIGS. 9B-9G) revealed no toxic effects of the gold, as shown in Table 1 below. Based on the high safety of the gold, the long-term toxicity was analyzed only by monitoring the body weight and animal behavior (two standard parameters) in intact and gold-treated mice and also revealed no adverse effects (FIG. 9H). Therefore, the gold conjugates, doses, and the systemic targeting method employed were safe in vivo and provided efficient delivery of the gold conjugates to and their clustering in a tumor to support tumor-specific PNB generation in vivo.

TABLE 1

Short-term toxicity of treatment (defined as % of grossly necrotic area/total examined area)

| Treatment | Time | Kidney | Liver | Lung |
|---|---|---|---|---|
| Untreated | 24 h | 0% | 0% | 0% |
|  | 72 h | 0% | 0% | 0% |
| PNB | 24 h | 0% | 0% | 0% |
|  | 72 h | 0% | 0% | 0% |

Example 4: Plasmonic Nanobubble (PNB) Generation

PNBs were generated around clusters of gold spheres with single near-infrared laser (NIR) pulses (782 nm, 30 ps, Ekspla PL2251/OPG03, Ekspla UAB, Lithuania). As shown in FIG. 8A, optical absorbance under stationary optical excitation peaks between 500 and 600 nm and is negligible at 782 nm. While the stationary optical excitation of gold spheres in near-infrared is not efficient due to their low optical absorbance in this spectral interval, the non-stationary optical excitation method described herein provides efficient PNB generation around these nanoparticles with a 30 ps laser pulse at NIR wavelength of 782 nm, the wavelength associated with minimal bio-damage and maximal tissue penetration depth. Due to the transient photothermal modification of the nanoparticle surface by a short NIR laser pulse, the PNB generation efficacy at 782 nm reaches the level achieved by excitation at the visible wavelength (FIG. 8B). Unlike any nanoparticle, a PNB is a non-stationary transient event, an expanding and collapsing vapor nanobubble of nanosecond duration, usually without recoil. Such a nanobubble results from the rapid evaporation of the liquid around an overheated gold cluster due to the absorption and plasmonic conversion of the laser pulse energy. The use of a nanoparticle cluster instead of single nanoparticles or their ensembles provides a significant reduction in the threshold laser fluence of the PNB generation and an increase in the PNB generation efficacy because the threshold fluence decreases with the cluster size. This unique property of PNB, in turn, provides the high cancer cell specificity of PNB in vivo compared to any targeted nanoparticles, since the largest clusters are self-built by aggressive cancer cells and do not emerge in normal cells (FIG. 2D). The fluence of the laser pulse was applied below the PNB generation threshold for single nanoparticles but above the PNB generation threshold for their large clusters. Thus, PNBs are selectively generated only around large clusters, that is, in cancer cells, and do not emerge in normal cells even despite unavoidable non-specific accumulation of single nanoparticles in normal cells. In addition to the high cancer cell specificity, a PNB efficiently thermally insulates the overheated gold cluster from the outer media, thus preventing any thermal bio-damage to any object outside the PNB.

Figure 11:
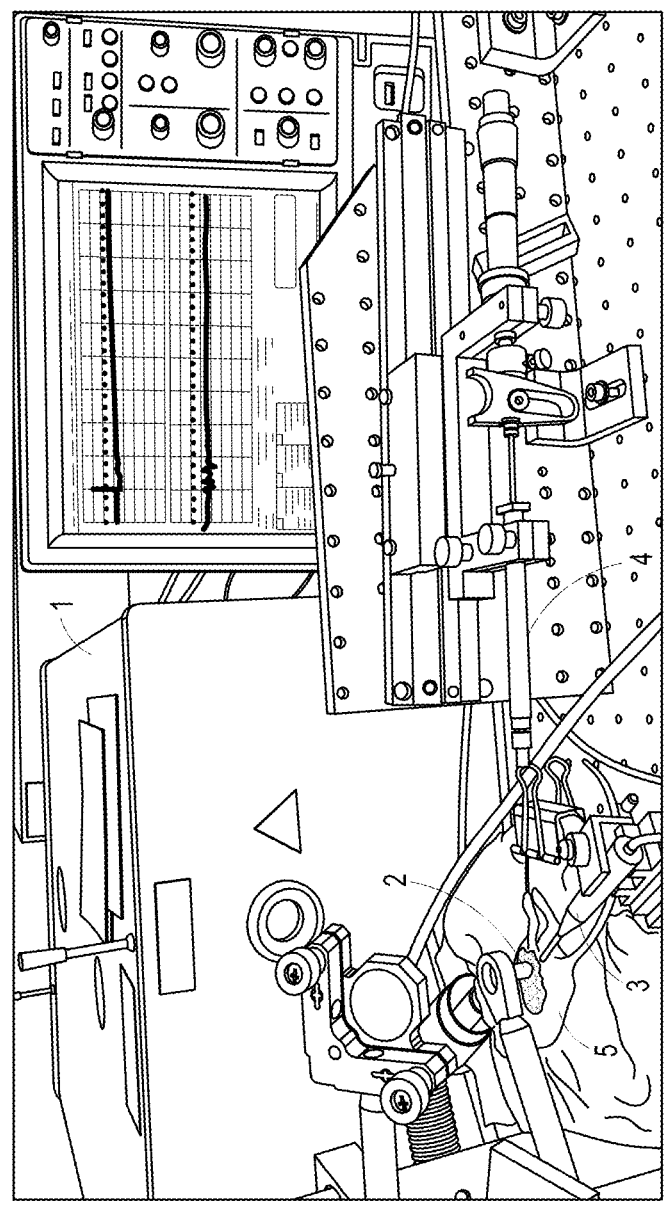
FIG. 11 illustrates an exemplary experimental setup for in vivo generation and detection of PNBs.

The laser fluence was measured through the acquisition of the beam image in the target plane (to obtain the beam diameter, we used the imagers Andor Luca EMCDD (Andor technology Ltd, Belfast, UK) and Spiricon (Ophir-Spiricon LLC, N. Logan, Utah) and pulse energy meter (Ophir-Spiricon LLC, N. Logan, Utah). Single cell experiments used a photothermal microscope. In the in vivo experiments, the laser pulse was delivered to the tissue via a custom endoscope in an experimental setup as shown in FIG. 11. Specifically, the exemplary experimental setup in FIG. 11 comprises (1) a pulsed NIR laser (782 nm, 30 ps); (2) an endoscope for the delivery of the laser beam (diameter 4 mm) into a surgical bed; (3) an acoustic sensor with pre-amplifier in the back; (4) a nanosyringe for injection of cancer cells into the surgical bed of (5) anesthetized mouse. The cells were injected into the surgical bed of a mouse in specific amounts from 3 to 100 with a 0.5 µl Hamilton nano-syringe (Sigma-Aldrich Co. LLC, St. Louis, Mo.) with micrometer drive (FIG. 11).

Example 5: Methods of PNB Detection

To detect PNBs optically with a single PNB sensitivity and resolution, an optical scattering method was used. A continuous probe laser beam (633 nm, 05-STP-901, Melles Griot, Rochester, N.Y.) was focused on the PNB source and its axial intensity was monitored after the object with a high-speed photodetector (FPD 510-FV, Menlo Systems GmbH, Martinsried, Germany) connected to a digital oscilloscope (LeCroy 42Xs, Teledyne LeCroy, Chestnut Ridge, N.Y.). The vapor-liquid boundary of a PNB scatters the incident probe laser beam thus reducing its axial intensity. The expansion and collapse of a PNB creates a specific dip-shaped pattern in the time-response of the intensity of the probe laser to a single pump laser pulse. Its duration, or lifetime, characterizes the maximal diameter of a PNB. This method directly detects individual PNBs, but only in optically transparent media.

To detect PNBs in opaque tissue (FIG. 2D), the pressure pulse emitted by the expanding and collapsing PNB was detected with a custom-built acoustic detector (Precision Acoustics Ltd, Dorset, UK) comprised of a broadband ultrasound sensor of a needle type integrated with a pre-amplifier. The sensor used an external power supply with a second pre-amplifier. The output of the second pre-amplifier was connected to a digital oscilloscope to register an acoustic time-response to a single laser pulse. In tissue, a diagnostic method based on the co-registration of the two time-responses from a cancer-free location (the reference) and from the location where cancer cells might be present (the test) was used. The differential response was determined by subtracting the reference response from the test response. For signal metrics, the peak-to-peak amplitude of the differential response was used. As a cancer diagnostic metric, a Diagnostic Index (DI), defined as the relative increase in test response amplitude ($V_{test}$) over the reference or background response amplitude ($V_{ref}$) was additionally used:

$$DI = \frac{V_{test} - V_{ref}}{V_{ref}}$$

Example 6: Detection of PNB Ex Vivo

To establish a PNB diagnostic mechanism, PNBs were first generated and detected in individual gold-pretreated (60 nm spheres conjugated to Panitumumab) HNSCC cells in transparent media. PNBs were simultaneously detected optically and acoustically in response to a single laser pulse (782 nm, 30 ps) of variable fluence above the PNB generation threshold (which was found to be 10-15 mJ/cm$^2$ for gold-pretreated HNSCC cells). Above the threshold fluence, the optical signal typical for PNBs (FIG. 12A) coincided with a bipolar spike in the simultaneously detected acoustic time-response (FIG. 12B) for gold-pretreated cells 1210. No PNBs and no spikes were detected in intact (not pretreated with gold) cells 1220 under the same pulses (FIGS. 12A-12B). The amplitude of the acoustic bipolar spike almost linearly correlated to the optically measured PNB lifetime, the metric of the PNB maximal diameter (FIG. 12C). Therefore, bipolar spikes in detected acoustic time-responses were attributed to PNBs. This in vitro experiment established the principle of the acoustic detection of PNBs in single cancer cells.

Figure 13:
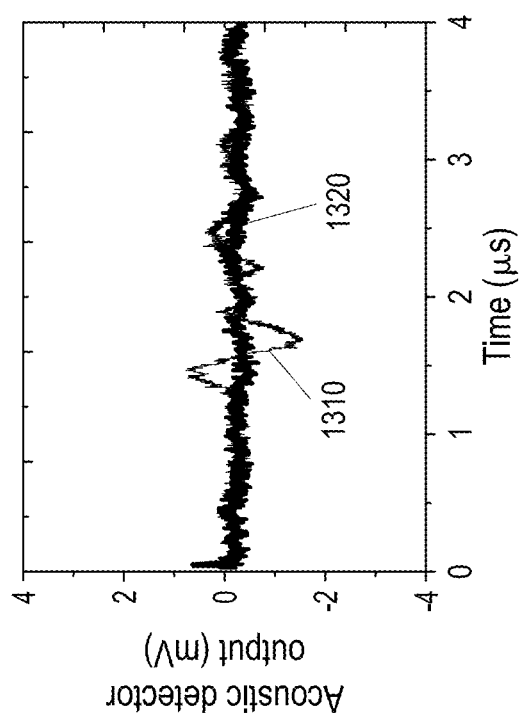
FIG. 13 illustrates exemplary acoustic time-responses to sequential laser pulses as obtained in the same location of the chicken breast in FIGS. 12D-F after injecting 10 or more gold pre-treated cancer cells.

Next, transparent cell media was replaced by a chicken breast to model intraoperative conditions of solid tissue (FIG. 12D). Gold-pretreated cancer cells were injected one by one with a nano-syringe into the tissue at a specific depth of 1 mm or 3-4 mm. A single laser pulse (782 nm, 30 ps, 70 mJ/cm$^2$, 4 mm diameter) was applied via an endoscope, and the acoustic time-response to each laser pulse was obtained with an ultrasound probe. The injection of three gold-pretreated cancer cells produced a PNB-specific spike 1210 in the acoustic time-response (FIG. 12E). No such spikes were observed after the injection of the same and a higher number of intact cells (FIG. 12E). These spikes obtained for gold-pretreated cells were similar to those obtained for PNBs in the previous experiment, and therefore were attributed to PNBs and, in this case, reported single cancer cells in solid tissue. The injection of 10 and more cells returned multiple spikes in acoustic time-responses 1310 (FIG. 13). The temporal separation of spikes in one time-response implied that the cells were spatially distributed over 2-3 mm distance in the direction of the probe axis. Thus, a single time-response reported multiple cells in different locations within the footprint of a single laser pulse. The detection procedure took about 1 ms. Next, the Diagnostic Index (the relative increase in the amplitude of the test time-response versus that of the reference, cancer-free, time-response as shown in Example 5) obtained for each cell injection was analyzed as function of the number of injected gold-pretreated cancer cells and their depths in the tissue (FIG. 12F). The Diagnostic Index was nearly proportional to the number of injected cells in the range of 3 to 100 cells. At 1 mm depth 1230, PNBs reported single cancer cells with good signal-to-background ratio. At 4 mm depth, the detection threshold increased to 30 cells 1240. These experiments established the PNB diagnostics mechanism for residual cancer cells in solid tissue at the depth comparable to that for surgical margins.

Example 7: In Vivo Intraoperative Detection of Cancer Cells

Figure 14C:
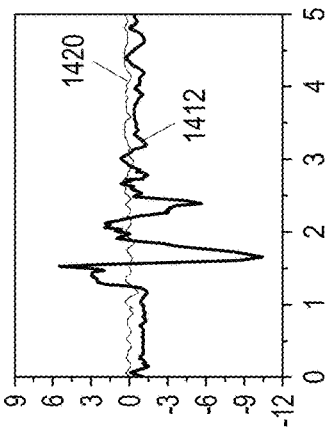
FIGS. 14B-C illustrate exemplary acoustic time-responses before and after injection of gold conjugate-pretreated cancer cells in FIG. 14A.
Figure 14B:
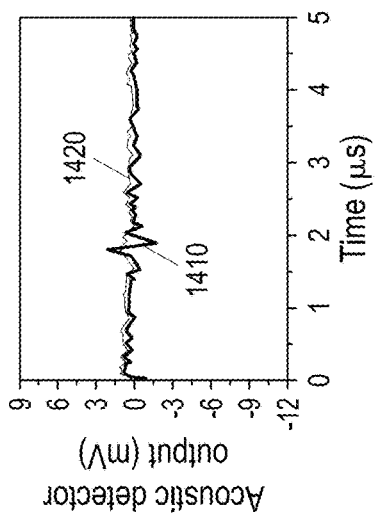
Figure 14A:
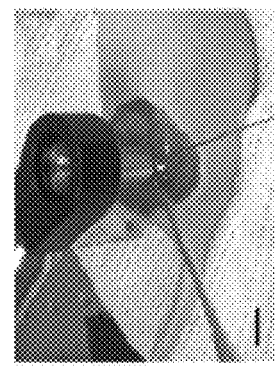
FIG. 14A illustrates an exemplary view of the mouse in FIG. 11.
Figure 14E:
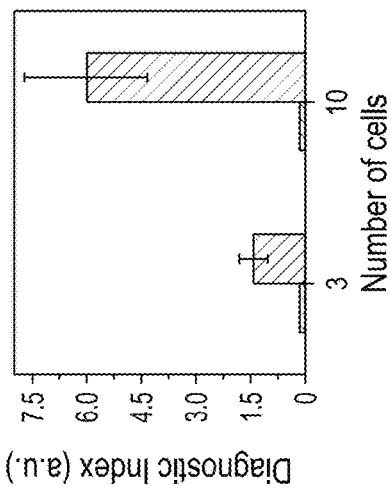
FIG. 14E illustrates an exemplary Diagnostic Index as a function of amount of injected cells for gold conjugate-pretreated and non-gold conjugate-treated cancer cells.
Figure 14D:
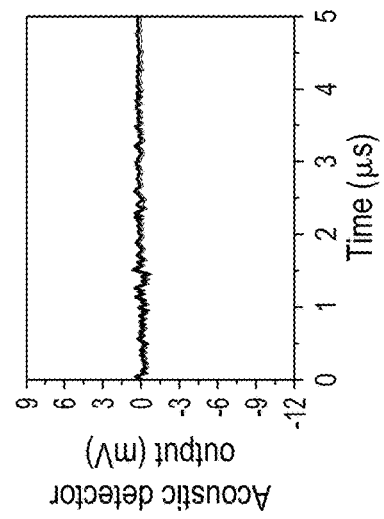
FIG. 14D illustrates exemplary acoustic time-responses before and after injection of intact (non-gold conjugate-treated) cancer cells in FIG. 14A.

Individual gold-pretreated or intact cancer cells (3 and 10) were injected to the depth of 1 mm into the surgical bed of an anesthetized mouse (FIG. 14A, FIG. 11). Prior to and following each injection, a single laser pulse (782 nm, 30 ps, 70 mJ/cm$^2$, 4 mm diameter) was applied to the injection area. The acoustic time-response to the pre-injection pulse was used as a cancer-free reference signal 1420 (FIG. 14B) and the acoustic time-response to the post-injection pulse 1410 was used as a test signal. PNB-specific spikes (similar to those described above for individual gold-pretreated cancer cells) were observed after the injection of three gold-pretreated cancer cells (FIG. 14B). For ten cells, a multi-peak time-response 1412 was detected (FIG. 14C) meaning that the cells were distributed over a distance of 2-3 mm in the direction of the probe axis. Pre-injection reference signals (FIG. 14B-14D) showed minor peaks not observed in the in vitro model and could have been caused by the bulk photothermal effect in blood. This bulk effect cannot produce vapor nanobubbles (in contrast to the highly localized photothermal effect of gold clusters in cancer cells) and delivered almost identical pre-(FIG. 14D) and post-injection (FIG. 14D) signal components in time-responses of intact cells which produced no PNBs. With no false-positive signals detected for untreated cells, and no false-negative signals detected for even three gold-pretreated cells, the PNBs were highly cancer cell-specific, as can be seen from the values of the Diagnostic Index the as function of the number of cells and their gold pretreatment (FIG. 14E). In FIG. 14E, the bar on the left represents a reference, cancer-free signal and the bar on the right represents the acoustic time-response after injection of the 3 or 10 gold conjugate pre-treated cancer cells, respectively. Thus the detected PNB-positive signals were attributed to residual cancer cells in solid tissue. The time to result was within 1 ms per location of the probe. Laser pulses caused no detectable damage to the irradiated tissue in the surgical bed due to a relatively low cumulative dose (70 mJ/cm$^2$), which is well below the optical doses associated with non-invasive in vivo imaging. The safety of laser pulses and the selectivity of even large lethal PNBs can be additionally seen from the response of the cancer-normal cell mixture, identically pretreated with gold and exposed to a single broad laser pulse: even when a PNB explodes a cancer cell, surrounding normal cells survive. This high selectivity of PNBs has recently been verified for even higher laser fluences up to 140 mJ/cm$^2$.

Example 8: Probing Various Tissue Depths with Two Laser Pulses

The single pulse diagnosis processes described above are limited in solid tissues by the strong optical attenuation of the laser fluence with the tissue depth. In most of the experiments, single pulses were used at a single level of laser fluence. This is sufficient for the diagnostics of superficial MRD in surgical margins within 1-2 mm depth (which is still better than any of optical diagnosis processes whose sensitivity is limited by tens of micrometers of solid tissue depth for microscopic tumors or single cancer cells). To better accommodate the laser fluence attenuation in deeper tissues, the diagnosis process was further modified by applying two pulses in the same location, the next pulse having a higher fluence (FIG. 4A). The PNB generation threshold fluence remains the same at any tissue depth, around 10-15 mJ/cm$^2$, since the threshold at a specific laser wavelength is determined only by the size of the gold cluster. This PNB threshold, coupled with the attenuation of the laser fluence with depth, determines the maximal depth of PNB generation under a specific fluence (FIG. 4B). FIG. 4B shows the maximal tissue depth of PNB generation at the two different fluences E1 and E2>E1: the first laser pulse generates PNB s within 1 mm depth at the fluence E1, the second pulse at the fluence E2 generates PNBs within the depth range from 1 mm to 3 mm. During the second pulse, no PNBs or only small ones are generated by those cancer cells which already responded with PNBs to the first pulse because the gold cluster is usually destroyed (mechanically scattered) by the PNB (1320 in FIG. 13), and single scattered nanoparticles cannot generate PNB s under the same fluence as efficiently as clusters can. Thus, the following pulse of the higher fluence probes the deeper layer with PNBs (FIG. 4B). The laser pulse energy can be automatically switched in real time (within milliseconds) during the laser operation. In addition, the PNB generation depth is independently monitored via the time-delay from the laser pulse to the PNB spike in the time-response (FIG. 4C). This simple diagnosis process does not require signal reconstruction (unlike photoacoustic diagnosis processes) because both the PNB signal amplitude and time-delay are directly read from the primary signal. In this multi-pulse mode, PNBs not just detect deeper micro-tumors, but will also indicate the depth of the MRD, thus helping a surgeon to plan the follow-up resection.

Example 9: Intraoperative Detection and Elimination of MRD In Vivo with PNBs

The intraoperative application of PNBs depends upon the successful clustering of gold conjugates in cancer cells. In this example, systemic mechanism of in vivo gold clustering was optimized. For the combination of 60 nm gold spheres covalently conjugated to Panitumumab antibody (FIG. 10A), gold dose 4 mg/kg, time after gold injection 24 h and primary tumour size around 5 mm (FIG. 10B), both a high accumulation and specificity of gold in the tumor (FIG. 9A) were achieved. The antibody-specific "liver sink" effect, tested by comparing the gold biodistribution of anti-human and anti-mouse antibody conjugates (FIG. 9A) did not significantly influence the systemic delivery of the gold to the tumor. Although colloidal gold is clinically-safe, its short- and long-term safety in vivo (FIGS. 9B-9G) was additionally verified.

Figure 15B:
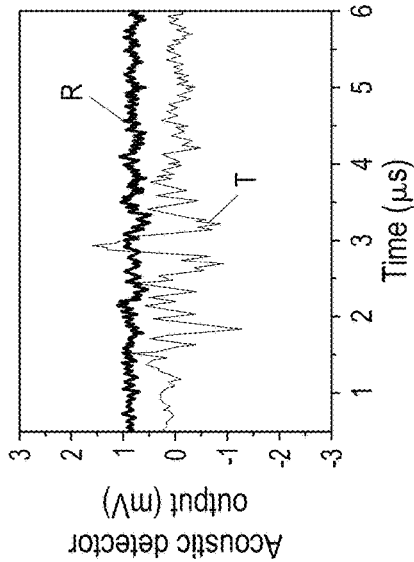
FIG. 15B illustrates exemplary acoustic time-responses to single laser pulses obtained immediately after the primary surgery in FIG. 15A at a location of possible MRD and at a MRD-negative location.

Twenty-four hours after systemic administration of gold conjugates, PNBs were applied for the intraoperative detection and elimination of MRD in animal groups that modelled resectable and unresectable MRD. After gross resection of the primary tumor (FIG. 15A), the animals were split into three groups (1: standard surgery, 2: standard surgery+PNBs in unresectable MRD, 3: PNB-guided standard surgery in resectable MRD). After surgery, all animals were monitored for local tumor recurrence and survival.

Figure 15A:
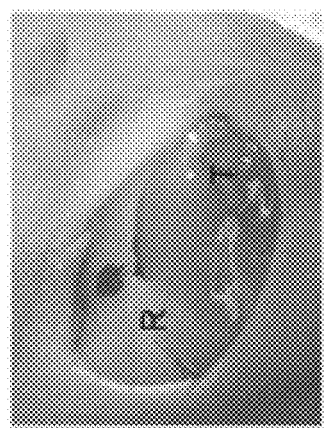
FIG. 15A illustrates an exemplary image of a surgical bed after a primary surgery.
Figure 16B:
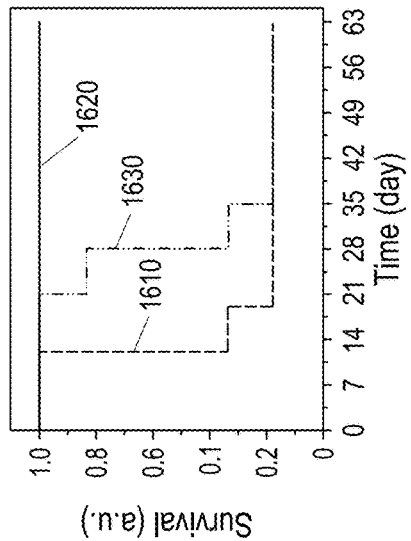
FIGS. 16A-D illustrate exemplary improvement in PNB-guided surgical outcome in both resectable and unresectable MRDs.

In Group 2 (unresectable MRD), after resecting the primary tumor, the surgical bed was scanned with PNB probe and acoustic time-responses to each pulse were collected in real time (see the surgical process shown in FIG. 6). Reference, tumor-free, signals obtained outside the tumor nest did not report PNBs (FIG. 15B, corresponds to the location marked "R" in FIG. 15A). The signals obtained inside the tumor nest reported PNB-specific spikes (FIG. 15A, corresponds to the location marked "T" in FIG. 15A) in some locations within a tumor nest in five animals (83%). These animals were intraoperatively diagnosed with PNBs as MRD-positive after primary surgery. In this group, no PNB-guided resections were applied, and thus the only treatment was the mechanical impact of PNBs. We named this mode "PNB nano-surgery". Compared to standard surgery (Group 1), PNB nano-surgery delayed local tumor recurrence (FIG. 16A) and improved animal survival by more than two-fold (FIG. 16B). The mechanical impact of PNBs destroyed cancer cells. The high cancer cell selectivity of this mechanical destruction can be clearly seen in the mixture of HNSCC and normal cells identically treated with gold conjugates and a single broad laser pulse. In response to a single laser pulse, a cancer cell literary explodes while adjacent normal cells remain unharmed. The intraoperative diagnostic PNBs did not destroy all residual cancer cells because the PNBs in some cancer cells did not reach the lethal size, while they still were able to report those cells acoustically. The surgical outcome can be further improved in this case by increasing the fluence of the laser pulse. Nevertheless, PNB nano-surgery significantly improved the surgical outcome in the most clinically challenging case of unresectable MRD.

Figure 15D:
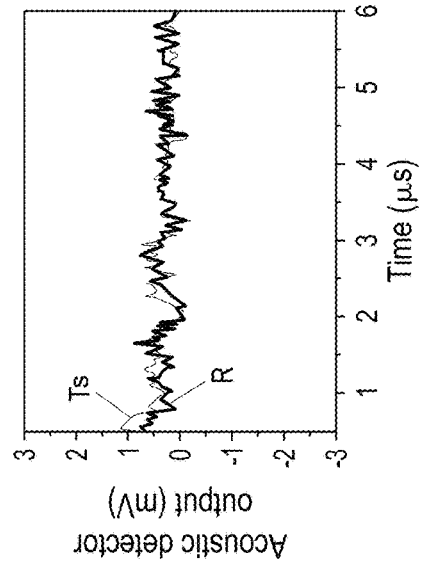
FIG. 15D illustrates exemplary acoustic time-responses obtained after the PNB-guided surgery in FIG. 15C in a location of secondary resections and in an initially MRD-negative location.
Figure 15C:
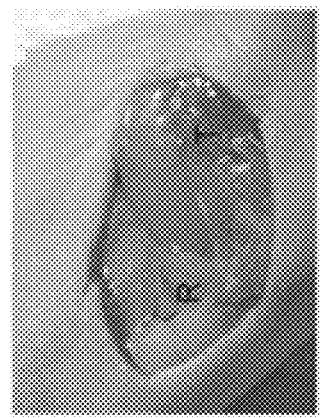
FIG. 15C illustrates an exemplary image of a surgical bed after a PNB-guided surgery.

PNB-guided surgery of resectable MRD was tested in Group 3 (see the surgical process shown in FIG. 5). After the primary resection, time-responses to single laser pulses were obtained for tumor-free location ("R" in FIG. 15C) and for a tumor nest ("T" in FIG. 15C). Each PNB-positive location in the surgical bed was interpreted as MRD-positive and was subsequently further resected at 1 mm depth and 3×3 mm footprint. (FIG. 15C). After this local secondary resection, an acoustic time-response Ts was obtained again at the same location. If a PNB-positive signal was detected, additional local resection was applied again until the acoustic time-response became PNB-negative (FIG. 15D). On achieving PNB-negative time-responses in all locations (within a few minutes), wounds were closed and the animals were monitored for tumor recurrence and survival. In this group, no recurrence was observed (FIG. 16A) and complete tumor-free survival was achieved for 100% of the animals (FIG. 16B).

Figure 16D:
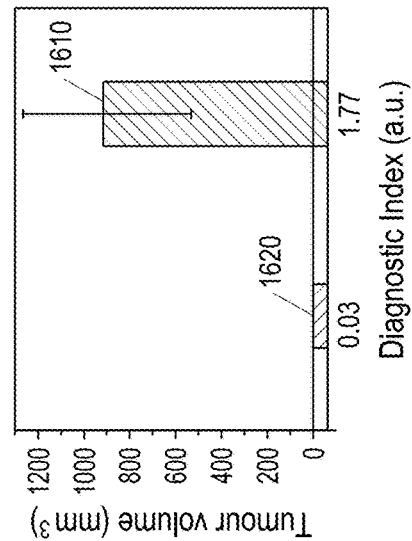
Figure 16A:
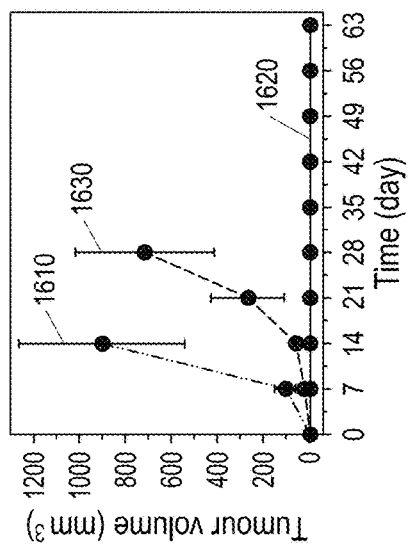
Figure 16C:
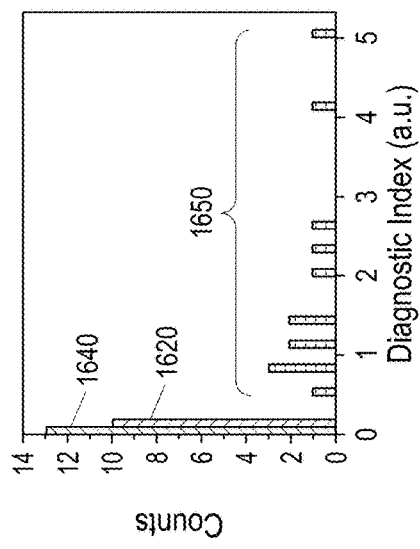

In these examples, PNBs demonstrated the unique intraoperative combination of both detecting and eliminating MRD. To determine the prognostic potential of intraoperative PNBs, we compared the Diagnostic Indexes for MRD-positive (FIG. 16C) and -negative locations (FIG. 16C) after primary surgery, and after secondary PNB-guided resections (FIG. 16C). The Diagnostic Indexes after PNB-guided resections almost coincided with those for MRD-negative tissue (FIG. 16C), thus indicating in real time the possible elimination of MRD. These intraoperatively-obtained Diagnostic Indexes were followed up by the volumes of recurrent tumors in groups treated with standard and PNB-guided surgeries (FIG. 16D). Local recurrence was associated with high Diagnostic Index (FIG. 16D). In contrast, no recurrence was associated with zero Diagnostic Index (FIG. 16D). Thus this PNB metric may serve as a prognostic index to predict the surgical outcome. As in the previous in vivo experiment, no burns or other laser- or PNB-related damage to the surgical bed in both PNB modes was observed. This experiment revealed the ability of PNBs to manage both resectable and unresectable MRDs: (1) the in vivo diagnosis of MRD with high speed and cancer specificity; (2) the prognosis of surgical outcome; (3) the improved therapeutic efficacy and reduced morbidity of standard surgery in resectable cases (which completely cured animals); and (4) the improved outcome in unresectable cases when PNBs support a "nano-surgery" mode.

Example 10: Verification of Cancer Cell Selectivity of PNBs

Unlike other thermal or mechanical events, the mechanical impact of PNB is localized within the cell where the PNB is generated and is precisely controlled with the fluence of the laser pulse. According to this data, a surface fluence of 70 mJ/cm$^2$ is safe to normal cells and even allows further increase in the fluence. In the in vitro clonogenic study of HN31 and normal cells, their identical treatment with gold and laser pulses resulted in high safety and viability of normal cells up to the laser pulse fluence levels of 140 mJ/cm$^2$ (while cancer cells were effectively destroyed with the mechanical impact of intracellular PNBs). This single cancer cell specificity of the mechanical impact of PNBs was tested in a simple experiment with the mixture of identically gold- and laser-treated normal and HNSCC cells. In this experiment, cancer and normal cells were identically pretreated in vitro with gold conjugates as described above, and 24 h later were mixed and exposed to a single broad laser pulse (which simultaneously irradiated both normal and cancer cells). Only a cancer cell explodes while adjacent normal cells remain intact and survive the laser impact and the generation of the PNB in cancer cell. This cluster-threshold PNB mechanism was verified in vivo in the primary tumor model described above. The gold cluster size was correlated with PNB metrics for tumors and normal tissues: the cluster size in vivo (directly measured with TEM in the tumor and normal adjacent tissue) was correlated to the PNB lifetime in the tissue slices harvested from a tumor and normal adjacent tissue and the amplitude of acoustic time-response. Both PNB metrics revealed the high tumor specificity of PNBs which correlated to the TEM data for gold clusters. This result was in line with the dependence of the PNB generation threshold upon the gold cluster size: the lowest around large clusters (in tumors) and the highest around single nanoparticles in adjacent normal tissue. In the current study, the gold clustering method was further verified with the results of the PNB diagnostics (FIGS. 15A-15D) and the PNB-guided surgical outcome (FIGS. 16A-16B: no PNBs would have been generated otherwise around non-clustered single gold nanoparticles). The animal group-averaged metrics of local recurrent tumors after standard surgery with resectable MRD (1610, n=6), PNB-guided surgery of resectable MRD (1620, n=5) and PNB nano-surgery of unresectable MRD (1630, n=6) show a significant improvement in the outcome in both resectable and unresectable cases when the surgery is enhanced with PNBs. FIG. 16A illustrates tumor volume versus time after the surgery. FIG. 16B illustrates animal survival rate versus time after the surgery. FIG. 16C illustrates histograms of the Diagnostic Index obtained in MRD-positive 1650 and -negative 1640 locations after standard surgery and for the MRD-positive locations 1620 after PNB-guided surgery. FIG. 16D illustrates recurrent tumor volumes plotted for the group-averaged Diagnostic Indexes after standard 1610 and PNB-guided 1620 surgery show the prognostic potential of PNBs to intraoperatively predict tumor recurrence. Thus, the gold cluster-threshold mechanism of PNB generation successfully overcomes the problem of non-specific uptake of nanoparticles by normal tissues (this problem remains the major limitation in the specificity of all material-based diagnosis processes).

Example 11: Comparison of MSOT (Multi-Spectral Optoacoustic Tomography) and PNB (Plasmonic Nanobubble) Technologies for In Vivo Intra-Operative Management of MRD (Residual Micro-Tumors) in Solid Tissues in a Surgical Bed As shown in the table below, multi-spectral optoacoustic tomography (MSOT) is not sensitive or fast enough to detect MRD (which can be represented by tens of cancer cells) in vivo in solid tissue in real time, and did not show a good surgical outcome in MRD applications when compared to the PNB technology for in vivo intraoperative management of MRD.

| Parameter/property | MSOT (as report in NPL references) | PNB |
| --- | --- | --- |
| Intraoperative MRD detection in vivo (in surgical bed) in solid tissue | Not reported | Yes, compatible with standard surgery |
| Influence on the surgical outcome (local recurrence and overall survival) | Not reported | Yes, multi-fold improvement in survival in resectable and unresectable cases |
| Tumour detection sensitivity in solid tissue in vivo | >1 mm, >2500 cells (mouse macrophages) | Single cells and microtumours of size << 1 mm (undetectable with standard pathology) |
| Time to result in vivo for solid tissue | 150 µs - 20 min, not reported for MRD | <10 µs per location (detection), less than 1 min per 2 × 2 cm surgical bed (including the surgery involved) |
| Requirements for diagnostic agents | Several different dyes or nanoparticles | Single type clinically-validated agent - colloidal gold |

-continued

| Parameter/property | MSOT (as report in NPL references) | PNB |
| --- | --- | --- |
| Requirements for laser radiation | Several laser beams with different wavelengths, multiple pulses | Single laser beam, single pulse, single wavelength |
| Complexity of signal interpretation | High: Reconstruction and processing of primary signals required | Low: Direct measurement of the amplitude of primary signal |

Example 12: Elimination of TMD

Figure 18:
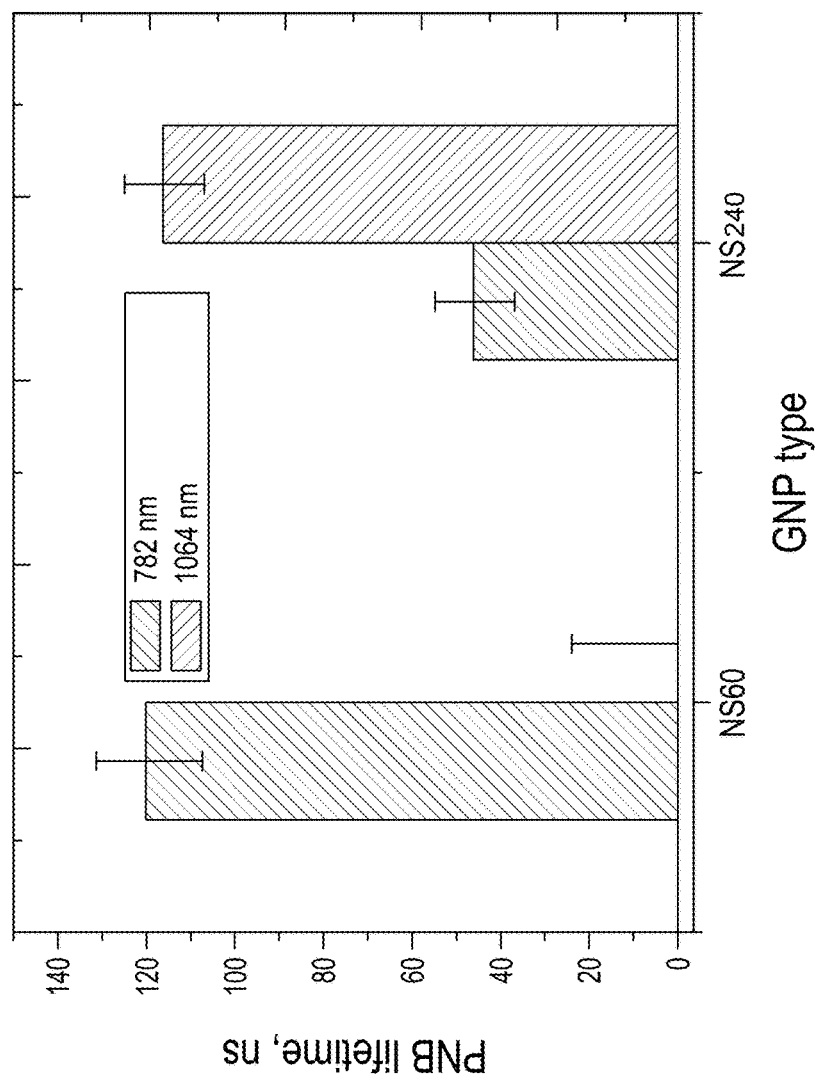
FIG. 18 illustrates exemplary PNB lifetimes of nanoparticles of different sizes and under different laser pulse energy levels.

New clinically-relevant gold spheres (240 nm) were tested in HNSCC cancer cells for the generation of PNBs on the epithelial wall of the tumor-specific vasculature under excitation with a 1064 nm laser pulse. Compared to the 782 nm pulses/60 nm nanoparticles, the tissue penetration depth can be improved 2-3 fold, and technical complexity of the laser reduced by half without increasing the cost of the laser system. New nanoparticle/laser wavelength combination showed the efficacy similar to that for the combination of 782 nm laser pulses/60 nm nanoparticles, as illustrated by the lifetime of PNBs generated in cancer cells treated with standard and new combination in FIG. 18. Laser pulses at 1064 nm are more available, less expensive and can deliver 10× fold energy compared to 782 nm laser pulses. This is the new option that requires specific nanoparticles with high PNB generation efficacy at 1064 nm. It is possible that higher energy at lower cost (10% of that for current 782 nm) will support deeper tissue penetration at 1064 nm and hence will improve the therapeutic efficacy of the mono PNB therapy.

Additional embodiments of the present disclosure, such as system and process for intraoperatively detecting and precisely eliminate TME including but not limited to tumor blood vasculature are provided in Appendices A and B. In one embodiment, vasculature-specific bioconjugated nanoparticles are administered to tissue. The bioconjugated nanoparticles comprise nanoparticles conjugated with vascular-specific ligands. After a predetermined time delay, such as 24 hours, laser pulses with a wavelength or fluence sufficient for creating vasculature-specific PNBs are applied to the tissue to cause destruction of tumor-vasculature.

Although the foregoing has been described in terms of certain specific embodiments, other embodiments will be apparent to those of ordinary skill in the art from the disclosure herein. Moreover, the described embodiments have been presented by way of example only, and are not intended to limit the scope of the disclosure. Indeed, the novel methods and systems described herein may be embodied in a variety of other forms without departing from the spirit thereof. Accordingly, other combinations, omissions, substitutions, and modifications will be apparent to the skilled artisan in view of the disclosure herein. Thus, the present disclosure is not limited by the disclosed embodiments, but is defined by reference to the appended claims. The accompanying claims and their equivalents are intended to cover forms or modifications as would fall within the scope and spirit of the disclosure.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

APPENDIX A

Intraoperative diagnostics and elimination of residual micro-tumours with plasmonic nanobubbles Ekaterina Y. Lukianova-Hleb[1,*], Yoo-Shin Kim[2,*], Ihor Belatsarkouski[3], Ann M. Gillenwater[4], Brian E. O'Neill[2], Dmitri O. Lapotko[1]

[1]Department of BioSciences at Rice, Rice University, Houston, TX 77005 USA; [2]Department of Translational Imaging, Methodist Hospital Research Institute, Houston, TX 77030 USA; [3]N.N. Alexandrov National Cancer Centre of Belarus, Minsk, 223040 Belarus; [4]Department of Head and Neck Surgery, The University of Texas MD Anderson Cancer Center, Houston, TX 77030 USA;

[*]Contributed equally to this work.

Abstract

Failure of cancer surgery to intraoperatively detect and eliminate microscopic residual disease (MRD) causes lethal recurrence and metastases, whereas removal of important normal tissues causes excessive morbidity. Here, we show that plasmonic nanobubble (PNB), a non-stationary laser pulse-activated nano-event, intraoperatively detects and eliminates MRD in the surgical bed. PNBs were generated *in vivo* in head and neck cancer cells by systemically targeting tumours with gold colloids and locally applying near-infrared low energy short laser pulses, and were simultaneously detected with an acoustic probe. In mouse models, from 3 to 30 residual cancer cells and MRD (undetectable with current methods) were non-invasively detected up to 4 millimetres deep in the surgical bed within 1 millisecond. In resectable MRD, PNB-guided surgery prevented local recurrence and delivered 100% tumour-free survival. In unresectable MRD, PNB nano-surgery improved survival by two-fold compared to standard surgery. Our results show that PNB-guided surgery and nano-surgery can rapidly and precisely detect and remove MRD in simple intraoperative procedures.

Key words: plasmonic nanobubble, laser pulse, cancer, surgery, diagnostics, microscopic residual disease Despite continuous improvements in onco-surgery, residual micro-tumours (microscopic residual disease - MRD) remain a significant problem. In many aggressive cancers, including head and neck squamous cell carcinoma (HNSCC), lung and breast cancer, and sarcomas, what appears to be a complete tumour resection may leave MRD behind, often as small as tens of cancer cells, that later causes lethal recurrence. Clinical standards such as palpation and radiographic imaging are not sensitive enough to detect MRD. Pathological analysis of surgical margins,[1] the only currently available MRD diagnostics, is slow, often inaccurate and not always available.[2,3] As a result, surgeons routinely resect large margins of normal tissue to remove potential MRD. Unfortunately, this approach often fails,[4,5] causes high morbidity and reduces patients' quality of life and eligibility.[6,7] Post-operative radiation[8,9] or chemoradiation therapies[10,11] further increase the morbidity, treatment cost and reduce patients' quality of life. Further, MRD often becomes highly resistant to radiation or chemotherapy[9,10] resulting in poor survival.

Although new diagnostic technologies are being developed, they still cannot detect MRD in solid tissue *in vivo* with single cancer cell sensitivity and in real time. As a result, their gain in reduction in local recurrence and improvement in overall survival remains limited for MRD-complicated surgeries. Optical approaches improved cancer detection *in vivo*[12-17] including intraoperative fluorescent[18-22] and optical scattering diagnostics[23,24], but they detect only relatively large tumours at the surface while MRD can be located deeper in tissue and can be of a microscopic size. Photoacoustic methods detect tumours in depths up to 10-20 mm although with limited sensitivity in solid tissue (> 1000 cells),[13] speed[12,13] and specificity[13] for intraoperative detection of MRD in a surgical bed. Radio-fluorescent methods[17] can detect deeper tumours but are not sensitive enough for MRD detection. Multi-spectral optoacoustic tomography[24-26] (Supplementary Table 1) is used intraoperatively, but is not sensitive or fast enough to detect MRD (which can be represented by tens of cancer cells) *in vivo* in solid tissue in real time, and did not show a good surgical outcome in MRD applications. Furthermore, standard surgery often cannot remove MRD even when identified by frozen section pathology without causing too high morbidity because MRD infiltrates into critical organs. Thus, the ability to intraoperatively detect and precisely eliminate MRD *in vivo* in real time in resectable and in unresectable cases would significantly improve the treatment outcome, treatment eligibility and quality of life for cancer patients and would reduce surgical morbidity.

We have recently reported cancer cell-specific mechanical nano-events, plasmonic nanobubbles (PNBs),[27,28] transient vapour nanobubbles generated around an intracellular clusters of gold nanoparticles in response to a short laser pulse.[29-34] To generate a PNB, a gold nanoparticle cluster absorbs a short near-infrared (NIR) laser pulse, converts its energy via non-stationary plasmonic mechanism into localized heat[27,30], which evaporates adjacent liquid into an expanding and collapsing vapour nanobubble of nanosecond life-span. Unlike most diagnostic probes, PNBs are not materials, but on-demand threshold-activated nonstationary nano-events. The PNB generation threshold energy of a laser pulse is the lowest for largest clusters of gold nanoparticles, which are self-assembled by cancer cells through endocytosis of antibody-conjugated nanoparticles[27,33]. For single nanoparticles or their small clusters which are non-specifically accumulated by normal cells, the PNB generation threshold energy is much higher[27,29,35]. This cluster-threshold mechanism of PNB generation overcomes the problem of non-specific uptake of nanoparticles by selectively generating PNB at low laser energy only in cancer cells and not in adjacent normal cells or tissues[27,35,36]. A PNB reports a cancer cell by emitting a pressure pulse which is detected acoustically. PNBs can be generated in cancer cells by using clinically validated gold colloids[37-39] (conjugated to clinical antibodies against cancer-specific receptors).

Here, we report a PNB surgical technology for the intraoperative management of both resectable and unresectable tumours through the local detection and resection of resectable MRD or the mechanical destruction of unresectable MRD with cancer cell-specific PNBs. In both cases, PNBs improve surgical outcome and reduce morbidity through the real-time point-of-care *in vivo* detection of MRD, reduction in the resected volume of surgical margin to that of PNB-positive signal and selective destruction of only cancer cells without damaging adjacent critical structures and cells. The technology uses systemic gold targeting (to form gold clusters in tumours, Fig. 1a-c), local PNB generation with single low energy laser pulse and acoustic detection (Fig. 1d) with standard surgery to intraoperatively detect and resect MRD in resectable cases, or to detect and mechanically eliminate MRD at microscale in unresectable cases. The high cancer cell sensitivity and specificity of PNBs *in vivo*,[27,36] coupled with their acoustic detection, mechanical impact and compatibility with standard surgical protocols, may provide efficient surgical management of both resectable and unresectable MRD. To determine the translational potential of PNBs in onco-surgery, we used HNSCC as a model due to the high lethality of its local recurrence, and the surgical challenges in MRD detection and elimination.

1. Plasmonic nanobubble (PNB) diagnostic mechanism. To establish a PNB diagnostic mechanism, PNBs were first generated and detected in individual gold-pretreated (60 nm spheres conjugated to Panitumumab) HNSCC cells in transparent media. PNBs were simultaneously detected optically and acoustically in response to a single laser pulse (782 nm, 30 ps) of variable fluence above the PNB generation threshold (which was found to be 10-15 mJ/cm$^2$ for gold-pretreated HNSCC cells). Above the threshold fluence, the optical signal typical for PNBs (Fig. 2a, red) coincided with a bipolar spike in the simultaneously detected acoustic time-response (Fig. 2b, red). No PNBs and no spikes were detected in intact (not pretreated with gold) cells under the same pulses (Fig. 2a,b, black). The amplitude of the acoustic bipolar spike almost linearly correlated to the optically measured PNB lifetime, the metric of the PNB maximal diameter[29] (Fig. 2c). Therefore, bipolar spikes in detected acoustic time-responses were attributed to PNBs (see Methods section for details). This *in vitro* experiment established the principle of the acoustic detection of PNBs in single cancer cells.

Next, transparent cell media was replaced by a chicken breast to model intraoperative conditions of solid tissue (Fig. 2d). Gold-pretreated cancer cells were injected one by one with a nano-syringe into the tissue at a specific depth of 1 mm or 3-4 mm. A single laser pulse (782 nm, 30 ps, 70 mJ/cm$^2$, 4 mm diameter) was applied via an endoscope, and the acoustic time-response to each laser pulse was obtained with an ultrasound probe. The injection of three gold-pretreated cancer cells produced a PNB-specific spike in the acoustic time-response (Fig. 2e, red). No such spikes were observed after the injection of the same and a higher number of intact cells (Fig. 2e, black). These spikes obtained for gold-pretreated cells were similar to those obtained for PNBs in the previous experiment, and therefore were attributed to PNBs and, in this case, reported single cancer cells in solid tissue. The injection of 10 and more cells returned multiple spikes in acoustic time-responses (Supplementary Fig. 1, red). The temporal separation of spikes in one time-response implied that the cells were spatially distributed over 2-3 mm distance in the direction of the probe axis. Thus, a single time-response reported multiple cells in different locations within the footprint of a single laser pulse. The detection procedure took about 1 ms. Next, the Diagnostic Index (the relative increase in the amplitude of the test time-response versus that of the reference, cancer-free, time-response) obtained for each cell injection was analysed as function of the number of injected gold-pretreated cancer cells and their depths in the tissue (Fig. 2f). The Diagnostic Index was nearly proportional to the number of injected cells in the range of 3 to 100 cells. At 1 mm depth, PNBs reported single cancer cells with good signal-to-background ratio. At 4 mm depth, the detection threshold increased to 30 cells. These experiments established the PNB diagnostics mechanism for residual cancer cells in solid tissue at the depth comparable to that for surgical margins.

**2. *In vivo* intraoperative detection of cancer cells. Individual gold-pretreated or intact cancer cells (3 and 10) were injected to the depth of 1 mm into the surgical bed of an anesthetized mouse (Fig. 3a, Supplementary Fig. 2). Prior to and following each injection, a single laser pulse (782 nm, 30 ps, 70 mJ/cm$^2$, 4 mm diameter) was applied to the injection area. The acoustic time-response to the pre-injection pulse was used as a cancer-free reference signal (Fig. 3b, black) and the acoustic time-response to the post-injection pulse was used as a test signal. We observed PNB-specific spikes (similar to those described above for individual gold-pretreated cancer cells) after the injection of three gold-pretreated cancer cells (Fig. 3b, red). For ten cells, a multi-peak time-response was detected (Fig. 3c, red) meaning that the cells were distributed over a distance of 2-3 mm in the direction of the probe axis. Pre-injection reference signals (black in Fig. 3b,c,d**) showed minor peaks not observed in the *in vitro* model and could have been caused by the bulk photothermal effect in blood.[12] This bulk effect cannot produce vapour nanobubbles (in contrast to the highly localized photothermal effect of gold clusters in cancer cells) and delivered almost identical pre- (black, Fig. 3d) and post-injection (red, Fig. 3d) signal components in time-responses of intact cells which produced no PNBs. With no false-positive signals detected for untreated cells, and no false-negative signals detected for even three gold-pretreated cells, the PNBs were highly cancer cell-specific, as can be seen from the values of the Diagnostic Index the as function of the number of cells and their gold pretreatment (Fig. 3e). Thus the detected PNB-positive signals were attributed to residual cancer cells in solid tissue. The time to result was within 1 ms per location of the probe. Laser pulses caused no detectable damage to the irradiated tissue in the surgical bed due to a relatively low cumulative dose (70 mJ/cm$^2$), which is well below the optical doses associated with non-invasive *in vivo* imaging. The safety of laser pulses and the selectivity of even large lethal PNBs can be additionally seen from the response of the cancer-normal cell mixture, identically pretreated with gold and exposed to a single broad laser pulse (Supplementary Movie 1): even when a PNB explodes a cancer cell, surrounding normal cells survive. This high selectivity of PNBs has recently been verified for even higher laser fluences up to 140 mJ/cm$^2$ (Fig 3b in ref. 27).

3. Intraoperative detection and elimination of MRD *in vivo* with PNBs.

The intraoperative application of PNBs depends upon the successful clustering of gold conjugates in cancer cells. In this study, we optimized systemic mechanism of *in vivo* gold clustering[27,36] (see the Methods section for details). For the combination of 60 nm gold spheres covalently conjugated to Panitumumab antibody (Supplementary Fig. 3a), gold dose 4 mg/kg, time after gold injection 24 h and primary tumour size around 5 mm (Supplementary Fig. 3b), we achieved both a high accumulation and specificity of gold in the tumour (Fig. 4a). The antibody-specific "liver sink" effect[40], tested by comparing the gold biodistribution of anti-human and anti-mouse antibody conjugates (Fig. 4a) did not significantly influence the systemic delivery of the gold to the tumour. Although colloidal gold is clinically-safe[37-39], we additionally verified its short- and long-term safety *in vivo* (Fig. 4b-g).

Twenty-four hours after systemic administration of gold conjugates, PNBs were applied for the intraoperative detection and elimination of MRD in animal groups that modelled resectable and unresectable MRD. After gross resection of the primary tumour (Fig. 5a), the animals were split into three groups (1: standard surgery, 2: standard surgery + PNBs in unresectable MRD, 3: PNB-guided standard surgery in resectable MRD). After surgery, all animals were monitored for local tumour recurrence and survival.

In Group 2 (unresectable MRD), after resecting the primary tumour, the surgical bed was scanned with PNB probe and acoustic time-responses to each pulse were collected in real time (see the Methods section for the detailed algorithm, Supplementary Fig. 5a).

Reference, tumour-free, signals obtained outside the tumour nest did not report PNBs (Fig. 5b, black, corresponds to the location marked "R" in Fig. 5a). The signals obtained inside the tumour nest reported PNB-specific spikes (Fig. 5b, red, corresponds to the location marked "T" in Fig. 5a) in some locations within a tumour nest in five animals (83%). These animals were intraoperatively diagnosed with PNBs as MRD-positive after primary surgery. In this group, no PNB-guided resections were applied, and thus the only treatment was the mechanical impact of PNBs. We named this mode "PNB nano-surgery". Compared to standard surgery (Group 1), PNB nano-surgery delayed local tumour recurrence (Fig. 6a, red) and improved animal survival by more than two-fold (Fig. 6b, red). The mechanical impact of PNBs destroyed cancer cells (a mechanism we studied in detail previously[27,28,41]. The high cancer cell selectivity of this mechanical destruction can be clearly seen in the mixture of HNSCC and normal cells identically treated with gold conjugates and a single broad laser pulse (Supplementary Movie). In response to a single laser pulse, a cancer cell literary explodes while adjacent normal cells remain unharmed. Our intraoperative diagnostic PNBs did not destroy all residual cancer cells because the PNBs in some cancer cells did not reach the lethal size, while they still were able to report those cells acoustically. Based upon our recent *in vitro* studies of the same HNSCC cells (Fig. 3b in ref. 27), the surgical outcome can be further improved in this case by increasing the fluence of the laser pulse. Nevertheless, PNB nano-surgery significantly improved the surgical outcome in the most clinically challenging case of unresectable MRD.

PNB-guided surgery of resectable MRD was tested in Group 3 (see the Methods section for the detailed algorithm, Supplementary Fig. 5b). After the primary resection, time-responses to single laser pulses were obtained for tumour-free location ("R" in Fig. 5c) and for a tumour nest ("T" in Fig. 5c). Each PNB-positive location in the surgical bed was interpreted as MRD-positive and was subsequently further resected at 1 mm depth and 3x3 mm footprint. (Fig. 5c). After this local secondary resection, an acoustic time-response was obtained again at the same location. If a PNB-positive signal was detected, additional local resection was applied again until the acoustic time-response became PNB-negative (Fig. 5d, green). On achieving PNB-negative time-responses in all locations (within a few minutes), wounds were closed and the animals were monitored for tumour recurrence and survival. In this group, no recurrence was observed (Fig. 6a, green) and complete tumour-free survival was achieved for 100% of the animals (Fig. 6b, green).

In these experiments, PNBs demonstrated the unique intraoperative combination of both detecting and eliminating MRD. To determine the prognostic potential of intraoperative PNBs, we compared the Diagnostic Indexes for MRD-positive (Fig. 6c, red) and -negative locations (Fig. 6c, black) after primary surgery, and after secondary PNB-guided resections (Fig. 6c, green). The Diagnostic Indexes after PNB-guided resections almost coincided with those for MRD-negative tissue (Fig. 6c, black), thus indicating in real time the possible elimination of MRD. These intraoperatively-obtained Diagnostic Indexes were followed up by the volumes of recurrent tumours in groups treated with standard and PNB-guided surgeries (Fig. 6d). Local recurrence was associated with high Diagnostic Index (Fig. 6d, blue). In contrast, no recurrence was associated with zero Diagnostic Index (Fig. 6d, green). Thus this PNB metric may serve as a prognostic index to predict the surgical outcome.

As in the previous *in vivo* experiment, we did not observe any burns or other laser- or PNB-related damage to the surgical bed in both PNB modes. This experiment revealed the ability of PNBs to manage both resectable and unresectable MRDs: (1) the *in vivo* diagnosis of MRD with high speed and cancer specificity; (2) the prognosis of surgical outcome; (3) the improved therapeutic efficacy and reduced morbidity of standard surgery in resectable cases (which completely cured animals); and (4) the improved outcome in unresectable cases when PNBs support a "nano-surgery" mode.

4. Translating PNBs to clinic

Combining the intraoperative detection of single cancer cells in a surgical bed, real-time elimination of MRD and prediction of the surgical outcome is the ultimate dream for surgical oncologists. Our PNB nanotechnology achieves this multi-functionality through its high cancer cell sensitivity, specificity, speed and translational potential. The single cancer cell sensitivity of PNBs (compared to that of photoacoustic, multi-spectral optoacoustic tomography and optical methods[12-26]) results from (1) the high efficacy of PNB generation by gold clusters, 10-100 fold higher than single nanoparticles[27,29], (2) much higher pressure produced by the rapid expansion and collapse of a vapour nanobubble[42,43] than the thermo-elastic effect in nanoparticles employed by photoacoustic methods[12,13,26,] and (3) using the non-stationary PNB mechanism with a short laser pulse[30,44] which provides efficient excitation of clinically safe colloidal gold with deep tissue-penetrating near-infrared laser pulse, a combination not possible in photoacoustic methods or under stationary optical excitation. Of course, the diagnostic sensitivity decreases with the tissue depth but even at 4 mm it is sufficient for detecting 30 residual cancer cells, which is equivalent to tumours below 50 um size. The high cancer cell specificity of PNBs is based on the cluster-threshold mechanism of PNB generation, not only on the antibody-directed targeting of nanoparticles as in other methods (see Introduction and Methods sections for details). This, in turn, also significantly reduces the nanoparticle dose (1-10% of the doses employed by photoacoustic, photothermal or computer tomography methods).[12-14,37,45] Such a low nanoparticle dose can be safely delivered to the tumour.[27] The clustering of gold conjugates in cancer cells, a step critical for generating PNBs only in cancer cells with laser pulses of low energy, has recently been validated *in vivo* in the same tumour model with transmission electron microscopy and PNB studies[36] for systemically administered gold colloids. All the above, coupled with clinically validated modalities – gold colloids,[37-39] near-infrared low-energy laser pulses and clinically-approved antibodies, ensure the high clinical translational potential of PNBs.

In clinic, PNB surgical algorithms (Supplementary Fig. 5) can be integrated into manual, endoscopic or robotic surgery by using a standalone PNB probe or integrating it with surgical endoscope or robotic arm, and support the detection and elimination of MRD in solid tissue in surgical bed in seconds. In resectable tumours, PNB-guided surgery resects only the source of the PNB signal, a small volume of, for example, 3x3x2 mm, in the "test-cut-test" algorithm until the PNB signal indicates tumour-free margin. This volume is 10- to 50-fold smaller than that routinely resected with standard surgery to achieve negative margins (up to 10x10x10 mm). Thus PNBs spare adjacent important structures and make surgery less morbid. In unresectable therapy-resistant tumours, PNB-induced selective mechanical destruction of residual cancer cells not only improves the surgical outcome, but also replaces toxic chemo- and radiation therapies thus improving the quality of patients' life and making surgical treatment possible for currently ineligible patients.

To conclude, our PNB nano-surgery can improve standard onco-surgery through: (1) Real-time intraoperative local detection of MRD *in vivo* with very high sensitivity and specificity; (2) Real-time guidance of surgery to precisely eliminate resectable MRD with minimal morbidity by resecting only PNB-positive volume instead of a larger volume; (3) Intraoperative selective elimination of unresectable MRD through the mechanical impact of lethal cancer cell-specific PNBs without damaging adjacent normal cells and tissues; (4) Prediction of the surgical outcome through the metrics of PNB signals.

Methods

Cancer models and characterization. HNSCC is a very aggressive and lethal cancer whose surgery is challenged by resectable and unresectable MRD which later often cause lethal local recurrence.[8] This cancer was modelled with aggressive and resistant HN31 cells[46] obtained from J. Myers' laboratory, UT MD Anderson Cancer Center (Houston, TX) and tested for mycoplasma contamination before their use. HNSCC overexpress Epidermal Growth Factor Receptor, against which there is a clinically-approved antibody, Panitumumab.[10,47] We used four cancer models of increasing complexity. To verify acoustic detection of PNBs, we used intact or gold conjugate-pretreated HNSCC cells in transparent media (model 1). To study acoustic detection of cancer cells in solid tissue (model 2), we injected a precise amount of gold conjugate-pretreated cancer cells into a specific depth of a chicken breast with a nano-syringe. In the 3rd, *in vivo* model, pretreated and intact cancer cells were similarly injected into the surgical bed of anesthetized mice (athymic nude, strain CRL-490, 6 weeks age). To study the intraoperative detection and elimination of MRD (model 4), a deeply-seeded xenograft HNSCC tumour was established in the mouse. The tumour was grown to 5-6 mm size to ensure its infiltration into the normal tissue underneath and to achieve a mature vascularization (important for the systemic delivery of gold conjugates). To establish MRD intraoperatively, the tumour was grossly resected using aseptic surgery. The nest of the resected primary tumour was considered to have MRD as had been verified previously by observing almost 100% local recurrence after resecting the primary tumour.[27] The area of the surgical bed outside a > 3 mm margin around the tumour nest was considered as MRD-negative location. Presence of MRD after resection of the primary tumour was confirmed with standard pathology (Supplementary Fig. 4) and later by observing local recurrence. After the PNB and surgical procedures in MRD-positive and – negative locations were completed, the wound was closed and the animal was monitored for local tumour recurrence and overall survival. As cancer metrics, we used: (1) the number of injected cells in the $2^{nd}$ and $3^{rd}$ models, while in the $4^{th}$ model, we used (2) the volume of the recurrent tumour, and (3) the animal overall survival time after surgery. Six animals were used for groups 1 and 2 and five animals for group 3. Animals were euthanized when the size of the recurrent tumour reached 10 mm, which was set as the moribund threshold. Animal group sizes were set to support statistically valid data and to minimize animal use. Animals were randomly assigned to groups for the experiments. These studies were not blinded since the same investigators performed the grouping, dosing and analyses, rendering it unfeasible. Animals were used according to Animal Care Use Guidelines under the protocols approved by the Institutional Animal Care and Use Committees of Rice University and Houston Methodist Research Institute.

Gold targeting and clustering. To form *in vivo* intracellular clusters of gold colloids as PNB sources, we used several universal and previously verified mechanisms: leaky tumour micro-vasculature and the small size of the gold colloid conjugates (60 nm spheres) enable them to reach the tumour with the help of an effect called "enhanced permeability and retention"[48] (Fig. 1a), which prompts the receptor-antibody based accumulation of gold conjugates at the surface of cancer cells (Fig. 1b), and finally the receptor-mediated endocytosis of gold conjugates (Fig. 1c). This is endocytosis, the universal cell defence mechanism, which internalizes gold nanoparticles and concentrates them into clusters in endo-lysosomal compartments (Fig. 1c), as we found earlier *in vitro* and *in vivo*.[27,36,41] This mechanism, which efficiently differentiates cancer and normal cells by forming the largest gold clusters only in cancer cells (Fig. 1c), was also verified *in vivo* for HNSCC[27,36]: while tumour-average cluster size was around 300 nm (equivalent of tens of aggregated 60 nm nanoparticles) the adjacent normal tissue yielded only 64 nm (equivalent of single nanoparticles). The increase in size of the gold cluster provides the selective generation of PNBs in HNSCC cells because the PNB generation threshold fluence rapidly decreases with the cluster size (see the PNB sections below for details). The clustering mechanism is sensitive to the nanoparticle diameter: larger particles (>100 nm) cannot be easily internalized by cancer cells and therefore cannot create intracellular clusters. Smaller particles (<10 nm) are rapidly cleared by the organism and therefore cannot efficiently accumulate in the tumour.

The low doses of gold colloids we employed are associated with negligible systemic toxicity. We used 60 nm spheres (NanoComposix, Inc, San Diego, CA) covalently conjugated (VanPelt Biosciences LLC (Ijamsville, MD)) to the clinically-approved anti-Epidermal Growth Factor Receptor antibody, Panitumumab (Vectibix, Amgen Inc., Thousand Oaks, CA). This antibody is used in clinic against HNSCC. To form gold clusters *in vitro*, gold conjugates were incubated with cells for 24 h under physiological conditions at the concentration of gold conjugate suspension corresponding to the optical density of 0.08

(measured at the maximum of the optical spectrum, Supplementary Fig. 6a). This corresponds to a dose of approximately 0.7μg/ml. To form gold clusters *in vivo*, gold conjugates were systemically administered intravenously at the low dose of 4 mg/kg body weight 24 hours prior to the optical excitation, in order to allow their efficient clustering in the tumour.[36] This dose is only 1-10% of those reported for the diagnostic and therapeutic doses of gold nanoparticles *in vivo*.[12-14,36] These doses, timing and administration protocol were achieved as a result of several optimization experiments focused on the efficient clustering of gold nanoparticles in tumours:

A. The gold clustering efficacy was quantified through four independent metrics and methods: (1) by measuring the level of gold in tumours and other organs (which were harvested at a specific time, 6 -72 h, after the systemic administration of gold conjugates) with inductive-coupled plasma mass-spectroscopy (ICP-MS); (2) by directly measuring the size of gold clusters in harvested tissues with transmission electron microscopy; (3) by measuring PNB lifetime (the metric of the maximal diameter of PNB which correlates with the cluster size[29,35]) in slices of the harvested tissue, and (4) by measuring the acoustic amplitude of PNB time-responses *in vivo* (Fig. 4e in ref 36). We found that the systemic administration of gold nanoparticle conjugates is preferable to their local injection (Fig. 4f in ref. 36) and results in tumour-specific clustering *in vivo* (Fig. 3a,b, in ref 36). In addition, we found that 60 nm gold spheres provide the best generation of PNBs in HNSCCC *in vivo* compared to smaller nanoparticles. It is difficult for cells to internalise nanoparticles > 100 nm. With the above methods, we determined that efficient clustering *in vivo* requires at least 24 hours of lead time after the systemic injection of gold conjugates.[27,36]

B. To optimize systemic targeting, we amended the previous measurements with the ICP-MS (Perkin Elmer Nexion 300 ICP-MS, Perkin Elmer, Inc., Waltham, MA) evaluation of the gold accumulation in tumours and other organs as a function of:

- The organ: tumour, lung, liver, kidney and blood (Fig. 4a);

- The targeting antibody (Supplementary Fig. 3a): active targeting, compared to passive targeting (gold without antibody) is important for efficient systemic targeting.

- The size of the primary tumour (Supplementary Fig. 3b) is also critical: the tumour stage determines the level of tumour vasculature in a xenograft model, and it is the vasculature which delivers gold to a tumour. In the case of MRD detection, tumours are usually mature enough, and this ensures the efficient systemic delivery and accumulation of gold under active targeting with an HNSCC-specific antibody.

- The interaction of the targeting antibody with the immune system. To ensure the clinical translation of gold conjugates, we additionally studied the anti-Epidermal Growth Factor Receptor antibody "liver sink" effect[40] (which is associated with clinical challenges in using such antibodies) and the safety of gold *in vivo*. A normal mouse with an active immune system was identically treated with gold conjugated to anti-mouse EGFR antibody. The gold biodistribution (Fig. 4a) was similar to that obtained in the xenograft model and human antibody (Panitumumab). Thus, gold conjugates (unlike the antibody alone) did not reveal a significant liver sink effect and therefore can be administered in clinic at a relatively low dose.

As a result of this optimization, we determined the following optimal combination: primary tumours should be above 5 mm, Panitumumab antibody should be used to target gold, 24 hours are required to achieve clustering, and 60 nm gold spheres at a dose of 4 mg/kg.

Safety of gold nanoparticles *in vivo*. The toxicity of gold conjugates *in vivo* has been measured short term (24 and 72 h after administration) and long term (over 1 month). Three animals were studied for each time-point. To determine short-term toxicity, the harvested liver, kidney, spleen and lung were analysed for necrosis, apoptosis and other standard signs of toxicity via standard pathology. The harvested organs (kidney, lung, liver, heart) were placed in 10% neutral buffered formalin and fixed for up to 48 hours. Organs were then processed routinely and coil sections were stained with hematoxylin and eosin (H&E). Sections were examined by a board certified veterinary pathologist. Regions of normal tumour/organ and necrotic tumour/organ were delineated. The metric of tissue damage was the % of necrosis, defined as the ratio of the area of grossly necrotic tissue to the total area of tissue in a given section. Long-term toxicity was monitored by measuring animal weight and behaviour. We did not apply more sophisticated methods because the gold nanoparticles and their low doses used were safe: no signs of toxicity were observed for the period > 2 months. We verified short- and long-term toxicity *in vivo*. The histological evaluation of organs harvested at 24 h and 72 h from intact and gold-treated mice (Fig. 4b-g) revealed no toxic effects of the gold (Supplementary Table 2). Based on the high safety of the gold, the long-term toxicity was analysed only by monitoring the body weight and animal behaviour (two standard parameters) in intact and gold-treated mice and also revealed no adverse effects (Fig. 4h). Therefore, the gold conjugates, doses, and the systemic targeting method employed were safe *in vivo* and provided efficient delivery of the gold conjugates to and their clustering in a tumour to support tumour-specific PNB generation *in vivo*.

PNB generation. PNBs were generated around clusters of gold spheres with single near-infrared laser pulses (782 nm, 30 ps, Ekspla PL2251/OPG03, Ekspla UAB, Lithuania). While the stationary optical excitation of gold spheres in near-infrared is not efficient due to their low optical absorbance in this spectral interval (Supplementary Fig. 6a), our non-stationary optical excitation method[30] provides efficient PNB generation around these nanoparticles with a 30 ps laser pulse at NIR wavelength of 782 nm, the wavelength associated with minimal bio-damage and maximal tissue penetration depth.[49] Due to the transient photothermal modification of the nanoparticle surface by a short NIR laser pulse, the PNB generation efficacy at 782 nm reaches the level achieved by excitation at the visible wavelength (Supplementary Fig. 6b). Unlike any nanoparticle, a PNB is a non-stationary transient event, an expanding and collapsing vapour nanobubble of nanosecond duration, usually without recoil.[29] Such a nanobubble results from the rapid evaporation of the liquid around an overheated gold cluster due to the absorption and plasmonic conversion of the laser pulse energy. The use of a nanoparticle cluster instead of single nanoparticles or their ensembles provides a significant reduction in the threshold laser fluence of the PNB generation and an increase in the PNB generation efficacy[29] because the threshold fluence decreases with the cluster size. This unique property of PNB, in turn, provides the high cancer cell specificity of PNB *in vivo* compared to any targeted nanoparticles, since the largest clusters are self-built by aggressive cancer cells and do not emerge in normal cells[27,36] (Fig. 1d). We apply the fluence of the laser pulse below the PNB generation threshold for single nanoparticles but above the PNB generation threshold for their large clusters. Thus, PNBs are selectively generated only around large clusters, i.e. in cancer cells, and do not emerge in normal cells even despite unavoidable non-specific accumulation of single nanoparticles in normal cells.[27,36] In addition to the high cancer cell specificity, a PNB efficiently thermally insulates the overheated gold cluster from the outer media, thus preventing any thermal bio-damage to any object outside the PNB.[29]

The laser fluence was measured through the acquisition of the beam image in the target plane (to obtain the beam diameter, we used the imagers Andor Luca EMCDD (Andor technology Ltd, Belfast, UK) and Spiricon (Ophir-Spiricon LLC, N. Logan, UT) and pulse energy meter (Ophir-Spiricon LLC, N. Logan, UT). Single cell experiments used our photothermal microscope described previously.[29] In the *in vivo* experiments, the laser pulse was delivered to the tissue via a custom endoscope (Supplementary Fig. 2). The cells were injected into the surgical bed of a mouse in specific amounts from 3 to 100 with a 0.5 µl Hamilton nano-syringe (Sigma-Aldrich Co. LLC, St. Louis, MO) with micrometre drive (Supplementary Fig. 2).

Detection of PNBs. To detect PNBs optically with a single PNB sensitivity and resolution, we used our established optical scattering method.[29] A continuous probe laser beam (633 nm, 05-STP-901, Melles Griot, Rochester, NY) was focused on the PNB source and its axial intensity was monitored after the object with a high-speed photodetector (FPD 510-FV, Menlo Systems GmbH, Martinsried, Germany) connected to a digital oscilloscope (LeCroy 42Xs, Teledyne LeCroy, Chestnut Ridge, NY). The vapour-liquid boundary of a PNB scatters the incident probe laser beam thus reducing its axial intensity. The expansion and collapse of a PNB creates a specific dip-shaped pattern in the time-response of the intensity of the probe laser to a single pump laser pulse. Its duration, or lifetime, characterizes the maximal diameter of a PNB.[29] This method directly detects individual PNBs, but only in optically transparent media.

To detect PNBs in opaque tissue (Fig. 1d), we made use of the pressure pulse emitted by the expanding and collapsing PNB. This pressure pulse was detected with a custom-built acoustic detector (Precision Acoustics Ltd, Dorset, UK) comprised of a broadband ultrasound sensor of a needle type integrated with a pre-amplifier. The sensor used an external power supply with a second pre-amplifier. The output of the second pre-amplifier was connected to a digital oscilloscope to register an acoustic time-response to a single laser pulse. In tissue, we used a diagnostic algorithm based on the co-registration of the two time-responses from a cancer-free location (the reference) and from the location where cancer cells might be present (the test). The differential response was determined by subtracting the reference response from the test response. For signal metrics, we used the peak-to-peak amplitude of the differential response. As a cancer diagnostic metric, we additionally used the Diagnostic Index (DI), defined as the relative increase in test response amplitude ($V_{test}$) over the reference or background response amplitude ($V_{ref}$):

$$DI = \frac{V_{test} - V_{ref}}{V_{ref}}$$

Additional details regarding the cancer cell specificity of PNBs and the algorithms of their detection in tissue depth and their intraoperative application can be found in the Supplementary Methods.

References

1. Meier, JD, Oliver, DA & Varvares, MA. Surgical margin determination in head and neck oncology: current clinical practice. The results of an International American Head and Neck Society Member Survey. *Head Neck* 27, 952-958 (2005).

2. de Carvalho, AC, et al. Clinical significance of molecular alterations in histologically negative surgical margins of head and neck cancer patients. *Oral. Oncol.* 48, 240-248 (2012).

3. Loree, TR & Strong, EW. Significance of positive margins in oral cavity squamous carcinoma. *Am. J. Surg.* 160, 410-414 (1990).

4. Looser, KG, Shah, JP & Strong, EW. The significance of "positive" margins in surgically resected epidermoid carcinomas. *Head Neck Surg.* 1, 107-111 (1978).

5. Vikram, B, Strong, EW, Shah, JP & Spiro, R. Failure at the primary site following multimodality treatment in advanced head and neck cancer. *Head Neck Surg.* 6, 720-723 (1984).

6. Leemans, CR, Braakhuis, BJ & Brakenhoff, RH. The molecular biology of head and neck cancer. *Nat. Rev. Cancer* 11, 9-22 (2011).

7. Haddad, RI & Shin, DM. Recent advances in head and neck cancer. *N. Engl. J. Med.* 359, 1143-1154 (2008).

8. Calabrese, L, et al. Association of Radiotherapy and Oncology of the Mediterranean Area (AROME). Future challenges in head and neck cancer: from the bench to the bedside? *Crit. Rev. Oncol. Hematol.* 84, e90-96 (2012).

9. Langendijk, JA, et al. Impact of late treatment- related toxicity on quality of life among patients with head and neck cancer treated with radiotherapy. *J. Clin. Oncol.* 26, 3770-3887 (2008).

10. Radosevich, JA. *Head and Neck cancer: current perspectives, advances and challenges*. Springer 1070 pp (2013).

11. Vermorken, JB, *et al.* EORTC 24971/TAX 323 Study Group. Cisplatin, fluorouracil, and docetaxel in unresectable head and neck cancer. *N. Engl. J. Med.* 357, 1695-1704 (2007).

12. Wang, LV. Multiscale photoacoustic microscopy and computed tomography. *Nat. Photonics* 3, 503-509 (2009).

13. Jathoul, AP, *et al.* Deep in vivo photoacoustic imaging of mammalian tissues using a tyrosinase-based genetic reporter. *Nat. Photonics* 9, 239-246 (2015).

14. Kaiplavil, S & Mandelis, A. Truncated-correlation photothermal coherence tomography for deep subsurface analysis. *Nat. Photonics* 8, 635-642 (2014).

15. Lo Celso, C, *et al.* Live-animal tracking of individual haemotapoietic stem/progenitor cells in their niche. *Nature* 457, 92-96 (2009).

16. Upile, T, *et al.* Head and neck optical diagnostics: vision of the future of surgery. *Head Neck Oncol.* 1, 25 (2009).

17. Thorek, DL, Ogirala, A, Beattie, BJ & Grimm, J. Quantitative imaging of disease signatures through radioactive decay signal conversion. *Nat. Med.* 19, 1345–1350 (2013).

18. Nguyen, QT & Tsien, RY. Fluorescence-guided surgery with live molecular navigation – a new cutting edge. *Nat. Reviews* 13, 653-662 (2013).

19. van Dam, GM, *et al.* Intraoperative tumor-specific fluorescence imaging in ovarian cancer by folate reseptor-α targeting: first in-human results. *Nat. Med.* 17, 1315-1319 (2011).

20. Vahmeijer, AL, Hutteman, M, van de Vorst, JR, van de Velde, CJH, Frangioni, JV. Image-guided cancer surgery using near-infrared fluorescence. *Nat. Rev. Clinical. Oncology* 10, 507-518 (2013).

21. Holt, D, *et al.* Intraoperative near-infrared imaging can distinguish cancer from normal tissue but not inflammation. *PLoS One* 9, e103342 (2014).

22. Troyan, SL, *et al.* The FLARE intraoperative near-infrared fluorescence imaging system: a first-in-human clinical trial in breast cancer sentinel lymph node mapping. *Ann. Surg. Oncol.* 16, 2943-2952 (2009).

23. Qiu, L, *et al.* Multispectral scanning during endoscopy guides biopsy of dysplasia in Barrett's esophagus. *Nat. Med.* 16, 603-606 (2010).

24. Ntziachristos, V. Clinical translation of optical and optoacoustic images. *Phil. Trans. R. Soc. A* 369, 466-4678 (2011).

25. de Boer, E, *et al.* Optical innovations in surgery. *BJS* 105, e56-e72 (2015).

26. Taruttis, A & Ntziachristos, V. Advances in real-time multispectral optoacoustic imaging and its applications. *Nat. Photonics* 9, 219-227 (2015).

27. Lukianova-Hleb, EY, *et al.* On-demand intracellular amplification of chemoradiation with cancer-specific plasmonic nanobubbles. *Nat. Med.* 20, 778-784 (2014).

28. Hleb, EY, *et al.* LANTCET: elimination of solid tumor cells with photothermal bubbles generated around clusters of gold nanoparticles. *Nanomedicine* 3, 647-667 (2008).

29. Lukianova-Hleb, E, *et al.* Plasmonic nanobubbles as transient vapor nanobubbles generated around plasmonic nanoparticles. *ACS Nano* 4, 2109–2123 (2010).

30. Lukianova-Hleb, EY, Volkov, AN, Wu, X & Lapotko, DO. Transient enhancement and spectral narrowing of the photothermal effect of plasmonic nanoparticles under pulsed excitation. *Adv. Mater.* 25, 772-776 (2013).

31. Kitz, M, et al. Vapor bubble generation around gold nano-particles and its application to damaging of cells. *Biomed. Opt. Express* 2, 291-304 (211).

32. Pitsillides, CM, Joe, EK, Wei, X, Anderson, RR & Lin, CP. Selective cell targeting with light-absorbing microparticles and nanoparticles. *Biophys. J.* 84, 4023-4032 (2003).

33. Lapotko, D, et al. Photothermal microscopy and laser ablation of leukemia cells targeted with gold nanoparticles. *Proc SPIE* 5697, 82-89 (2005).

34. Lukianova-Hleb, EY, Hanna, EY, Hafner JH & Lapotko, DO. Tunable plasmonic nanobubbles for cell theranostics. *Nanotechnology* 21, 085102 (2010).

35. Lukianova-Hleb, EY, et al. Improved cellular specificity of plasmonic nanobubbles versus nanoparticles in heterogeneous cell systems. *PLoS ONE* 7, e34537 (2012).

36. Lukianova-Hleb, EY, et al. Plasmonic nanobubbles rapidly detect and destroy drug-resistant tumors. *Theranostics* 2, 976-987 (2012).

37. Nanospectra Biosciences, Inc. ClinicalTrials.gov [website on the Internet] Pilot study of aurolase(tm) therapy in refractory and/or recurrent tumors of the head and neck. [updated September 23, 2014]. Available from: https://clinicaltrials.gov/ct2/show/NCT00848042?term=aurolase%28tm%29&rank=1. NLM identifier: NCT00848042.

38. Merchant, B. Gold, the noble metal and the paradoxes of its toxicology. *Biologicals* 26, 49-59 (1998).

39. Kean, WF & Kean, IRL. Clinical pharmacology of gold. *Inframmopharmacology* 16, 112-125 (2008).

40. Goldstein, NI, Prewett, M, Zuklys, K, Rockwell, P & Mendelsohn, J. Biological efficacy of a chimeric antibody to the epidermal growth factor receptor in a human tumor xenograft model. *Clin. Cancer Res.* 1, 1311-1318 (1995).

41. Wagner, DS, *et al.* The in vivo performance of plasmonic nanobubbles as cell theranostic agents in zebrafish hosting prostate cancer xenografts. *Biomaterials* 31, 7567-7574 (2010).

42. Chen, H & Diebold, G. Chemical generation of acoustic waves: a giant photoacoustic effect. *Science* 250, 963-966 (1995).

43. Lin, CP & Kelly, MW. Cavitation and acoustic emission around laser-heated microparticles. *Appl. Phys. Lett.* 72, 2800 (1998).

44. Lukianova-Hleb, EY, Volkov, AN & Lapotko, DO. Laser pulse duration is critical for the generation of plasmonic nanobubbles. *Langmuir* 30, 7425-7434 (2014).

45. Reuveni, T, Motiei, M, Romman, Z & Popovtzer, R. Targeted gold nanoparticles enable molecular CT imaging of cancer: an in vivo study. *Int. J. Nanomedicine* 6, 2859-2864 (2011).

46. Sano, D, *et al.* Disruptive TP53 mutation is associated with aggressive disease characteristics in an orthotopic murine model of oral tongue cancer. *Clin. Cancer Res.* 17, 6658–6670 (2011).

47. Sharafinski, ME, Ferris, RL, Ferrone, S & Grandis, JR. Epidermal growth factor receptor targeted therapy of squamous cell carcinoma of the head and neck. *Head Neck* 32, 1412–1421 (2010).

48. Maeda, H. The enhanced permeability and retention (EPR) effect in tumor vasculature: the key role of tumor-selective macromolecular drug targeting. *Adv. Enzyme Regul.* 41, 189-207 (2001).

49. Weissleder, R. A clearer vision for in vivo imaging. *Nat. Biotechnology* 19, 316-317 (2001).

Acknowledgements

Authors thank Ehab Y. Hanna and Ron J. Karni, for the discussion of clinical applications of the technology, Andrew Hurrell, Thomas Kelley, Eliberto Batres, Dan Wagner, Aidas Aleknavicius and Rokas Sulcas for the help with experimental equipment, Judit Markovits for assistance with veterinary pathology and surgical training. E.Y.L.H., Y.S.K., B.E.O. and D.O.L. were supported by the grants from Gillson Longenbaugh Foundation (Houston, TX), NSF (CBET-1341212), NIH (R01GM094816).

Author contributions

E.Y.L.H. conducted PNB experiments, prepared the figures and wrote the manuscript; Y.S.K. conducted the animal experiments and collected animal data; I.B., A.M.G., D.O.L., B.E.O. and E.Y.L.H. discussed the experimental design and results, and clinical applications of the technology; B.E.O. contributed to the conceptual experimental design and organized the animal handling and monitoring; D.O.L. developed the technology and research strategy, designed the experimental setup, and wrote the manuscript.

Competing financial interests

The authors declare no competing financial interests.

Figure legends

Figure 1:
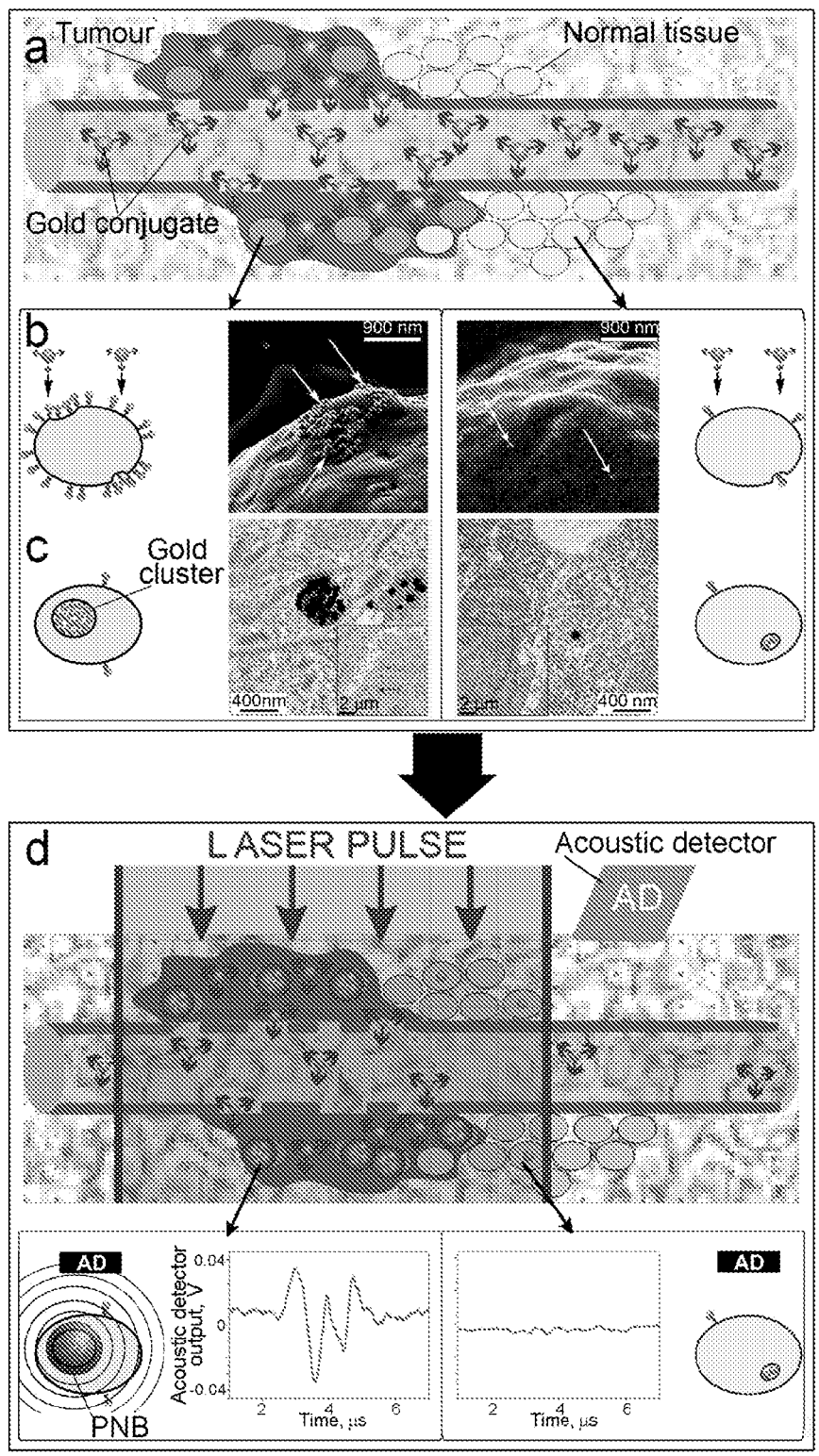
FIGS. 1A-1C illustrate known principles of plasmonic nanobubble ("PNB") formation in isolated cells.
Figure 2:
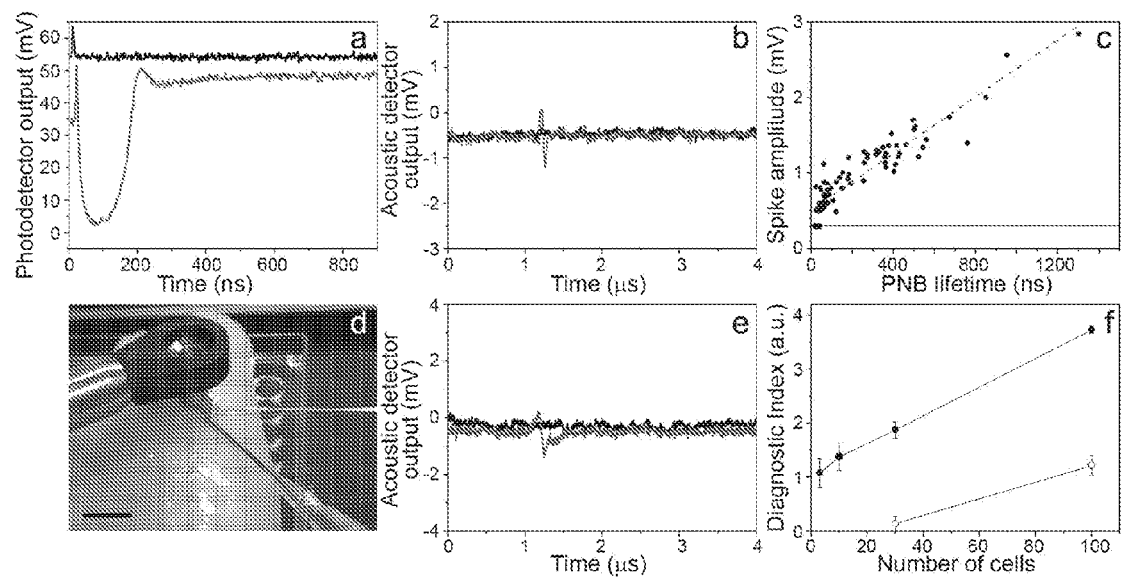

Figure 1. The mechanism of PNB diagnostics of residual microtumours and cancer cells *in vivo*. (a) Systemic delivery of gold conjugates to the tumour via their leaky vasculature. (b) Accumulation of gold conjugates by receptors of cancer cells (gold shown with white arrows in illustrative scanning electron microscopy images[41]). (c) Intracellular clustering of gold conjugates via receptor-mediated endocytosis (illustrative transmission electron microscopy images[27]); a gold cluster, upon exposure to a single laser pulse of low fluence, selectively generates a PNB only in cancer cells; normal cells with non-specifically internalized single gold nanoparticles do not generate PNBs because of the higher threshold of PNB generation. (d) Acoustic signal of PNB (illustrative red time-response) reports even a single cancer cell in solid tissue, but not normal cells (illustrative green time-response).

Figure 2. PNBs report even single cancer cells *in vitro* in transparent media (a-c) and in tissue (d-e). Simultaneously detected optical scattering and acoustic time-responses to single laser pulses (782 nm, 30 ps) applied to individual HNSCC cancer cells in transparent media: (a) The PNB-positive optical time-response in gold conjugate-pretreated cell (red) and PNB-negative time-response in intact (not pretreated with gold) cell (black). (b) Acoustic time-response in gold-pretreated (red) and intact (black) cells. (c) The amplitude of bipolar PNB-specific spike in acoustic time-response as a function of the PNB lifetime obtained in the same cells under the variable fluence of a laser pulse (10-66 $mJ/cm^2$): the black horizontal line shows the level of the noise and background, dashed red line shows the linear fit above the detection threshold. (d) Experimental setup with an endoscope (grey), injection needle (silver) and the acoustic sensor (gold) applied to chicken breast (scale bar: 10 mm). (e)

Acoustic time-responses before (black) and after injection (red) of 3 gold conjugate-pretreated cells at 1 mm tissue depth. (f) Diagnostic Index (the relative increase in the amplitude of the test time-response versus that of the reference, cancer-free time-response) as a function of the amount of gold conjugate-pretreated cells injected at the tissue depth of 1 mm (solid) and 3-4 mm (hollow). Data are mean ± standard error. Error bars are based on 6 measurements under identical conditions.

Figure 3:
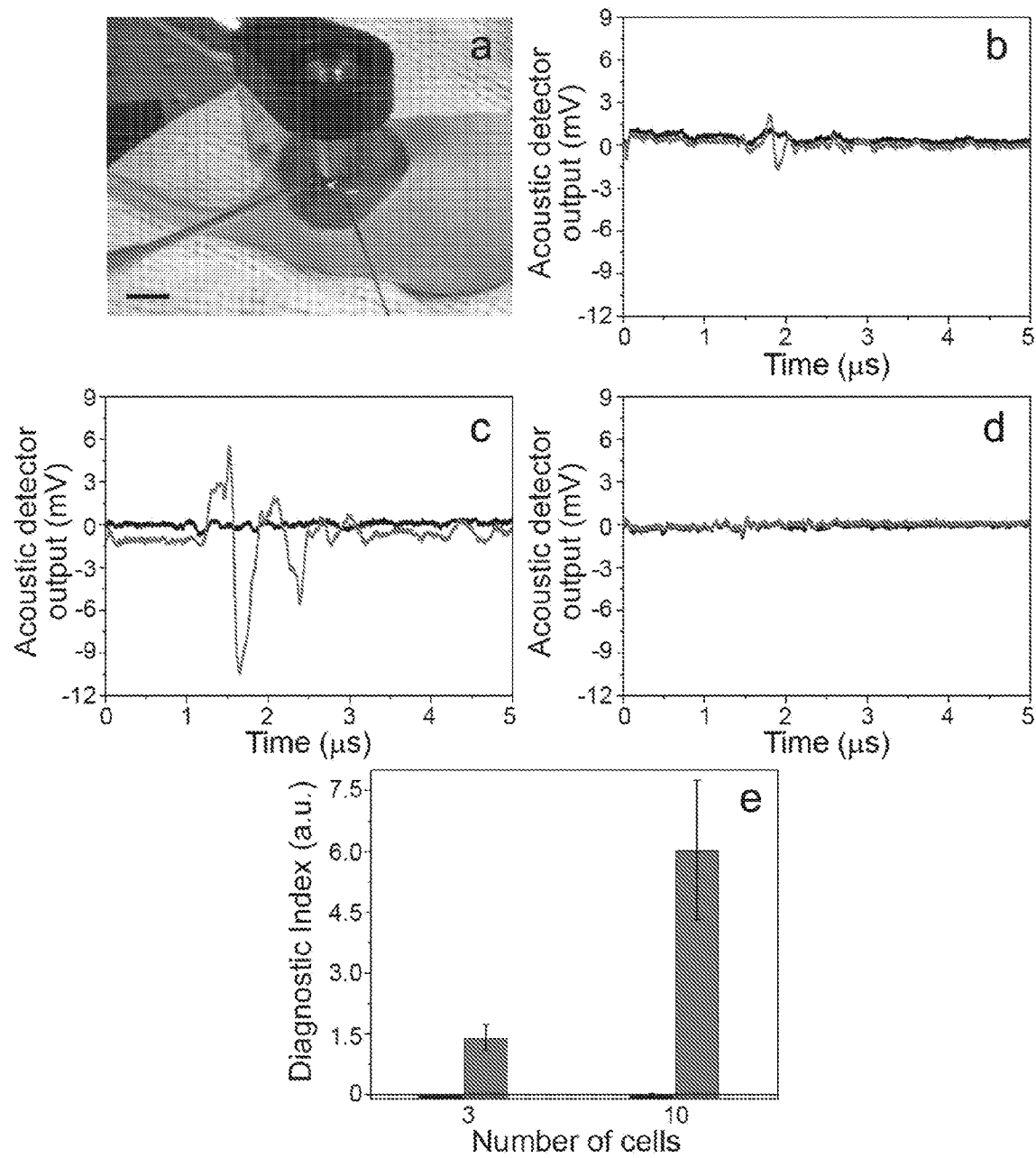

Figure 3. Intraoperative non-invasive detection of cancer cells in a surgical bed *in vivo* with a single laser pulse (782 nm, 30 ps, 70 mJ/cm$^2$). (a) Experimental setup with an endoscope, cell injection needle and the acoustic sensor applied to a surgical bed (scale bar: 5 mm). (b) Acoustic time-responses before (black) and after (red) injection of 3 gold conjugate-pretreated cancer cells at 1 mm tissue depth. (c) Acoustic time-responses before (black) and after (red) injection of 10 gold conjugate-pretreated cancer cells at 1 mm tissue depth. (d) Acoustic time-responses before (black) and after (red) injection of 10 intact (untreated with gold conjugates) cancer cells at 1 mm tissue depth. (e) Diagnostic Index (the relative increase in the amplitude of the test time-response versus that of the reference, cancer-free time-response) as the function of the amount of injected cells for gold conjugate-pretreated (solid red) and intact (solid black) cancer cells at 1 mm depth. Data are mean ± standard error. Error bars are based on 6 measurements under identical conditions.

Figure 4:
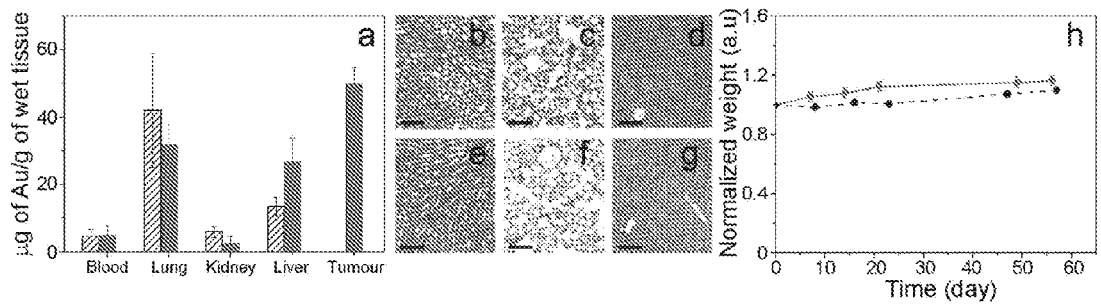
FIG. 4A illustrates an exemplary embodiment of PNB generation and detection at increasing tissue depth.
FIG. 4B illustrates exemplary laser fluence attenuation curves along tissue depth at the different entry levels of laser pulse fluence.
FIG. 4C illustrates an exemplary time-delay between two time-responses obtained for cancer cells at different depths.
Figure 5:
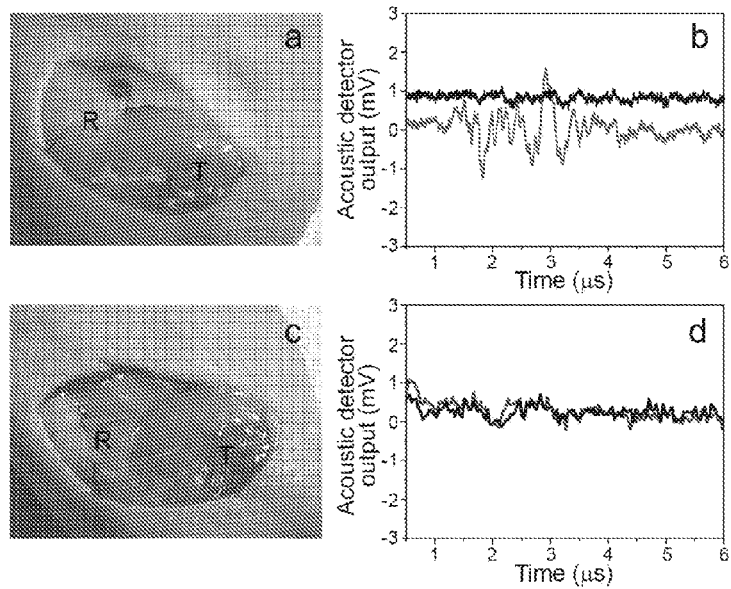
Figure 6:
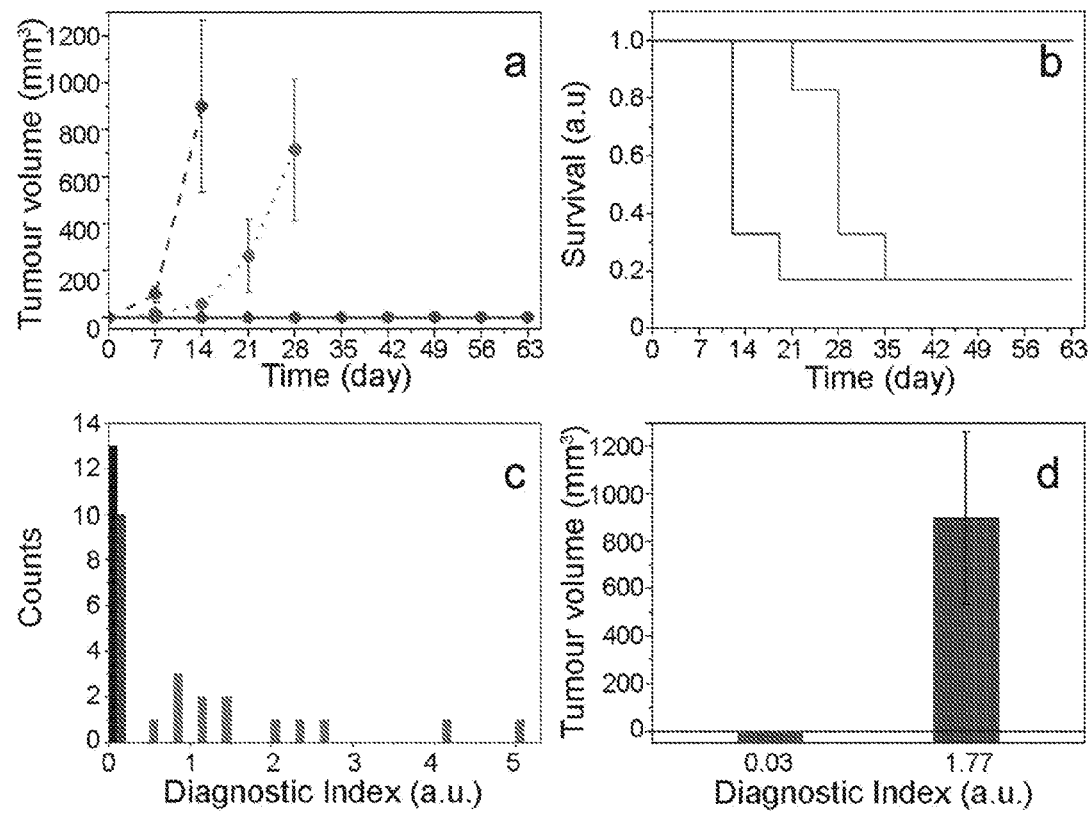

Figure 4. The biodistribution and toxicity *in vivo* after systemic administration of gold conjugates reveals a safe and efficient accumulation of gold nanoparticles in a tumour. (a) Biodistribution for anti-human (solid red, Panitumumab antibody) and anti-mouse (shaded grey, ab231 antibody) gold conjugates with antibody against epidermal growth factor receptor in nude (gold-Panitumumab conjugates) and normal mice (gold-ab234 conjugates) (n=3). (b-g) Histological analysis of organs obtained from intact (b-d) and gold conjugate-injected (e-g) animals 72 h after the administration of gold conjugates: liver (b, e), lung (c, f), kidney (d, g) (scale bar: 100 µm). (h) Body weight as the function of time for intact mice (black) and mice after systemic injection of gold conjugates with Panitumumab antibody (red). Data are mean ± standard error. Error bars are based on six mice per group.

Figure 5. PNBs intraoperatively detect MRD in a surgical bed and guide its resection in real time with a standard surgery: (a) An image of the surgical bed after primary surgery: MRD-positive location "T" in the nest of the primary tumour and MRD-negative location "R" with normal tissue. (b) Acoustic time-responses to single laser pulses (782 nm, 30 ps, 70 mJ/cm$^2$) obtained immediately after the primary surgery at the "T" location of possible MRD (red) and at the MRD-negative location "R" (black). (c) An image of the surgical bed after PNB-guided surgery. (d) Acoustic time-responses obtained after PNB-guided surgery in the location of the secondary resections (green) and in the initially MRD-negative location (black).

Figure 6. PNBs improve surgical outcome in both resectable and unresectable MRDs. The animal group-averaged metrics of local recurrent tumours after standard surgery with resectable MRD (blue, n=6), PNB-guided surgery of resectable MRD (green, n=5) and PNB nano-surgery of unresectable MRD (red, n=6) show a significant improvement in the outcome in both resectable and unresectable cases when the surgery is enhanced with PNBs. (a) Tumour volume. (b) Animal survival. (c) Histograms of the Diagnostic Index obtained in MRD-positive (red) and –negative (black) locations after standard surgery and for the MRD-positive locations after PNB-guided surgery (green). (d) Recurrent tumour volumes plotted for the group-averaged Diagnostic Indexes after standard (blue) and PNB-guided (green) surgery show the prognostic potential of PNBs to intraoperatively predict tumour recurrence. Data are mean ± standard error. Error bars are based on six (blue and red) or five (green) mice per group.

APPENDIX B

SUPPLEMENTARY INFORMATION for

Intraoperative diagnostics and elimination of residual micro-tumours with plasmonic nanobubbles Ekaterina Y. Lukianova-Hleb, Yoo-Shin Kim, Ihor Belatsarkouski, Ann M. Gillenwater, Brian E. O'Neill, Dmitri O. Lapotko A: Supplementary Tables Supplementary Table 1. Comparison of MSOT (multi-spectral optoacoustic tomography) and PNB (plasmonic nanobubble) technologies for *in vivo* intra-operative management of MRD (residual micro-tumours) in solid tissues in a surgical bed*

| Parameter/property | MSOT (references in the end of the document) | PNB (current manuscript) |
|---|---|---|
| Intraoperative MRD detection *in vivo* (in surgical bed) in solid tissue | Not reported | Yes, compatible with standard surgery |
| Influence on the surgical outcome (local recurrence and overall survival) | Not reported | Yes, multi-fold improvement in survival in resectable and unresectable cases |
| Tumour detection sensitivity in solid tissue *in vivo* | > 1 mm,[6-13] >2500 cells (mouse macrophages)[14] | Single cells and microtumours of size << 1mm (undetectable with standard pathology) |
| Time to result *in vivo* for solid tissue | 150 μs – 20 min,[1,6-14] not reported for MRD | < 10 μs per location (detection), less than 1 min per 2x2 cm surgical bed (including the surgery |

|  |  | involved) |
|---|---|---|
| Requirements for diagnostic agents | Several different dyes or nanoparticles[6-17,20] | Single type clinically-validated agent - colloidal gold |
| Requirements for laser radiation | Several laser beams with different wavelengths, multiple pulses[1-32] | Single laser beam, single pulse, single wavelength |
| Complexity of signal interpretation | High: Reconstruction and processing of primary signals required[5,25-28] | Low: Direct measurement of the amplitude of primary signal |
| *References are based on the Supplementary references |||

Supplementary Table 2. Short-term toxicity of treatment (defined as % of grossly necrotic area / total examined area)

| Treatment | Time | Kidney | Liver | Lung |
|---|---|---|---|---|
| Untreated | 24h | 0% | 0% | 0% |
|  | 72h | 0% | 0% | 0% |
| PNB | 24h | 0% | 0% | 0% |
|  | 72h | 0% | 0% | 0% |

B: Supplementary Figures

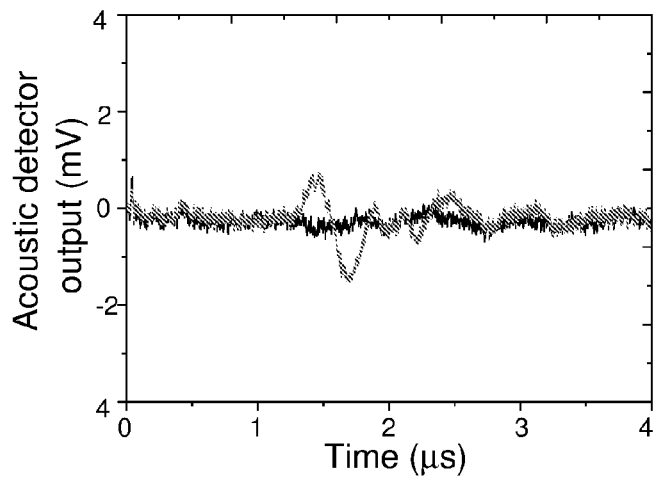

Supplementary Fig. 1. Acoustic time-responses to the sequential laser pulses (782 nm, 70 mJ/cm$^2$) as obtained in the same location of a chicken breast after injecting gold pre-treated cancer cells: the first laser pulse results in a PNB-positive time-response (red), at the same time this PNB mechanically scatters the intracellular gold cluster by scattering gold nanoparticles; the second pulse results in a PNB-negative time-response (black) because the PNB generation threshold of scattered individual gold nanoparticles is much higher than the PNB generation threshold fluence for a gold cluster.

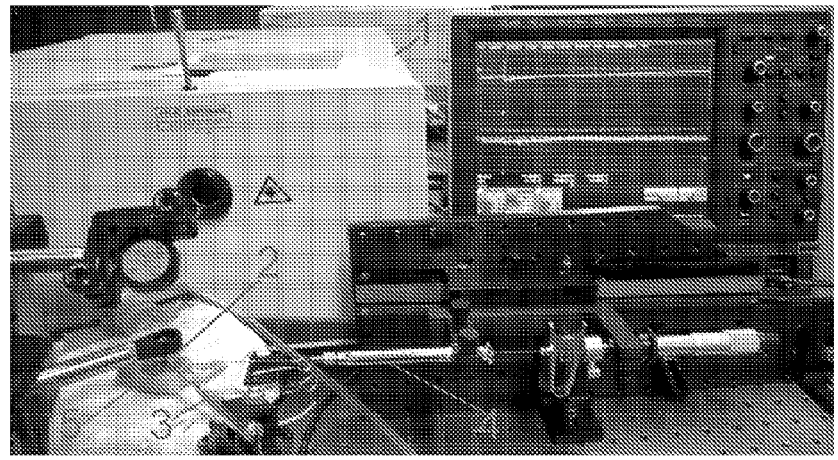

Supplementary Fig. 2. Experimental setup for *in vivo* generation and detection of PNBs: (1) Pulsed NIR laser (782 nm, 30 ps). (2) Endoscope for the delivery of the laser beam (diameter 4 mm) into a surgical bed. (3) Acoustic sensor with pre-amplifier in the back. (4) Nanosyringe for injection of cancer cells into the surgical bed of (5) anesthetized mouse.

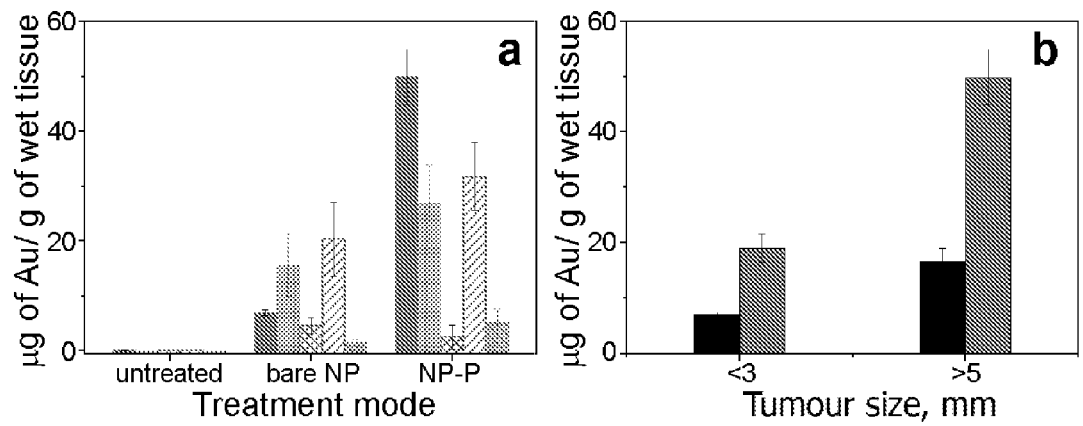

Supplementary Fig. 3. Levels of gold nanoparticles (μg/g of wet tissue) in specific organs of nude mice (n = 3) as measured with inductively-coupled plasma mass-spectroscopy after the systemic administration of gold colloids (4 mg/kg), 24 h after injection: (a) Influence of the tumour-specific antibody on the levels and biodistribution of gold (bare NP – gold colloids without antibody, NP-P – Panitumumab antibody-conjugated gold colloids, dark red – tumour, light red – liver, dense shaded – kidney, shaded – lung, light red with shading - blood). (b) Influence of the tumour size on the accumulation of gold in a tumour: black – bare gold colloids, red – Panitumumab-conjugated gold colloids. Data: mean ±SE.

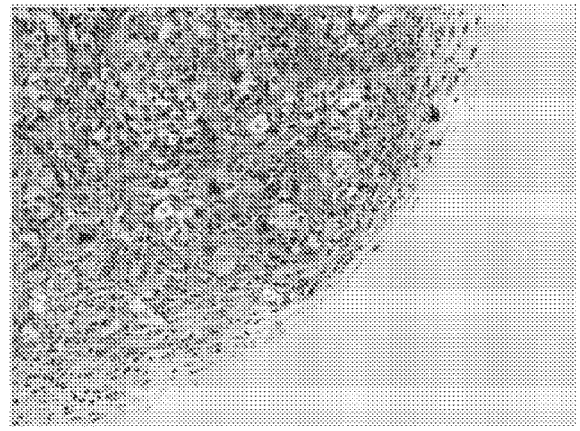

Supplementary Fig. 4. Histological image of H&E-stained sample of the resected primary tumour shows positive margin in the centre of the resection (shown with a green line).

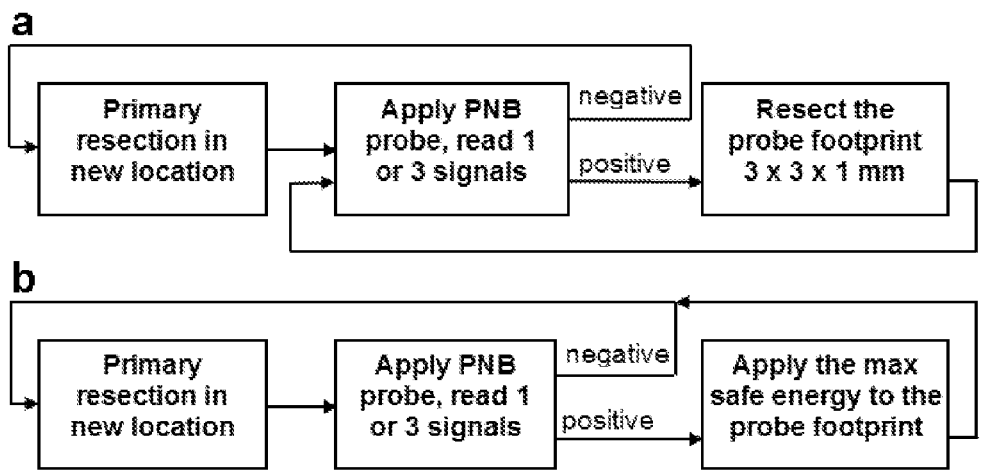

Supplementary Fig. 5. Algorithms of intraoperative management of resectable (a) and unresectable (b) MRD in surgical bed with plasmonic nanobubbles (PNB): the PNB probe is applied to specific locations in the surgical bed and the time-response to a single laser pulse is obtained within microseconds; several (1-3) laser pulses of increasing energy can be applied sequentially to scan various depths of tissue (see Fig. 8 for details); PNB-positive time-response is interpreted as MRD in a surgical bed within the footprint of the PNB probe, MRD is eliminated through the secondary resections of the probe footprint with the follow-up control of the MRD (until the time-response becomes PNB-negative) (a), or through the generation of lethal PNBs if MRD cannot be resected (b).

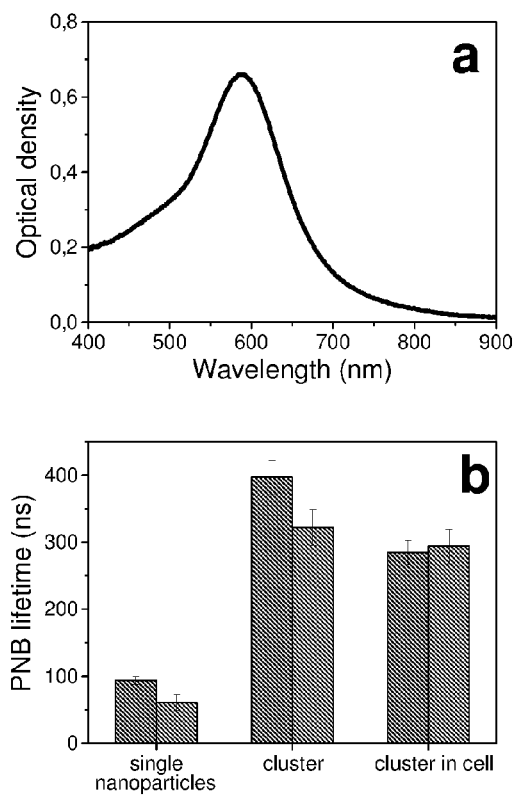

Supplementary Fig. 6. Photothermal properties of the suspension of 60 nm gold spherical nanoparticles conjugated to Panitumumab (anti-EGFR antibody). (a) The photothermal efficacy under stationary optical excitation (measured as optical extinction) spectrum shows the absorption maximum between 500 and 600 nm and negligible optical absorbance (and hence the low photothermal efficacy) at 782 nm. (b) The photothermal efficacy of the same nanoparticles (measured as thelifetime of a PNB) under non-stationary optical excitation with single 30 ps pulses at 540 nm (green) and 782 nm (red) for single and clustered nanoparticles in water and for individual HN31 cells incubated with these nanoparticles for 24 h: non-stationary optical excitation significantly increases the photothermal efficacy of the nanoparticles at 782 nm.

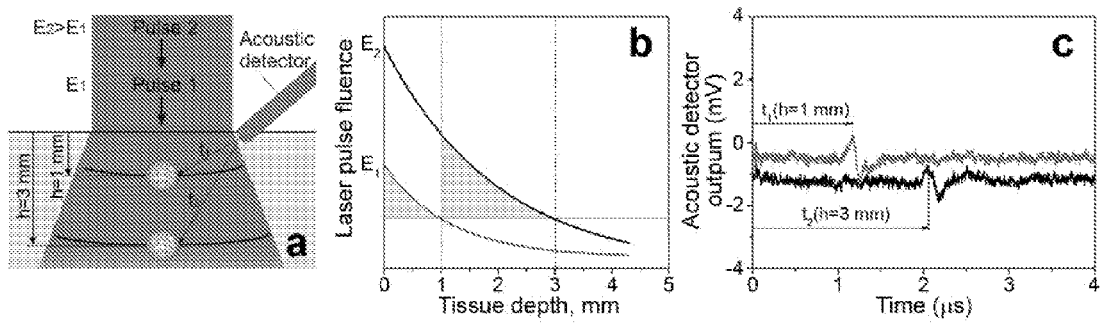

Figure 7:
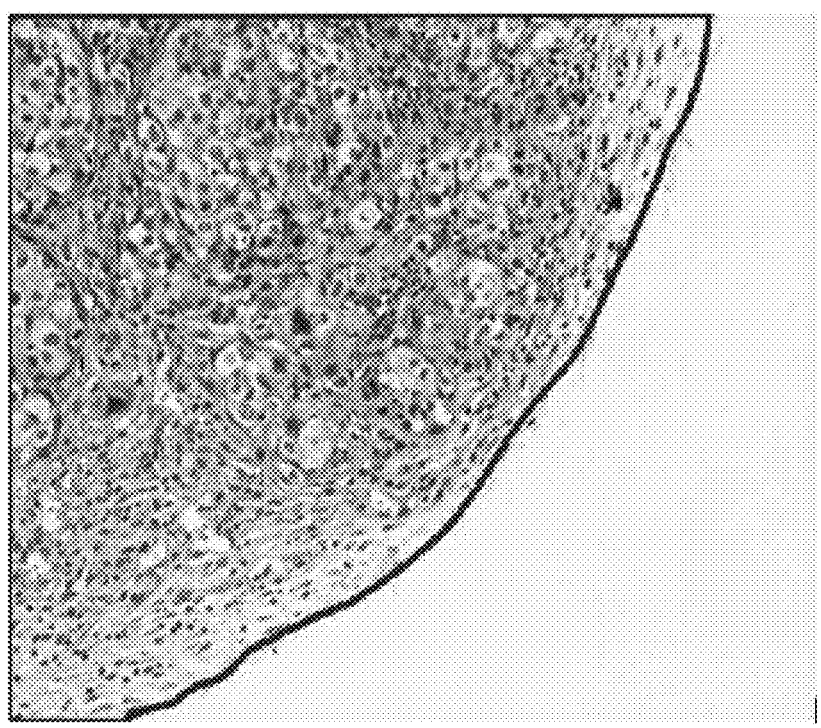
FIG. 7 illustrates an exemplary histological image of a resected primary tumor.

Supplementary Fig. 7. In-depth detection of cancer cells with PNBs with two sequential laser pulses of increasing fluence: (a) A diagram of PNB generation and detection at increasing tissue depth (h) by increasing the laser pulse fluence (E) of the second sequential laser pulse. (b) The laser fluence attenuation curves with tissue depth coupled with the PNB generation threshold fluence (black horizontal line) show the maximal tissue depth of PNB generation at the two different fluences E1 and E2 > E1: the first laser pulse generates PNBs within 1 mm depth at the fluence E1, the second pulse at the fluence E2 generates PNBs within the depth range from 1 mm to 3 mm; no PNBs can be generated with the $2^{nd}$ pulse in the cells which responded with PNBs to the 1st pulse because the PNB destroys the gold cluster by scattering gold nanoparticles (see Supplementary Fig. 1 for details). (c) time-delay between the two time-responses obtained in a chicken breast for cancer cells injected at the depth of 1mm and 3 mm under the geometry of the laser beam and acoustic detector as shown in (a).

C: Supplementary Methods

1. Intraoperative algorithms for management of resectable and unresectable MRD with PNBs. To minimize surgical morbidity and to maximize the efficacy of MRD elimination, we introduced two modes of PNB-guided surgery:

- *Mode 1: MRD is resectable* (Supplementary Fig. 5a). After the primary resection in a specific location, the PNB probe is manually applied to this location in the surgical bed, a single or multiple laser pulses are generated and the time-responses are collected. In the case of a PNB-positive time-response, standard "macro" surgery is applied to resect each PNB-positive zone (the probe footprint) of 1 mm depth x 3 x 3 mm width immediately after the PNB signal is detected. Then, the PNB probe is applied again to the same location and another time-response is collected. In the case of a PNB-positive signal, the procedure is repeated until the time-response reports no PNBs. In the case of a PNB-negative signal, the PNB probe is moved by a surgeon to the next location and the loop "detect PNB – resect – detect PNB" is repeated (Supplementary Fig. 5a). Compared to standard surgery, this protocol reduces the resected volume from a relatively large [10 mm deep x 10 x 10 mm] to, ultimately, very small one [2 mm deep x 3 x 3 mm] - that is, almost 50-fold. Thus, PNB-guided surgery minimises the morbidity compared to standard surgery. The diagnostic part of this protocol takes microseconds for each measurement and does not limit the surgical procedure.

For example, in head and neck surgery (the subject of our study), in order to avoid MRD in the tongue, a surgeon removes most of the tongue first, and then does reconstructive surgery to restore the tongue with donor tissues. With PNB-guided surgery, this morbid step can be optimized without compromising the outcome, thus improving both the patients' eligibility for surgery and their quality of life. Our approach is also in line with a current trend in surgery which is aimed at minimizing the volume of resected margins when eliminating MRD.[33]

- *Mode 2: MRD is unresectable* (Supplementary Fig. 5b). When a residual microtumour grows along an important nerve or an artery, even PNB-guided macro-surgery cannot be applied. To resolve this most challenging case, we propose PNB nano-surgery. To eliminate MRD upon detecting the PNB-positive time-response, we employ only the mechanical impact of the PNB: the same location is exposed to additional laser pulses at the maximal safe energy to ensure the maximal destruction of detected residual cancer cells by PNBs (Supplementary Fig. 5b). This nano-surgery is monitored in real time via the PNB signals. This mode was not fully optimized in our work because it requires another, more powerful laser, not currently available. Our previous data (Fig. 3b in ref 34) suggest that by increasing the fluence from 70 to 120-140 $mJ/cm^2$, the outcome of PNB nano-surgery will be further improved.

2. Probing various tissue depths with PNBs. The methods of PNB generation and detection described above are limited in solid tissues by the strong optical attenuation of the laser fluence with the tissue depth. In most of the experiments, we used single pulses at a single level of laser fluence. This is sufficient for the diagnostics of superficial MRD in surgical margins within 1-2 mm depth (which is still better than any of optical methods whose sensitivity is limited by tens of micrometres of solid tissue depth for microscopic tumours or single cancer cells). To better accommodate the laser fluence attenuation in deeper tissues, we further modified the diagnostic algorithm by applying two pulses in the same location, the next pulse having a higher fluence (Supplementary Fig. 7a). The PNB generation threshold fluence remains the same at any tissue depth, around 10-15 mJ/cm$^2$, since the threshold at a specific laser wavelength is determined only by the size of the gold cluster.[35,36] This PNB threshold, coupled with the attenuation of the laser fluence with depth, determines the maximal depth of PNB generation under a specific fluence (Supplementary Fig. 7b). The next pulse of higher fluence generates PNBs deeper in tissue. During the second pulse, no PNBs or only small ones are generated by those cancer cells which already responded with PNBs to the first pulse because the gold cluster is usually destroyed (mechanically scattered) by the PNB (Supplementary Fig. 1), and single scattered nanoparticles cannot generate PNBs under the same fluence as efficiently as clusters can.[34-36] Thus, the following pulse of the higher fluence probes the deeper layer with PNBs (Supplementary Fig. 7b). The laser pulse energy can be automatically switched in real time (within milliseconds) during the laser operation. In addition, the PNB generation depth is independently monitored via the time-delay from the laser pulse to the PNB spike in the time-response (Supplementary Fig. 7c). This simple algorithm does not require signal reconstruction (unlike photoacoustic methods) because both the PNB signal amplitude and time-delay are directly read from the primary signal. In this multi-pulse mode, PNBs not just detect deeper micro-tumours, but will also indicate the depth of the MRD, thus helping a surgeon to plan the follow-up resection.

3. Verification of cancer cell selectivity of PNBs. Unlike other thermal or mechanical events, the mechanical impact of PNB is localized within the cell where the PNB is generated and is precisely controlled with the fluence of the laser pulse (Fig. 3b in ref 34). According to this data, our surface fluence of 70 mJ/cm$^2$ is perfectly safe to normal cells and even allows further increase in the fluence (was not available with our current model of the laser and requires a purchase of the new laser). In the *in vitro* clonogenic study of HN31 and normal cells, their identical treatment with gold and laser pulses resulted in high safety and viability of normal cells up to the laser pulse fluence levels of 140 mJ/cm$^2$ (while cancer cells were effectively destroyed with the mechanical impact of intracellular PNBs). This single cancer cell specificity of the mechanical impact of PNBs was tested in a simple experiment with the mixture of identically gold- and laser-treated normal and HNSCC cells (Supplementary movie file). In this experiment, cancer and normal cells were identically pretreated *in vitro* with gold conjugates as described above, and 24 h later were mixed and exposed to a single broad laser pulse (which simultaneously irradiated both normal and cancer cells). As can be seen in the movie, only a cancer cell (in the centre) explodes while adjacent normal cells remain intact and survive the laser impact and the generation of the PNB in cancer cell.

This cluster-threshold PNB mechanism was verified *in vivo* in the primary tumour model described above. The gold cluster size was correlated with PNB metrics for tumours and normal tissues[37]: the cluster size *in vivo* (directly measured with TEM in the tumour and normal adjacent tissue) was correlated to the PNB lifetime in the tissue slices harvested from a tumour and normal adjacent tissue (Fig. 3c, in ref 37) and the amplitude of acoustic time-response (Fig. 4d, in ref 37). Both PNB metrics revealed the high tumour specificity of PNBs which correlated to the TEM data for gold clusters (Fig. 3a,b, in ref 37). This result was in line with the dependence of the PNB generation threshold upon the gold cluster size: the lowest around large clusters (in tumours) and the highest around single nanoparticles in adjacent normal tissue.[35,36] In the current study, we further verified our gold clustering method with the results of the PNB diagnostics (Fig. 5) and the PNB-guided surgical outcome (Fig. 6a and b): no PNBs would have been generated otherwise around non-clustered single gold nanoparticles. Thus, the gold cluster–threshold mechanism of PNB generation successfully overcomes the problem of non-specific uptake of nanoparticles by normal tissues (this problem remains the major limitation in the specificity of all material-based diagnostic methods).

D: Supplementary References

1. Razansky, D, Vinegoni, C & Ntziachristos, V. Multispectral photoacoustic imaging of fluorochromes in small animals. *Opt. Lett.* 32, 2891–2893 (2007).

2. Razansky, D, *et al.* Multispectral opto-acoustic tomography of deep-seated fluorescent proteins in vivo. *Nat. Photonics* 3, 412–417 (2009).

3. Ma, R, Taruttis, A, Ntziachristos, V & Razansky, D. Multispectral optoacoustic tomography (MSOT) scanner for whole-body small animal imaging. *Opt. Express* 17, 21414-21426 (2009).

4. Ntziachristos, V. Advancing molecular imaging with Multi-Spectral Opto-Acoustic Tomography (MSOT). *IEEE International Symposium Biomedical Imaging: From Nano to Macro. ISBI* 1202-1202 (2009).

5. Dean-Ben, XL, Ma, R, Razansky, D, & Ntziachristos, V. Statistical approach for optoacoustic image reconstruction in the presence of strong acoustic heterogeneities. *IEEE Trans. Med. Imaging* 30, 401-408 (2011).

6. Herzog, E, Taruttis, A, Lutich, A, Razansky, D & Ntziachristos, V. Optical imaging of cancer heterogeneity by means of multispectral optoacoustic tomography (MSOT). *Radiology* 263, 461-468 (2012).

7. Kimbrough, CW, Hudson, S, Khanal, A, Egger, ME & McNally, LR. Orthotopic pancreatic tumors detected by optoacoustic tomography using Syndecan-1. *J. Surg. Res.* 193, 246-254 (2015).

8. Beziere, N, et al. Dynamic imaging of PEGylated indocyanine green (ICG) liposomes within the tumor microenvironment using multi-spectral optoacoustic tomography (MSOT). *Biomaterials* 37, 415-424 (2015).

9. Burton, NC, et al. Multispectral opto-acoustic tomography (MSOT) of the brain and glioblastoma characterization. *NeuroImage* 65, 522–528 (2013).

10. Tzoumas, S, Deliolanis, NC, Morscher, S & Ntziachristos, V. Unmixing molecular agents from absorbing tissue in multispectral optoacoustic tomography. *IEEE Trans. Med. Imaging* 33, 48-60 (2014)

11. Hudson, SV, et al. Targeted noninvasive imaging of EGFR-expressing orthotopic pancreatic cancer using multispectral optoacoustic tomography. *Cancer Res.* 74, 6271-6279 (2014).

12. Balasundaram, G, et al. Molecular photoacoustic imaging of breast cancer using an actively targeted conjugated polymer. *Int. J. Nnaomedicine* 10, 387-397 (2015).

13. Bao, C, et al. Gold nanoprisms as optoacoustic signal nanoamplifiers for in vivo bioimaging of gastrointestinal cancers. *Small* 9, 68-74 (2013).

14. Tzoumas, S, et al. Immune cell imaging using multi-spectral optoacoustic tomography. *Opt. Letters* 39, 3523-3526 (2015).

15. Taruttis, A, Morscher, S, Burton, NC, Razansky, D & Ntziachristos, V. Fast Multispectral Optoacoustic Tomography (MSOT) for dynamic imaging of pharmacokinetics and biodistribution in multiple organs. *PLoS ONE* 7, e30491 (2012).

16. de Boer, E, *et al.* Optical innovations in surgery. *BJS* 105, e56-e72 (2015).

17. Taruttis, A, & Ntziachristos, V. Advances in real-time multispectral optoacoustic imaging and its applications. *Nat. Photonics* 9, 219-227 (2015).

18. Taruttis, A, *et al.* Multispectral optoacoustic tomography of myocardial infarction. *Photoacoustics* 1, 3–8 (2013).

19. Dima, A, Gateau, J, Claussen, J, Wilhelm, D & Ntziachristos, V. Optoacoustic imaging of blood perfusion: techniques for intraoperative tissue viability assessment. *J. Biophotonics* 6, 485–492 (2013).

20. Ntziachristos, V. Clinical translation of optical and optoacoustic images. *Phil. Trans. R. Soc. A* 369, 466-4678 (2011).

21. Buehler, A, Kacprowicz, M, Taruttis, A & Ntziachristos, V. Real-time handheld multispectral optoacoustic imaging. *Opt. Letters* 38, 1404-1406 (2013).

22. Lutzweiler, C, Meier, R, Rummeny, E, Ntziachristos, V & Razansky, D. Real-time optoacoustic tomography of indocyanine green perfusion and oxygenation parameters in human finger vasculature. *Opt. Letters* 39, 4061-4064 (2014).

23. https://clinicaltrials.gov/ct2/show/NCT01508572?term=MSOT&rank=2; Clinical trial: NCT01508572.

24. Razansky, D, Baeten, J & Ntziachristos, V. Sensitivity of molecular target detection by multispectral optoacoustic tomography (MSOT). *Med. Phys.* 36, 939–945 (2009).

25. Rosenthal, A, Razansky, D & Ntziachristos, V. Quantitative optoacoustic signal extraction using sparse signal representation. *IEEE Trans. Med. Imaging* 28, 1997-2006 (2009).

26. Mancas, E, Tzoumas, S, Ntziachristos, V & Spyrou, G. Developing a simulator for multispectral optoacoustic tomography. *Bioinformatics and Bioengineering (BIBE), 2013 IEEE 13th International Conference* 1-4 (2013).

27. Taruttis, A, Rosenthal, A, Kacprowicz, M, Burton, NC & Ntziachristos, V. Multiscale multispectral optoacoustic tomography by a stationary wavelet transform prior to unmixing, *IEEE Trans. Med. Imaging*. 33, 1194-202 (2014).

28. Yuan, Z & Jiang, HB. Simultaneous recovery of tissue physiological and acoustic properties and the criteria for wavelength selection in multispectral photoacoustic tomography. *Opt. Lett.* 34, 1714–1716 (2009).

29. Zhang, E, Laufer, J & Beard, P. Backward-mode multiwavelength photoacoustic scanner using a planar Fabry-Perot polymer film ultrasound sensor for high-resolution three-dimensional imaging of biological tissues. *Appl. Opt.* 47, 561–577 (2008).

30. Jose, J, et al. Initial results of imaging melanoma metastasis in resected human lymph nodes using photoacoustic computed tomography. *J. Biomed. Opt.* 16, 096021 (2011).

31. Li, R, et al. Assessing breast tumor margin by multispectral photoacoustic tomography. *Biomed. Opt. Express* 6, 1273-1281 (2015).

32. Stoffels, I, et al. Clinical application of noninvasive and nonradioactive determination of microscopic lymph node tumor status by multispectral optoacoustic imaging. *J. Nuclear Medicine* 56(supplement 3), 40 (2015).

33. Chagpar, AB, et al. A randomized, controlled trial of cavity shave margins in breast cancer. *New England J. Med.* 373, 503-510 (2015).

34. Lukianova-Hleb, EY, *et al.* On-demand intracellular amplification of chemoradiation with cancer-specific plasmonic nanobubbles. *Nat. Med.* 20, 778-784 (2014).

35. Lukianova-Hleb, E, *et al.* Plasmonic nanobubbles as transient vapor nanobubbles generated around plasmonic nanoparticles. *ACS Nano* 4, 2109–2123 (2010).

36. Lukianova-Hleb, EY, *et al.* Improved cellular specificity of plasmonic nanobubbles versus nanoparticles in heterogeneous cell systems. *PLoS ONE* 7, e34537 (2012).

37. Lukianova-Hleb, EY, *et al.* Plasmonic nanobubbles rapidly detect and destroy drug-resistant tumors. *Theranostics* 2, 976-987 (2012).

What is claimed is:

1. A cancer detection system configured to noninvasively determine a presence of unwanted cancerous material in tissue using plasmonic nanobubbles ("PNBs"), said cancer detection system returning post-electronic processing results to an operator at least at each measurement site during a cancer detection procedure, said cancer detection system comprising:
   a plurality of bioconjugated nanoparticles configured to be administered to a patient at a predetermined time prior to said cancer detection procedure, the bioconjugated nanoparticles comprising a plurality of nanoparticles and a plurality of cancerous material-specific ligands configured to attach to and cluster in said unwanted cancerous material;
   a source of electromagnetic radiation configured to provide a plurality of radiation pulses at a plurality of energy levels to said tissue at said measurement site; and
   an acoustic detector configured to output signals responsive to a plurality of pressure pulses emitted by PNBs from at least some of the bioconjugated nanoparticles when said tissue includes said unwanted cancerous material; and
   one or more signal processors operably communicating with said acoustic detector and configured to receive said output signals or one or more pre-processed signals responsive to said signals, configured to electronically process said signals or said one or more pre-processed signals, and configured to notify said operator with a result of said processing at each measurement site, said processing including:
      determining a first acoustic time-response responsive to said signals or said pre-processed signals corresponding to one or more of said pulses of said source at a first energy level;
      comparing said first acoustic time-response with a PNB-negative time-response to determine a detection of the PNBs; and
      when a sufficient amount of said presence is determined, returning a positive result for said presence of said unwanted cancerous material.

2. The cancer detection system of claim 1 further configured to noninvasively determine a depth of unwanted cancerous material, wherein said one or more signal processors electronically process said signals or said one or more pre-processed signals, and said processing further includes:
   determining another acoustic time-response responsive to said signals or said pre-processed signals corresponding to one or more of said pulses of said source at an increased energy level, the increased energy level configured to cause said pulses of said source to reach tissue at an increased depth;
   comparing said another acoustic time-response with said PNB-negative time-response;
   when said comparison of said another acoustic time-response is negative, additionally returning a positive result for said presence of said unwanted cancerous material at the increased depth at said measurement site; and
   repeating said determining using said increased energy level, comparing and returning until said of said repeating step comparing is positive and said one or more processors return a negative result for said unwanted cancerous material at the increased depth.

3. The system of claim 2, wherein said cancerous material includes cancer cells, cancerous microtumors, or cancerous tumor associated vasculature.

4. The cancer detection system of claim 1, wherein said cancerous material includes cancer cells, cancerous microtumors, or cancerous tumor associated vasculature.

5. The system of claim 1, wherein said source provides said plurality of said radiation pulses, at least some of said radiation pulses provided at wavelengths between about 600 and about 1,500 nm.

6. The system of claim 1, wherein said source provides said plurality of said radiation pulses, at least some of said radiation pulses provided at a wavelength of about 782 nm.

7. The system of claim 1, wherein said source provides said plurality of said radiation pulses, at least some of said radiation pulses having a duration not exceeding about 100 ps.

8. The system of claim 1, wherein said duration is about 30 ps.

9. The system of claim 1, comprising a medical apparatus configured to position or house said source.

10. The system of claim 9, wherein said medical apparatus comprises a robotic arm.

11. The system of claim 9, wherein said medical apparatus comprises a laparoscopic tool.

12. The system of claim 9, wherein said medical apparatus comprises an endoscope.

13. The system of claim 1, wherein the cancerous material-specific ligands comprise an antibody.

14. The system of claim 13, wherein the antibody comprises different antibodies.

15. A noninvasive process to determine cancer in tissue using plasmonic nanobubbles ("PNBs"), said process comprising:
   administering bioconjugated nanoparticles to a patient, the bioconjugated nanoparticles comprising a plurality of nanoparticles and a plurality of bonded cancer-specific or tumor-associated vasculature-specific ligands;
   emitting from a laser source a laser pulse at an energy to tissue at a measurement site of said patient;
   detecting with a detector one or more pressure pulses from a group of PNBs, if any, responsive to said laser pulse;
   electronically processing with one or more signal processors, one or more signals responsive to said detecting, said processing including:
   electronically determining a time-response;
   electronically comparing the time-response to a threshold; and
   when said time-response is greater than said threshold, outputting indicia to a monitor, said indicia usable to conclude one or more of cancer cells or tumor-specific vasculature exist in said tissue.

16. The process of claim 15, wherein when said time-response is greater than said threshold, increasing said energy of said laser pulse and repeating said detecting, emitting, and said processing to determine whether said cancer cells or tumor-specific vasculature exist in said tissue at an increase of said.

17. The process of claim 16, wherein said repeating terminates when said time-response is less than said threshold.

18. The process of claim 15, wherein when said time-response is greater than said threshold, generating an output usable by a surgeon to determine whether to resect a portion of said tissue defined by a footprint of a PNB probe.

19. The process of claim 18, wherein said emitting, outputting, processing, and generating repeats with each resection of said portion of said tissue.

\* \* \* \* \*

UNITED STATES PATENT AND TRADEMARK OFFICE
CERTIFICATE OF CORRECTION

PATENT NO. : 10,471,159 B1
APPLICATION NO. : 15/430321
DATED : November 12, 2019
INVENTOR(S) : Dmitri O. Lapotko It is certified that error appears in the above-identified patent and that said Letters Patent is hereby corrected as shown below:

In the Specification

In Column 27, at Lines 29-30, delete "PNB s" and insert --PNBs--.

In Column 27, at approximately Line 37, delete "PNB s" and insert --PNBs--.

In the Claims

In Column 137, at Lines 64-65, in Claim 2, delete "of said repeating step comparing" and insert --comparing of said repeating step--.

In Column 138, at Line 18, in Claim 8, delete "1," and insert --7,--.

Signed and Sealed this
Nineteenth Day of May, 2020

Andrei Iancu
*Director of the United States Patent and Trademark Office*